US007589207B2

(12) United States Patent
Duan et al.

(10) Patent No.: US 7,589,207 B2
(45) Date of Patent: Sep. 15, 2009

(54) CYCLOHEXYL COMPOUNDS AS CCR5 ANTAGONISTS

(75) Inventors: Maosheng Duan, Durham, NC (US); Wieslaw Mieczyslaw Kazmierski, Durham, NC (US); Christopher Joseph Aquino, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 542 days.

(21) Appl. No.: 10/538,135

(22) PCT Filed: Dec. 12, 2003

(86) PCT No.: PCT/US03/39732

§ 371 (c)(1), (2), (4) Date: Jun. 9, 2005

(87) PCT Pub. No.: WO2004/054581

PCT Pub. Date: Jul. 1, 2004

(65) Prior Publication Data

US 2006/0122166 A1    Jun. 8, 2006

Related U.S. Application Data

(60) Provisional application No. 60/433,552, filed on Dec. 13, 2002.

(51) Int. Cl.
  *C07D 451/00* (2006.01)
  *A01N 43/42* (2006.01)
(52) U.S. Cl. ...................... 546/126; 514/304
(58) Field of Classification Search ................ 546/229, 546/124; 514/331, 304
  See application file for complete search history.

(56) References Cited

U.S. PATENT DOCUMENTS

| | | | |
|---|---|---|---|
| 6,479,487 B1 | 11/2002 | Borcherding et al. | |
| 7,105,507 B2 * | 9/2006 | Castro Pineiro et al. | 514/212.01 |
| 7,271,172 B2 * | 9/2007 | Yang et al. | 514/278 |
| 2006/0052595 A1 * | 3/2006 | Aquino et al. | 544/78 |
| 2006/0229336 A1 * | 10/2006 | Kazmierski et al. | 514/317 |

FOREIGN PATENT DOCUMENTS

| | | |
|---|---|---|
| DE | 44 17 163 | 11/1995 |
| EP | 1 182 195 | 2/2002 |
| EP | 1 236 726 | 9/2002 |
| EP | 1 378 510 | 1/2004 |
| EP | 1 403 25 | 3/2004 |
| WO | WO 97/09308 | 3/1997 |
| WO | WO 97/20823 | 6/1997 |
| WO | WO 98/25897 | 6/1998 |
| WO | WO 99/59974 | 11/1999 |
| WO | WO 99/64044 | 12/1999 |
| WO | WO 00/49018 | 8/2000 |
| WO | WO 01/36418 | 5/2001 |
| WO | WO 01/72751 | 10/2001 |
| WO | WO 01/90106 | 11/2001 |
| WO | WO 02/18335 | 3/2002 |
| WO | WO 03/028641 | 4/2003 |
| WO | WO 03/069237 | 8/2003 |
| WO | WO 03/070244 | 8/2003 |
| WO | WO 03/075853 | 9/2003 |
| WO | WO 03/087098 | 10/2003 |

OTHER PUBLICATIONS

Tyle, Iontonphoretic Devices for Drug Delivery, Pharm. Res. 3(6):318-326 (1986).
Woltersdorf et al., Topically Active Anhydrase Inhibitors, J. of Medicinal Chemsitry, ACS 32(11):2486-2492 (1989).
Witherington et l., Conformationally restricted indolopiperidine derivates as potent CCR28 receptor antagonists, Bioorg. & Med. Chem Lett. 11(16):2177-2180 (2001.

* cited by examiner

*Primary Examiner*—Rita J Desai
*Assistant Examiner*—John Mabry
(74) *Attorney, Agent, or Firm*—Bonnie L. Deppenbrock

(57) ABSTRACT

The present invention relates to compounds of formula (I), or pharmaceutically acceptable derivatives thereof, useful in the treatment of CCR5-related diseases and disorders, for example, useful in the inhibition of HIV replication, the prevention or treatment of an HIV infection, and in the treatment of the resulting acquired immune deficiency syndrome (AIDS).

4 Claims, No Drawings

CYCLOHEXYL COMPOUNDS AS CCR5 ANTAGONISTS

CROSS-REFERENCE TO RELATED APPLICATIONS

This application is filed pursuant to 35 USC 371 as a United States National Phase Application of International Patent Application Serial No. PCT/US03/39732 filed on Dec. 12, 2003, which claims priority from U.S. Provisional Application No. 60/433,552 filed on Dec. 13, 2002.

BACKGROUND OF THE INVENTION

The human immunodeficiency virus ("HIV") is the causative agent for acquired immunodeficiency syndrome ("AIDS"), a disease characterized by the destruction of the immune system, particularly of CD4+ T-cells, with attendant susceptibility to opportunistic infections, and its precursor AIDS-related complex ("ARC"), a syndrome characterized by symptoms such as persistent generalized lymphadenopathy, fever and weight loss.

In addition to CD4, HIV requires a co-receptor for entry into target cells. The chemokine receptors function together with CD4 as co-receptors for HIV. The chemokine receptors CXCR4 and CCR5 have been identified as the main co-receptors for HIV-1. CCR5 acts as a major co-receptor for fusion and entry of macrophage-tropic HIV into host cells. These chemokine receptors are thought to play an essential role in the establishment and dissemination of an HIV infection. Therefore, CCR5 antagonists are thought to be useful as therapeutic agents active against HIV.

We have now discovered a series of small molecule non-peptide compounds that are useful as inhibitors of HIV replication.

BRIEF DESCRIPTION OF THE INVENTION

The present invention features compounds that are useful in the inhibition of HIV replication, the prevention of infection by HIV, the treatment of infection by HIV and in the treatment of AIDS and/or ARC, either as pharmaceutically acceptable salts or pharmaceutical composition ingredients. The present invention further features methods of treating AIDS, methods of preventing infection by HIV, and methods of treating infection by HIV as monotherapy or in combination with other antivirals, anti-infectives, immunomodulators, antibiotics or vaccines. The present invention also features pharmaceutical compositions, comprising the above-mentioned compounds that are suitable for the prevention or treatment of CCR5-related diseases and conditions. The present invention further features processes for making the above-mentioned compounds.

SUMMARY OF THE INVENTION

The present invention includes a compound of formula (I)

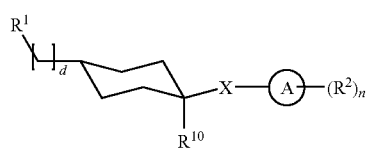

(I)

or a pharmaceutically acceptable salt, solvate, or derivative thereof, wherein:

X is a $C_{1-5}$ alkylene chain, wherein said X is optionally substituted by one or more =O, =S, —S(O)$_t$—, alkyl, or halogen and wherein said $C_{1-5}$ alkylene chain may optionally have 0-3 heteroatoms selected from oxygen, phosphorus, sulfur, or nitrogen;

Ring A is a saturated, partially saturated or aromatic 3-7 monocyclic or 8-10 membered bicyclic ring having one ring nitrogen and 0-4 additional heteroatoms selected from oxygen, phosphorus, sulfur, or nitrogen;

$R^1$ is selected from the group consisting of (a) a saturated, partially saturated, or aromatic 4-7 monocyclic or 8-10 membered bicyclic ring having one ring nitrogen and 04 additional heteroatoms selected from oxygen, phosphorus, sulfur, or nitrogen, optionally attached through a $C_{1-6}$ alkylene chain, and optionally substituted by one or more $R^8$;

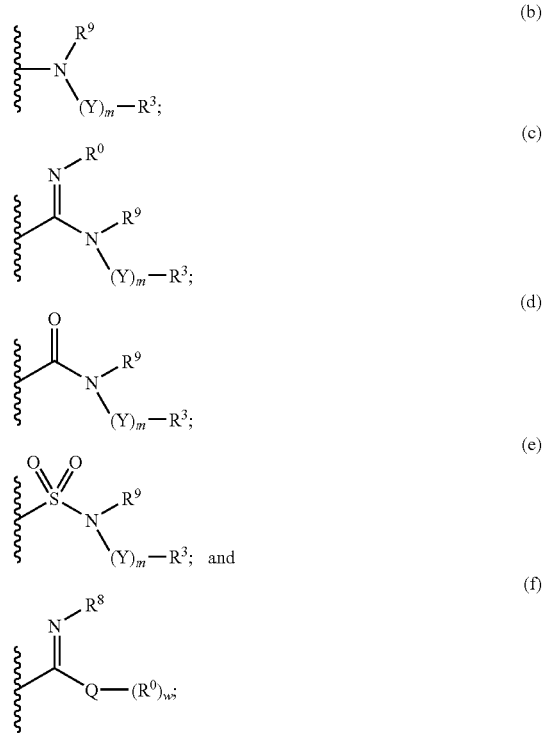

Q is carbon, oxygen, or —S(O)$_t$;

w is 1 or 2;

each $R^2$ is independently selected from the group consisting of —OR$^0$, —C(O)—R$^0$, —S(O)$_2$—R$^0$, —C(O)—N(R$^0$)$_2$, —S(O)$_2$—N(R$^0$)$_2$, —(CH$_2$)$_a$—N(R$^0$)(—V$_b$—R$^+$), —(CH$_2$)$_a$—(—V$_b$—R$^+$), halogen, alkyl optionally substituted by one or more $R^7$, alkenyl optionally substituted by one or more $R^7$, alkynyl optionally substituted by one or more $R^7$, aryl optionally substituted by one or more $R^6$, heteroaryl optionally substituted by one or more $R^6$, cycloalkyl optionally substituted by one or more $R^8$, and heterocyclyl optionally substituted by one or more $R^8$; and two adjacent $R^2$s on Ring A are optionally taken together to form a fused, saturated, partially saturated or aromatic 5-6 membered ring having 0-3 heteroatoms selected from oxygen, phosphorus, sulfur, or nitrogen; or two geminal $R^2$s are optionally taken together to form a spiro, saturated, partially saturated or aromatic 5-6 membered ring having 0-3 heteroatoms selected from oxygen, phosphorus, sulfur, or nitrogen, said fused or spiro ring being optionally substituted by one or more $R^8$;

a is 0-3;

b is 0 or 1;

V is —C(O)—, —C(O)O—, —S(O)$_2$—, or —C(O)—N($R^O$)—;

$R^+$ is alkyl, cycloalkyl, aralkyl, aryl, heteroaryl, heteroaralkyl, or heterocyclyl, wherein said $R^+$ is optionally substituted by one or more $R^8$;

d is 0-1;

m is 0 or 1;

n is 0-5;

each $R^3$ independently is H, —N($R^O$)$_2$, —N($R^O$)C(O)$R^O$, —CN, halogen, —CF$_3$, alkyl optionally substituted by one or more groups selected from $R^7$ or —S-aryl optionally substituted by —(CH$_2$)$_{1-6}$N($R^O$)SO$_2$($R^O$), alkenyl optionally substituted by one or more groups selected from $R^7$ or —S-aryl optionally substituted by —(CH$_2$)$_{1-6}$N($R^O$)SO$_2$($R^O$), alkynyl optionally substituted by one or more groups selected from $R^7$ or —S-aryl optionally substituted by —(CH$_2$)$_{1-6}$—N($R^O$)SO$_2$($R^O$), cycloalkyl or carbocyclyl optionally substituted by one or more $R^8$, aryl optionally substituted by one or more $R^6$, heteroaryl optionally substituted by one or more $R^6$, or heterocyclyl optionally substituted by one or more $R^8$;

Y is alkyl, alkenyl, alkynyl, —(CR$^4$R$^5$)$_p$—, —C(O)—, —C(O)C(O)—, —C(S)—, —O—(CH$_2$)$_{0-4}$—C(O)—, —(CH$_2$)$_{0-4}$—C(O)—O—, —N($R^O$)—C(O)—, —C(O)—N($R^O$)—, —N($R^O$)—C(S)—, —S(O)$_t$—, —O—C(=N—CN)—, —O—C(=N—$R^O$)—, —C(=N—CN)—O—, —C(=N—CN)—S—, —C(=N—$R^O$)—O—, —S—C(=N—CN)—, —N($R^O$)—C(=N—CN)—, —C(=N—CN), —N($R^O$)—C[=N—C(O)—$R^O$]—, —N($R^O$)—C[=N—S(O)$_t$—$R^O$]—, —N($R^O$)—C(=N—O$R^O$)—, —N($R^O$)—C(=N—$R^O$)—, or —C(=N—R)—;

each $R^4$ independently is H or alkyl optionally substituted by $R^7$, alkenyl optionally substituted by $R^7$, alkynyl optionally substituted by $R^7$;

each $R^5$ independently is selected from the group consisting of —H, —C(O)—O$R^6$, —C(O)—N($R^O$)$_2$, —S(O)$_2$—N($R^O$)$_2$, —S(O)$_2$—$R^6$, aryl optionally substituted by $R^6$, or heteroaryl optionally substituted by $R^6$;

p is 1-5;

each t independently is 1 or 2;

each $R^6$ is independently selected from the group consisting of halogen, —CF$_3$, —OCF$_3$, —O$R^O$, —(CH$_2$)$_{1-6}$—O$R^O$, —S$R^O$, —(CH$_2$)$_{1-6}$—S$R^O$, —SCF$_3$, —$R^O$, methylenedioxy, ethylenedioxy, —NO$_2$, —CN, —(CH$_2$)$_{1-8}$—CN, —N($R^O$)$_2$, —(CH$_2$)$_{1-6}$—N($R^O$)$_2$, —NR$^O$C(O)$R^O$, —NR$^O$(CN), —NR$^O$C(O)N($R^O$)$_2$, —NR$^O$C(S)N($R^O$)$_2$, —NR$^O$CO$_2$$R^O$, —NR$^O$NR$^O$C(O)$R^O$, —NR$^O$NR$^O$C(O)N($R^O$)$_2$, —NR$^O$NR$^O$CO$_2$$R^O$, —C(O)C(O)$R^O$, —C(O)CH$_2$C(O)$R_1$, —(CH$_2$)$_{0-6}$CO$_2$$R^O$, —O—C(O)$R^O$, —C(O)$R^O$, —C(O)N($R^O$)N($R^O$)$_2$, —C(O)N($R^O$)$_2$, —C(O)N($R^O$)OH, —C(O)N($R^O$)SO$_2$$R^O$, —OC(O)N($R^O$)$_2$, —S(O)$_t$$R^O$, —S(O)$_t$—O$R^O$, —S(O)$_t$N($R^O$)C(O)$R^O$, —S(O)$_t$N($R^O$)O$R^O$, —NR$^O$SO$_2$N($R^O$)$_2$, —NR$^O$SO$_2$$R^O$, —C(=S)N($R^O$)$_2$, —C(=NH)—N($R^O$)$_2$, —(CH$_2$)$_{1-6}$—C(O)$R^O$, —C(=N—O$R^O$)—N($R^O$)$_2$, —O—(CH$_2$)$_{0-4}$—SO$_2$N($R^O$)$_2$, —(CH$_2$)$_{1-6}$NHC(O)$R^O$, or —SO$_2$N($R^O$)$_2$ wherein the two $R^O$s on the same nitrogen are optionally taken together to form a 5-8 membered saturated, partially saturated, or aromatic ring having additional 0-4 heteroatoms selected from oxygen, phosphorus, nitrogen, or sulfur;

each $R^7$ is independently selected from the group consisting of halogen, —CF$_3$, —$R^O$, —O$R^O$, —OCF$_3$, —(CH$_2$)$_{1-6}$—O$R^O$, —S$R^O$, —SCF$_3$, —(CH$_2$)$_{1-6}$—S$R^O$, aryl optionally substituted by $R^6$, methylenedioxy, ethylenedioxy, —NO$_2$, —CN, —(CH$_2$)$_{1-4}$—CN, —N($R^O$)$_2$, —(CH$_2$)$_{1-6}$—N($R^O$)$_2$, —NR$^O$C(O)$R^O$, —NR$^O$(CN), —NR$^O$C(O)N($R^O$)$_2$, —NR$^O$C(S)N($R^O$)$_2$, —NR$^O$CO$_2$$R^O$, —NR$^O$NR$^O$C(O)$R^O$, —NR$^O$NR$^O$C(O)N($R^O$)$_2$, —NR$^O$NR$^O$CO$_2$$R^O$, —C(O)C(O)$R^O$, —C(O)CH$_2$C(O)$R^O$, —(CH$_2$)$_{0-6}$—CO$_2$$R^O$, —C(O)$R^O$, —C(O)N($R^O$)N($R^O$)$_2$, —C(O)N($R^O$)$_2$, —C(O)N($R^O$)OH, —OC(O)$R^O$, —C(O)N($R^O$)SO$_2$$R^O$, —OC(O)N($R^O$)$_2$, —S(O)$_t$$R^O$, —S(O)$_t$O$R^O$, —S(O)$_t$N($R^O$)C(O)$R^O$, —S(O)$_t$N($R^O$)O$R^O$, —NR$^O$SO$_2$N($R^O$)$_2$, —NR$^O$SO$_2$$R^O$, —C(=S)N($R^O$)$_2$, —C(=NH)—N($R^O$)$_2$, —(CH$_2$)$_{1-6}$—C(O)$R^O$, —C(=N—O$R^O$)—N($R^O$)$_2$, —O—(CH$_2$)$_{0-6}$—SO$_2$N($R^O$)$_2$, —(CH$_2$)$_{1-6}$—NHC(O)$R^O$, and —SO$_2$N($R^O$)$_2$ wherein the two $R^O$s on the same nitrogen are optionally taken together to form a 58 membered saturated, partially saturated, or aromatic ring having additional 0-4 heteroatoms selected from oxygen, phosphorus, nitrogen, or sulfur;

each $R^8$ independently is selected from the group consisting of $R^7$, =O, =S, =N($R^O$), and =N(CN);

$R^9$ is hydrogen, alkyl optionally substituted by one or more $R^7$, alkenyl optionally substituted by one or more $R^7$, alkynyl optionally substituted by one or more $R^7$, cycloalkyl optionally substituted by one or more $R^8$, heterocyclyl optionally substituted by one or more $R^8$, heteroaryl optionally substituted by one or more $R^6$, or aryl optionally substituted by one or more $R^6$; or —(Y)$_m$—$R^3$ and $R^9$ may combine with the nitrogen atom with which they are attached to form a saturated, partially saturated, or aromatic 5-7 membered monocyclic or 810 membered bicyclic ring that optionally contains 1 to 3 additional heteroatoms selected oxygen, phosphorus, sulfur, or nitrogen, wherein said ring may be optionally substituted with one or more $R^8$;

$R^{10}$ is hydrogen, alkyl optionally substituted by one or more $R^7$, alkenyl optionally substituted by one or more $R^7$, alkynyl optionally substituted by one or more $R^7$, cycloalkyl optionally substituted by one or more $R^8$, heterocyclyl optionally substituted by one or more $R^8$, heteroaryl optionally substituted by one or more $R^6$, or aryl optionally substituted by one or more $R^6$;

each $R^O$ is independently selected from the group consisting of hydrogen, alkyl, alkenyl, alkynyl, cycloalkyl, carbocyclylalkyl, aryl, heteroaryl, aralkyl, heteroaralkyl, heterocyclyl, and heterocyclylalkyl, wherein each member of $R^O$ except H is optionally substituted by one or more —R*, —OR*, —N(R*)$_2$, =O, =S, halogen, —CF$_3$, —NO$_2$, —CN, —C(O)R*, —CO$_2$R*, —C(O)-aryl, —C(O)-heteroaryl, aralkyl, —S(O)$_t$-aryl, —S(O)$_t$-heteroaryl, —NR*SO$_2$R*, —NR*C(O)R*, —NR*C(O)N(R*)$_2$, —N(R*)C(S)N(R*)$_2$, —NR*CO$_2$R*, —NR*NR*C(O)R*, —NR*NR*C(O)N(R*)$_2$, —NR*NR*CO$_2$R*, —C(O)C(O)R*, —C(O)CH$_2$C(O)R*, —C(O)N(R*)N(R*)$_2$, —C(O)N(R*)$_2$, —C(O)NR*SO$_2$R*, —OC(O)N(R*)$_2$, —S(O)$_t$R*, —NR*SO$_2$N(R*)$_2$, —SO$_2$N(R*)$_2$ wherein the two R*s on the same nitrogen are optionally taken together to form a 5-8 membered saturated, partially saturated or aromatic ring having additional 04 heteroatoms selected from oxygen, phosphorus, nitrogen or sulfur; and each R* is independently H, alkyl, alkenyl, alkynyl, cycloalkyl, aryl, or heteroaryl.

In one embodiment $R^{10}$ is optionally substituted aryl, such as optionally substituted phenyl.

In one embodiment, $R^1$ is
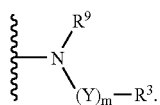
In one embodiment $R^9$ is alkyl and preferably $R^9$ is methyl.
In one embodiment —$(Y)_m$—$R^3$ suitably is
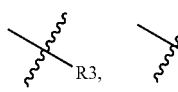
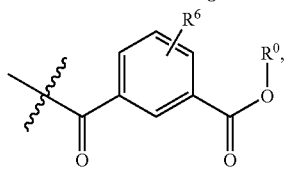
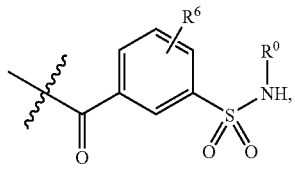
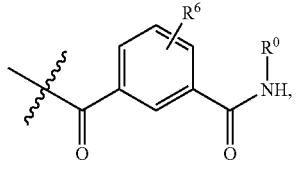
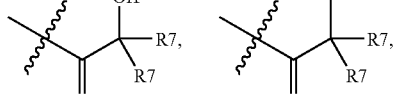
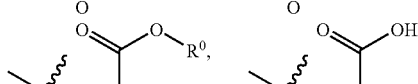
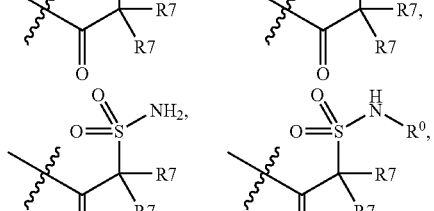
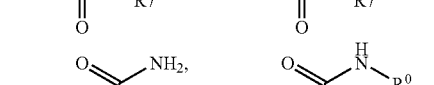
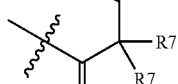
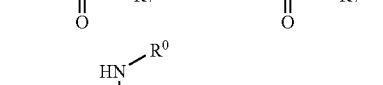
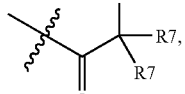
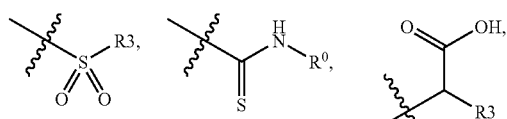
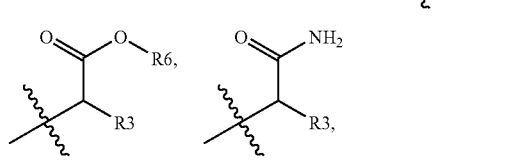
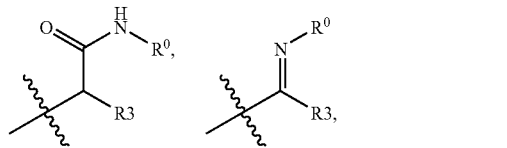
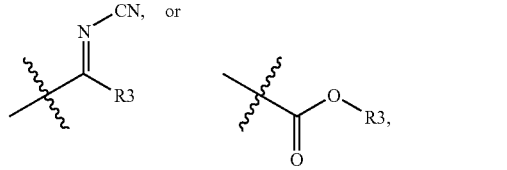
More suitably $(Y)_m$—$R^3$ is
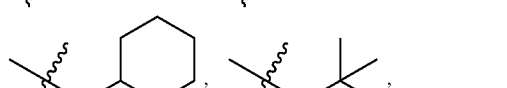
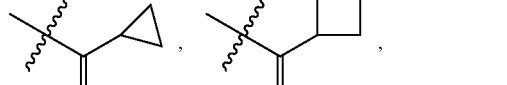
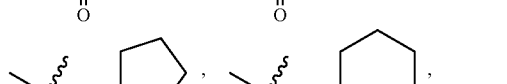
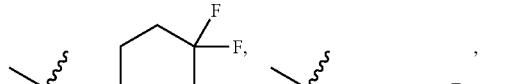
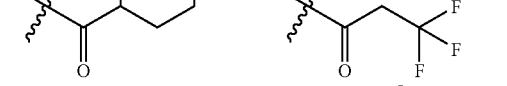
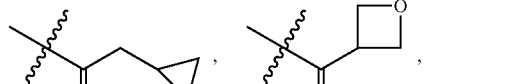
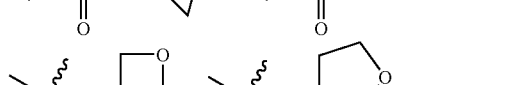
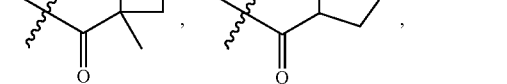

-continued
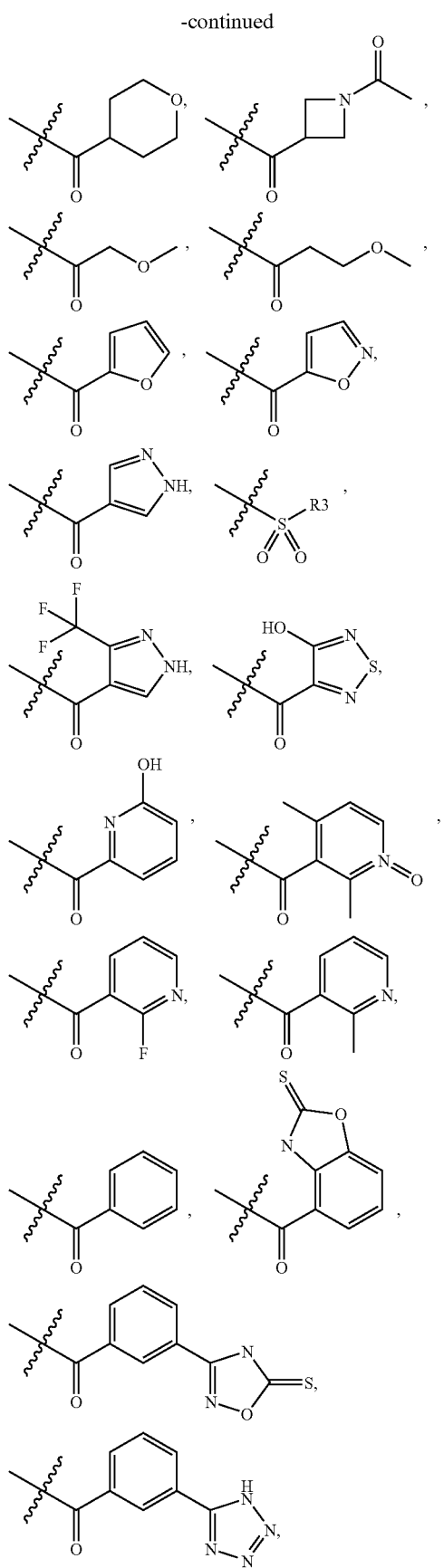
-continued
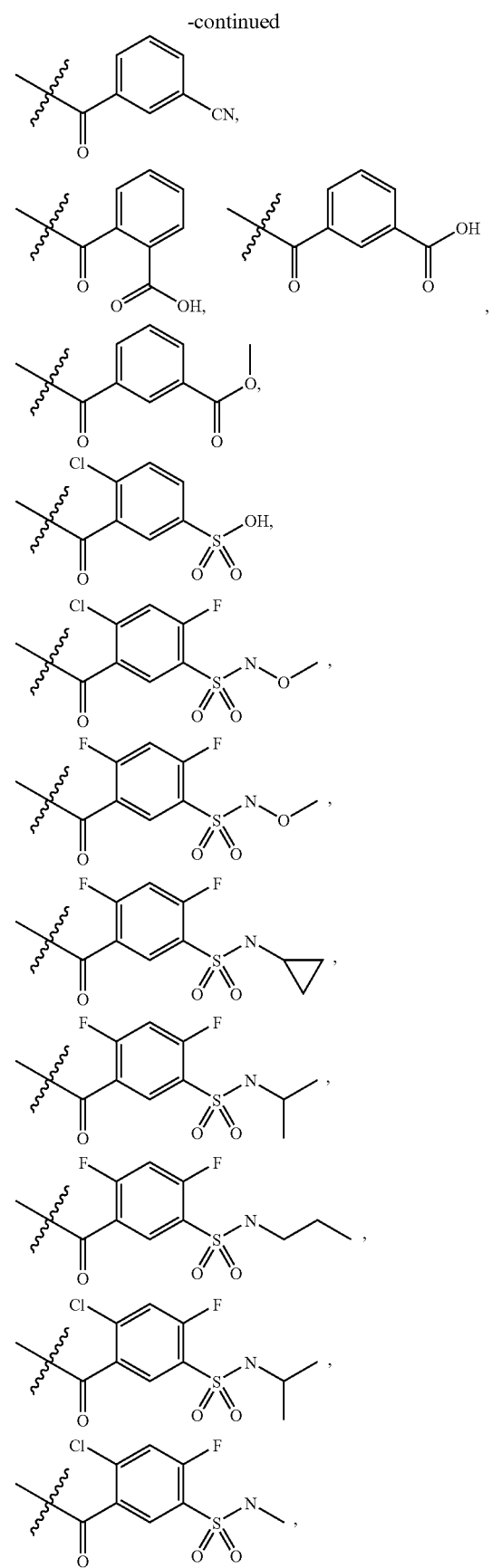

-continued
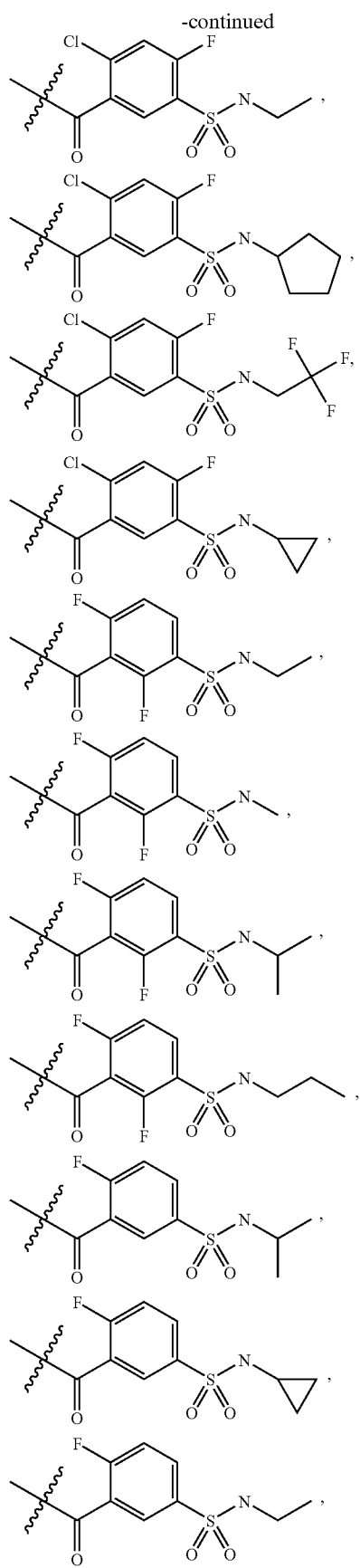
-continued
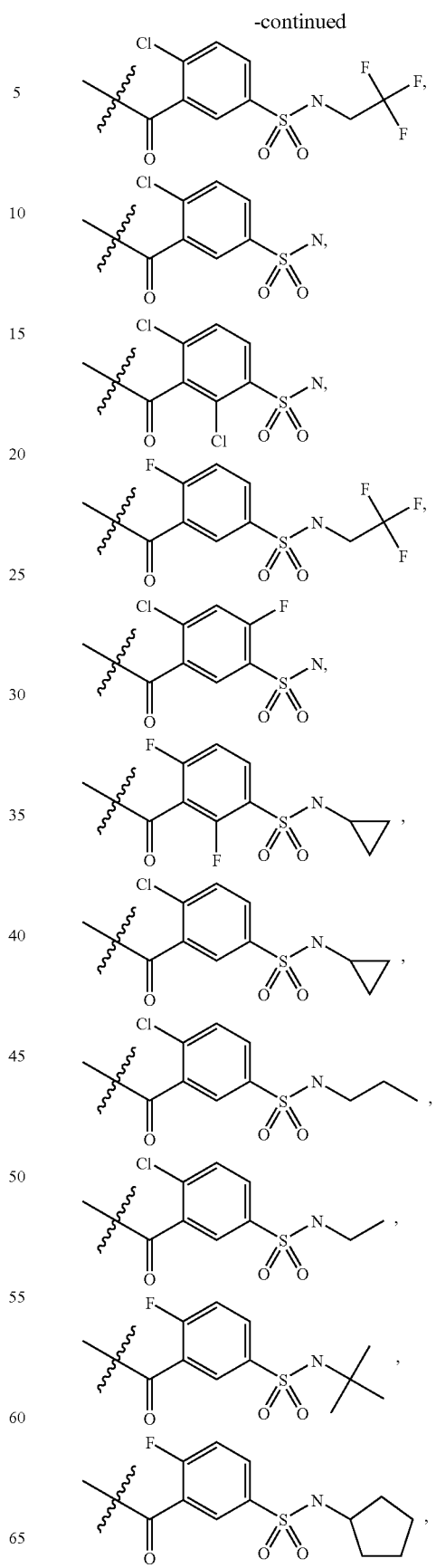

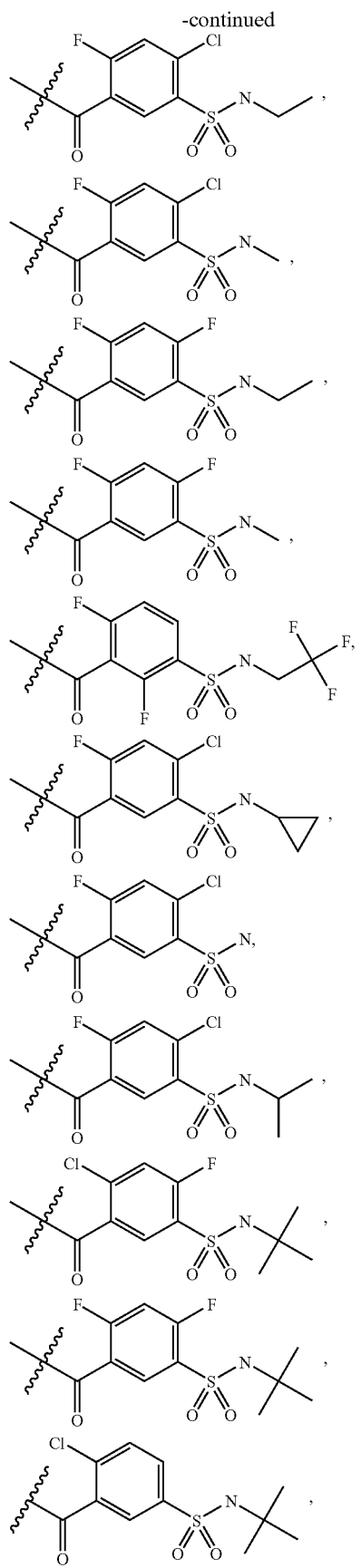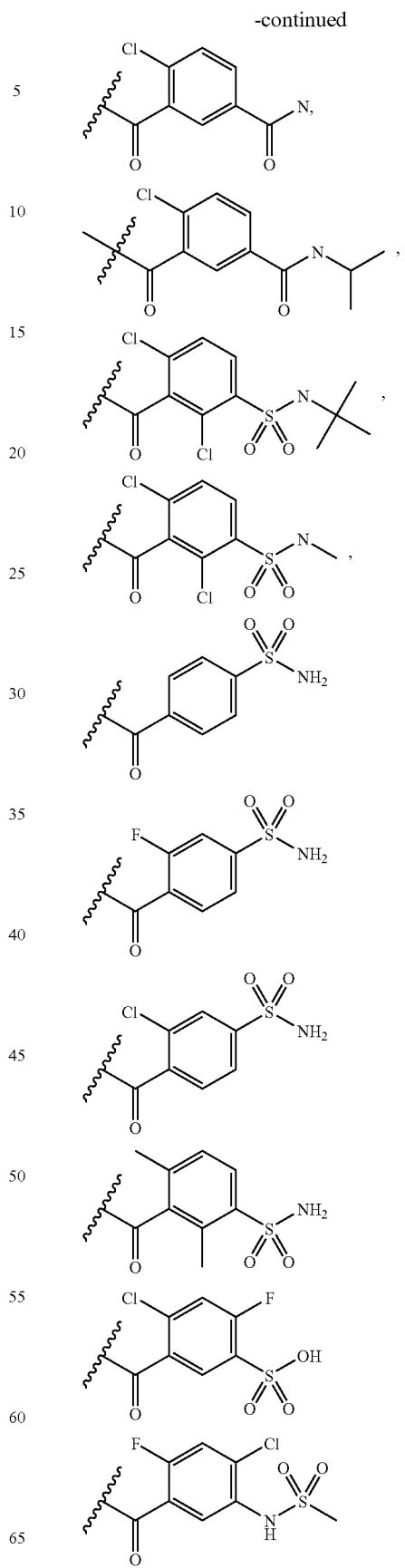

-continued
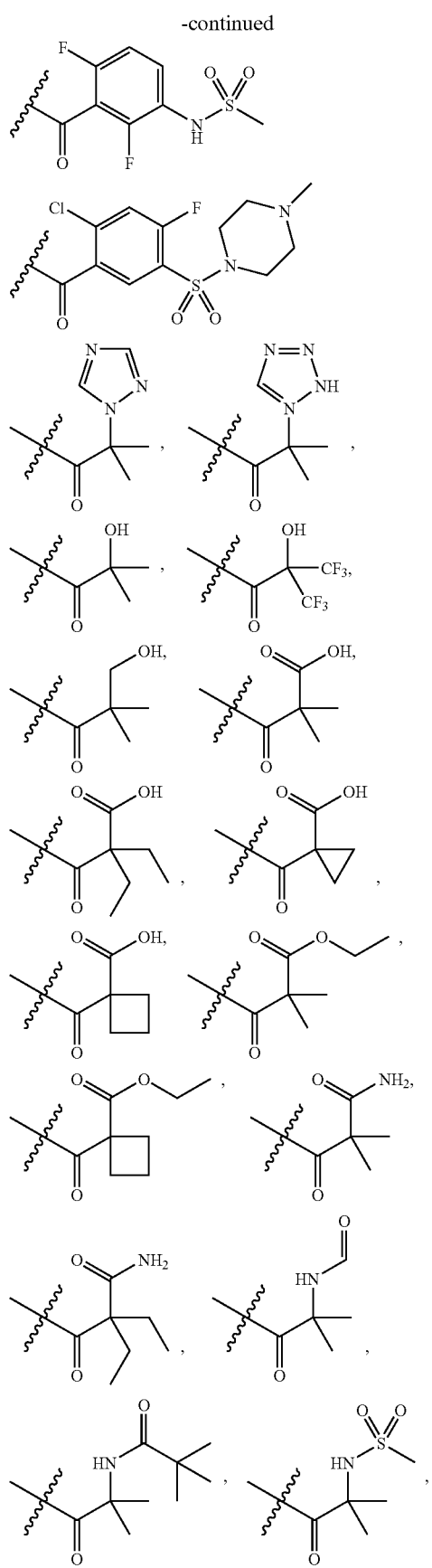
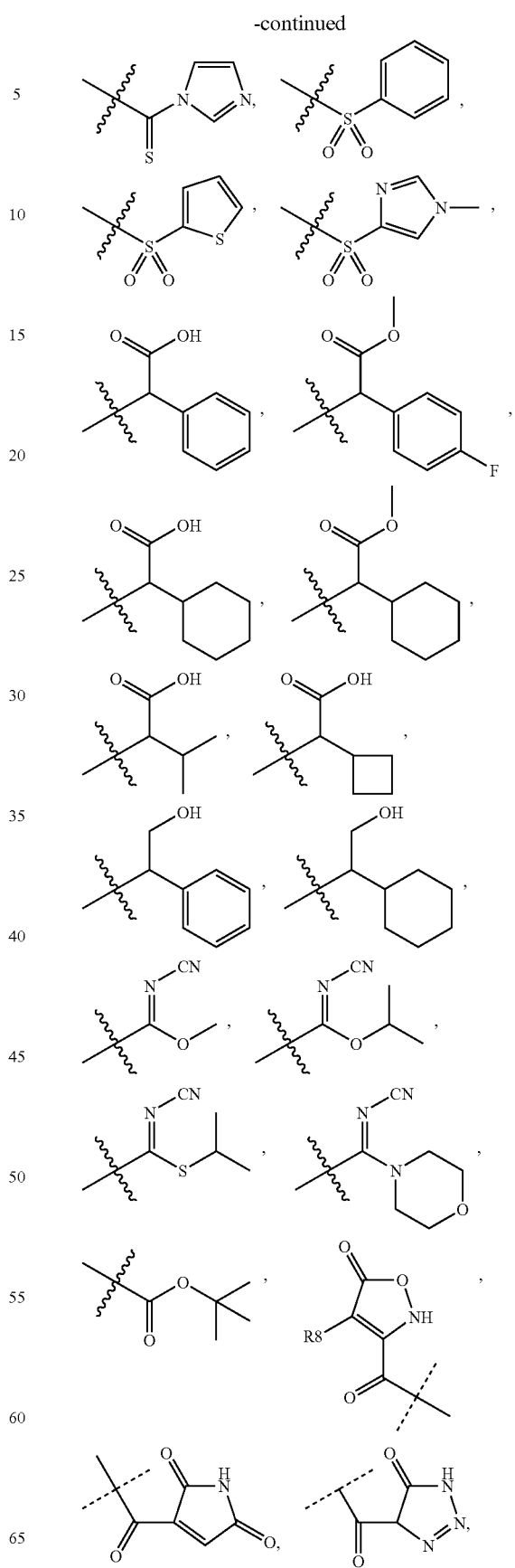

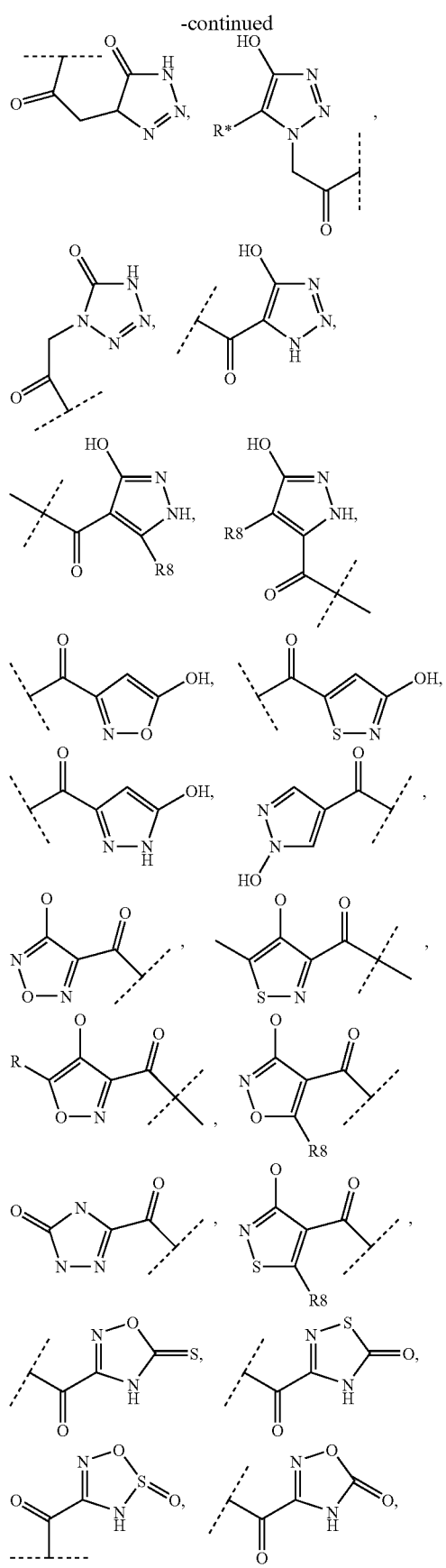
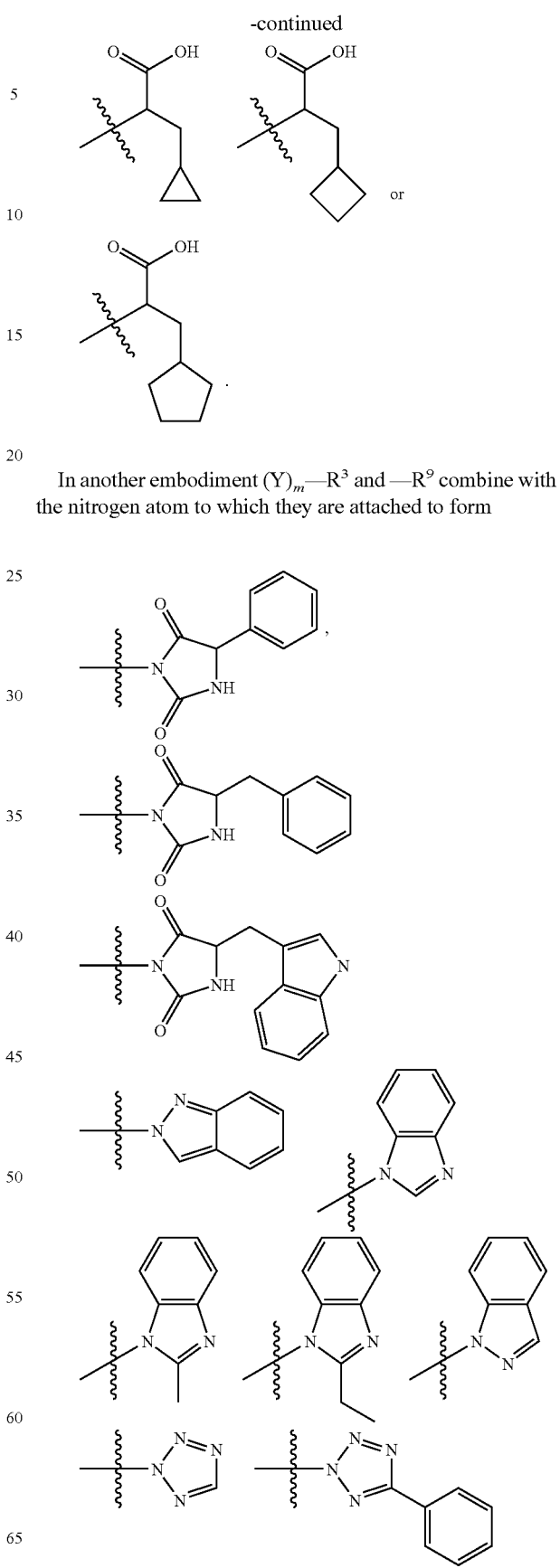
In another embodiment $(Y)_m$—$R^3$ and —$R^9$ combine with the nitrogen atom to which they are attached to form -continued

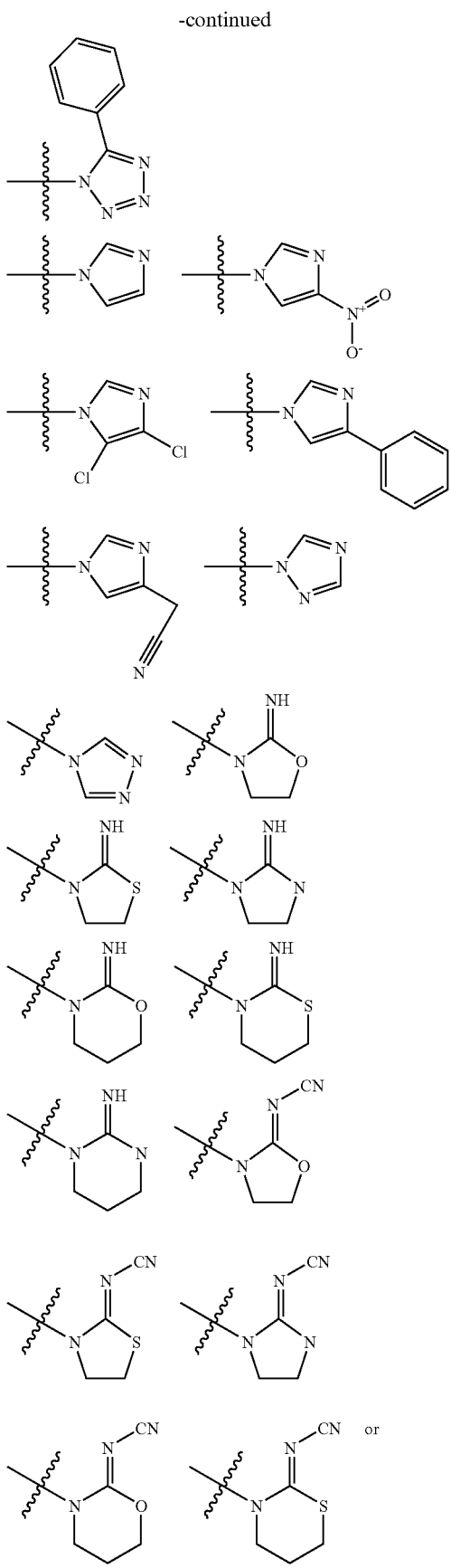

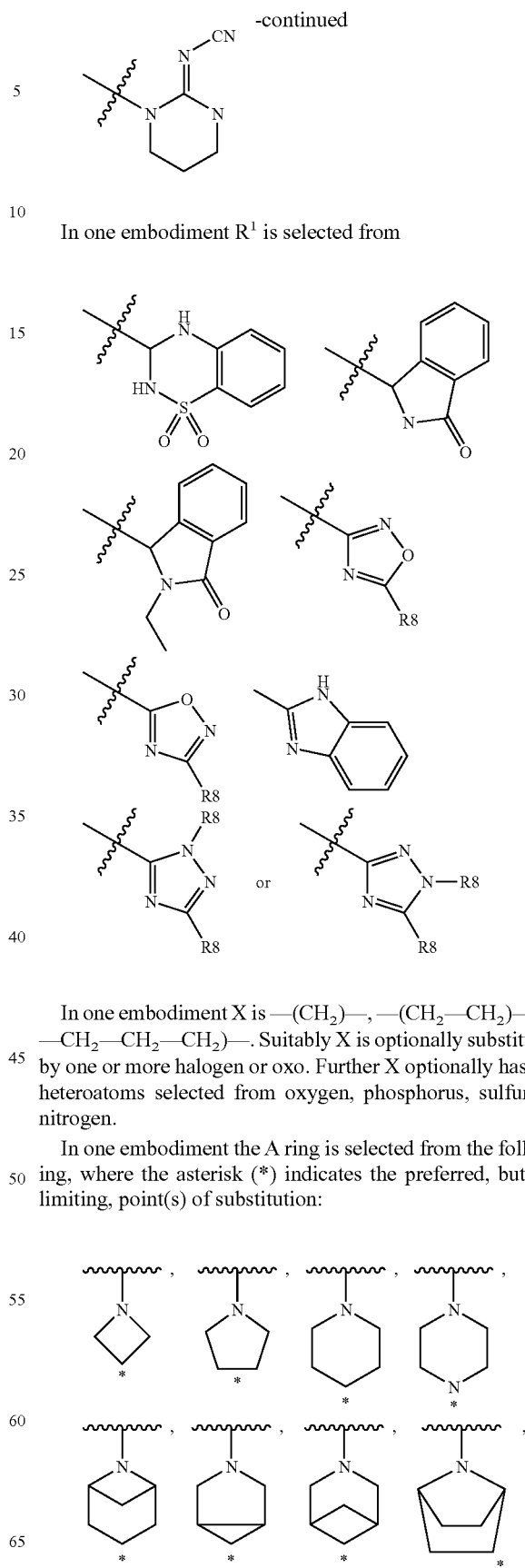

In one embodiment $R^1$ is selected from

In one embodiment X is —(CH$_2$)—, —(CH$_2$—CH$_2$)—, or —CH$_2$—CH$_2$—CH$_2$—. Suitably X is optionally substituted by one or more halogen or oxo. Further X optionally has 1-3 heteroatoms selected from oxygen, phosphorus, sulfur, or nitrogen.

In one embodiment the A ring is selected from the following, where the asterisk (*) indicates the preferred, but not limiting, point(s) of substitution:

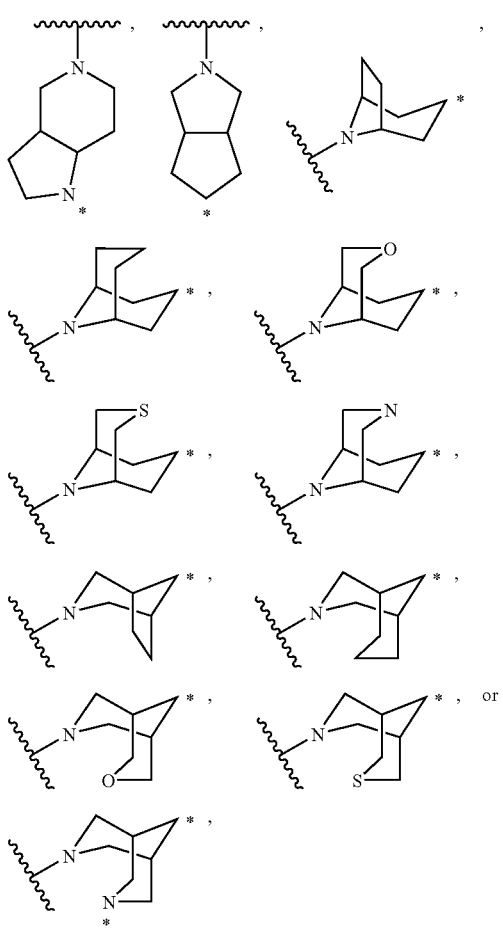
Suitably each R², with the asterisk (*) indicating a preferred, but not limiting, point of substitution from Ring A, independently is selected from
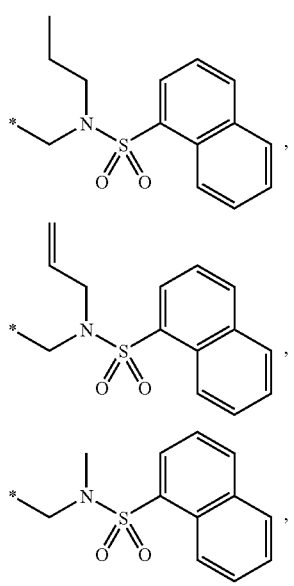
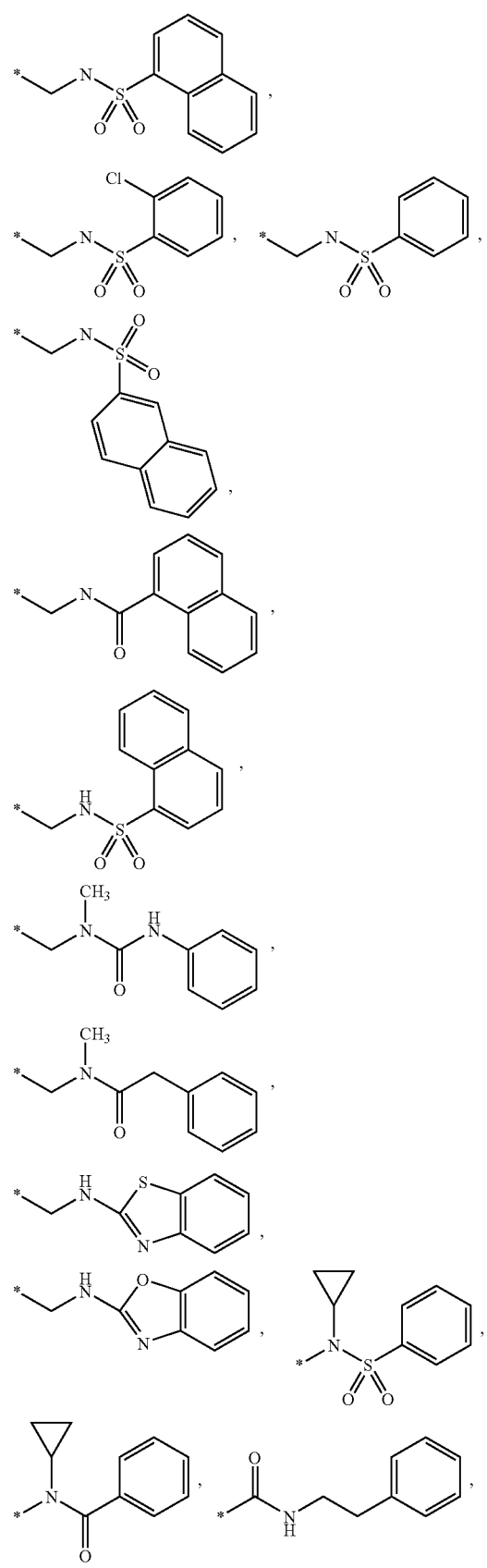

-continued
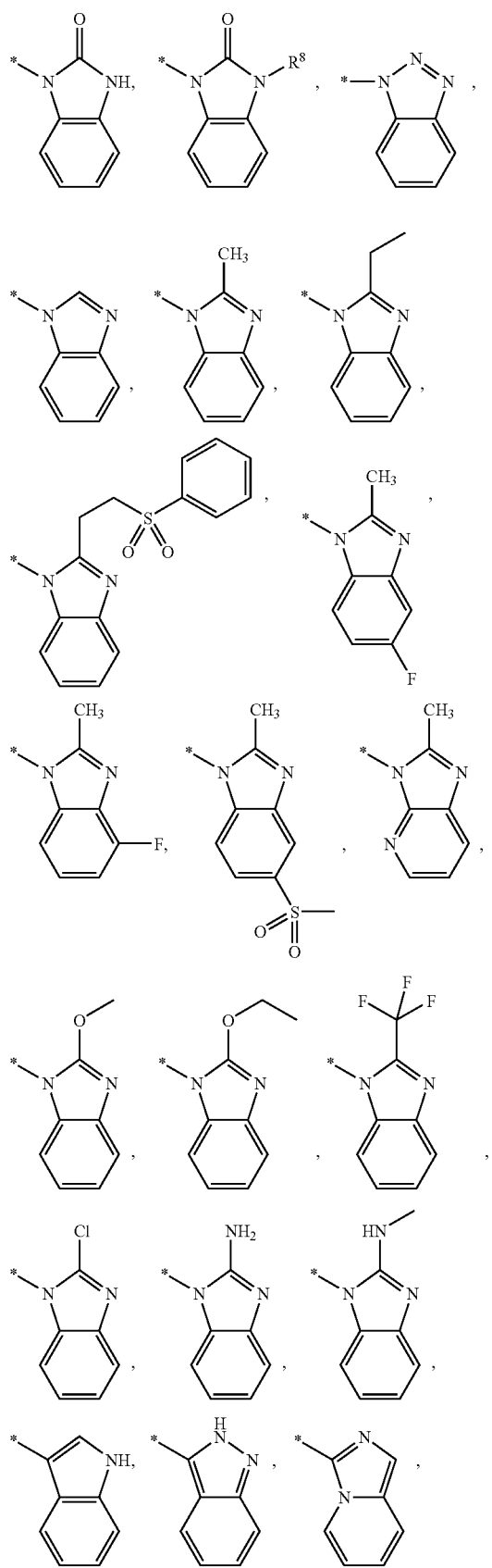
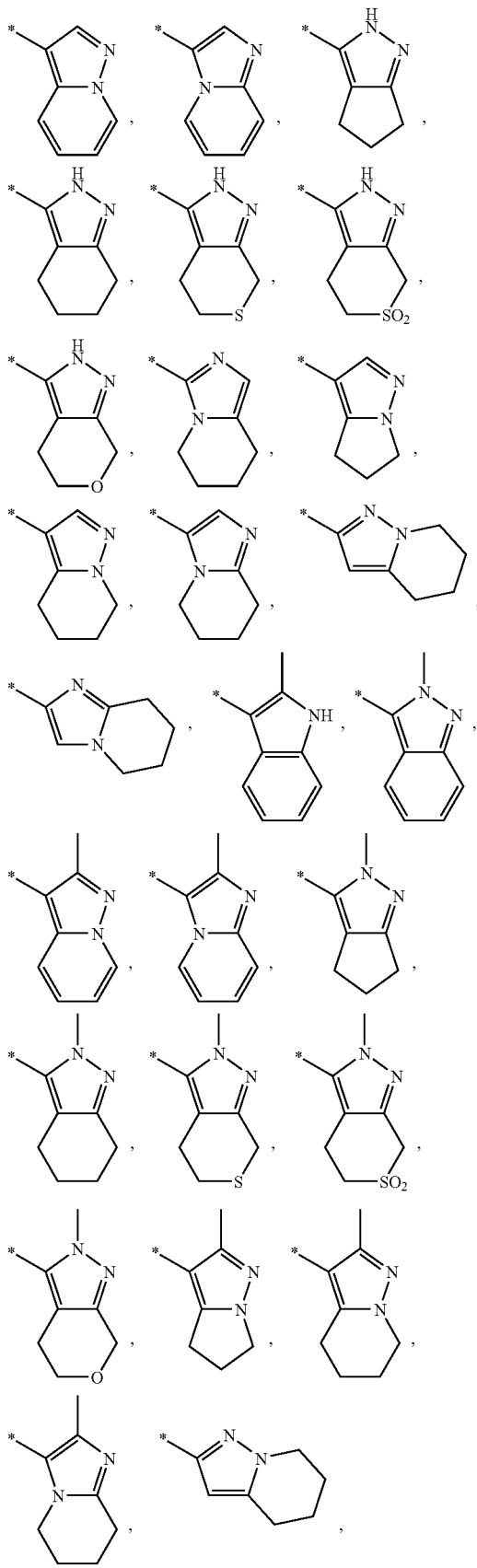

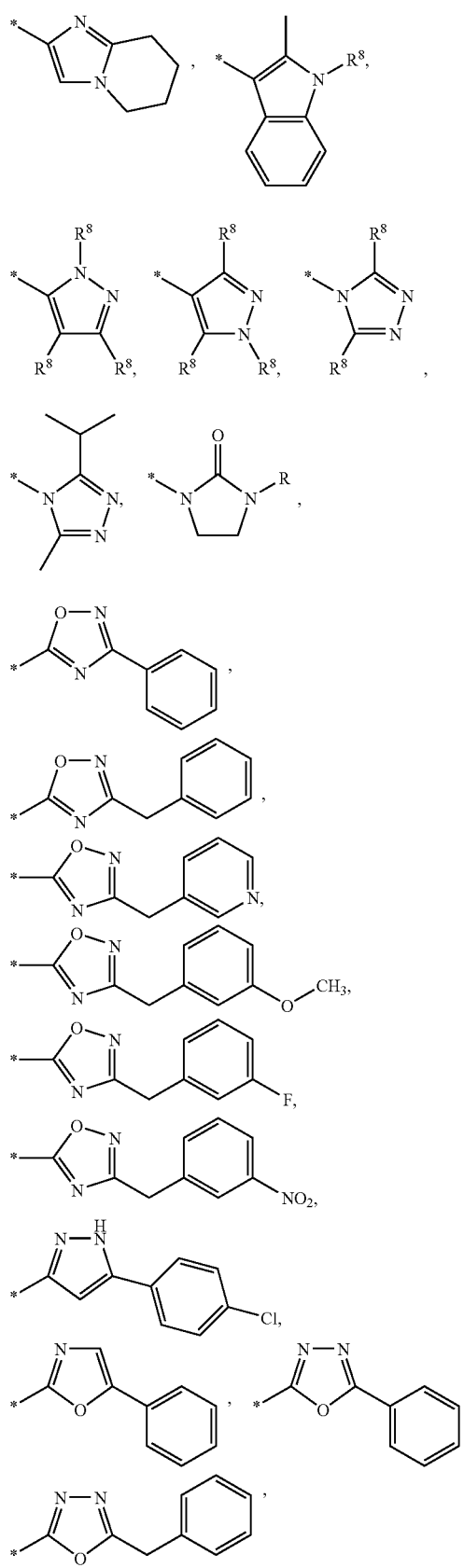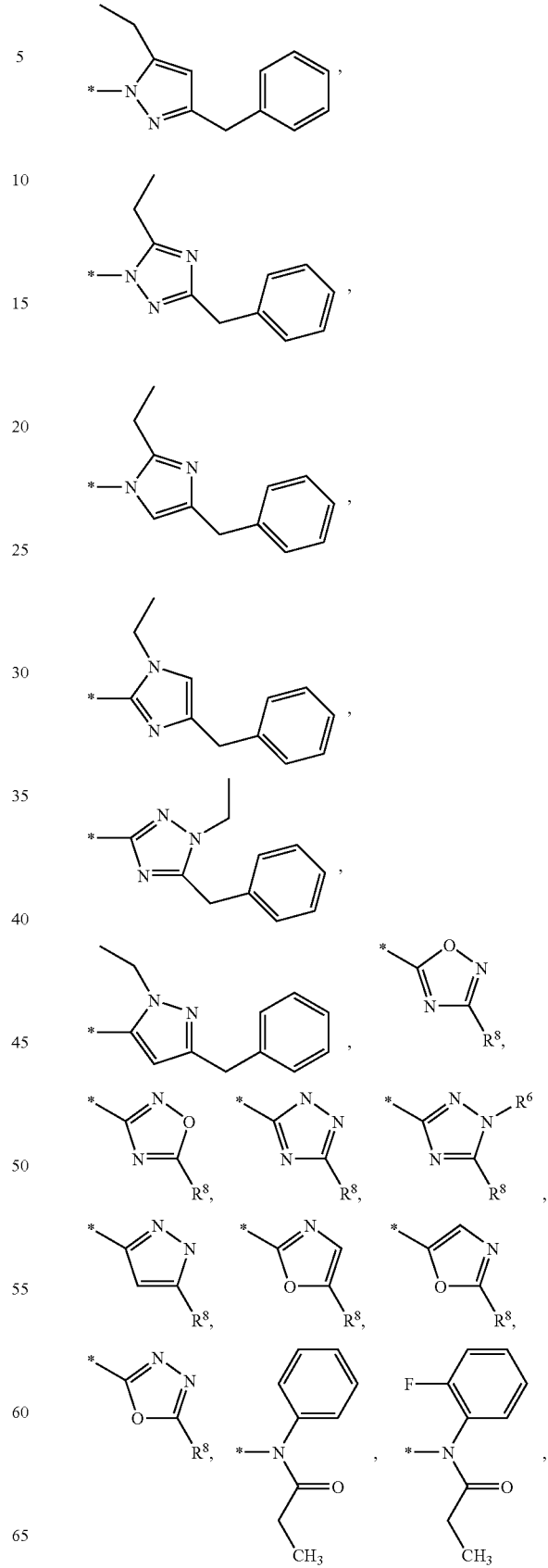

-continued
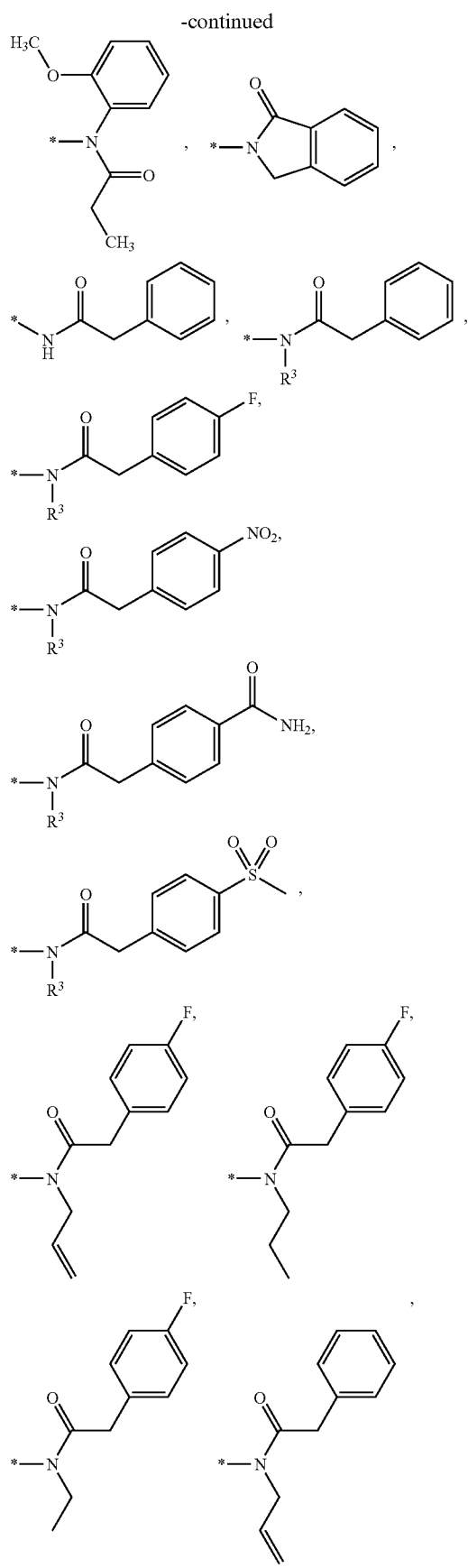
-continued
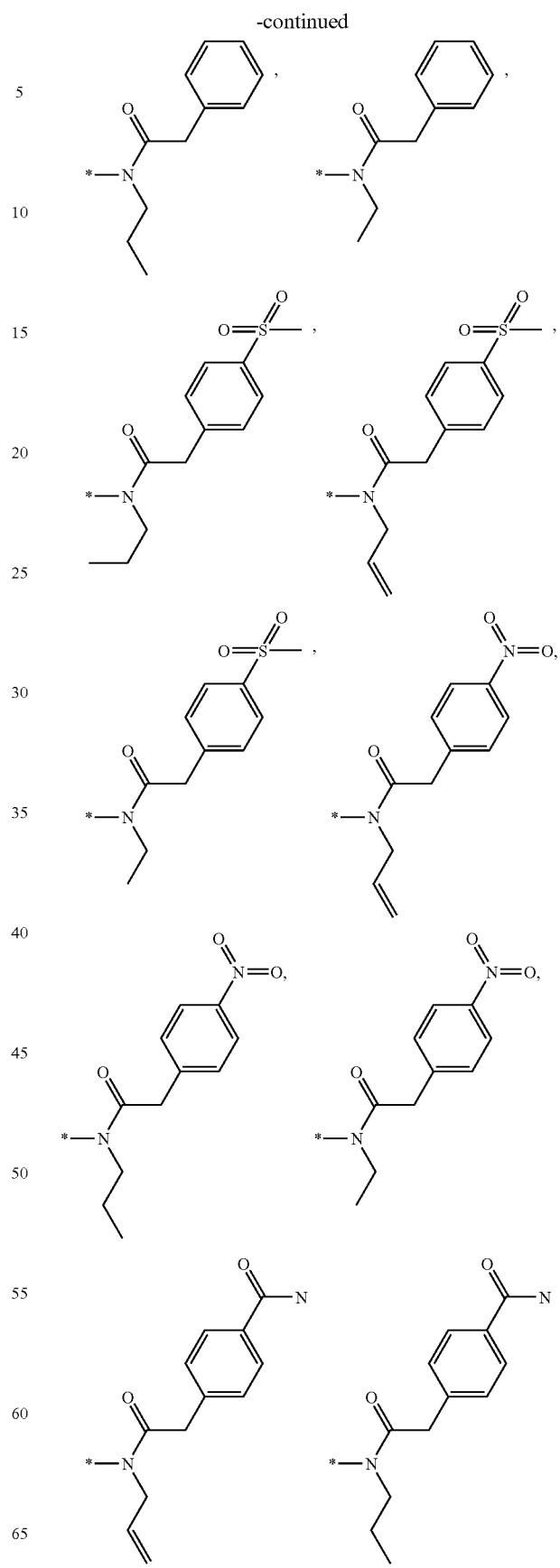

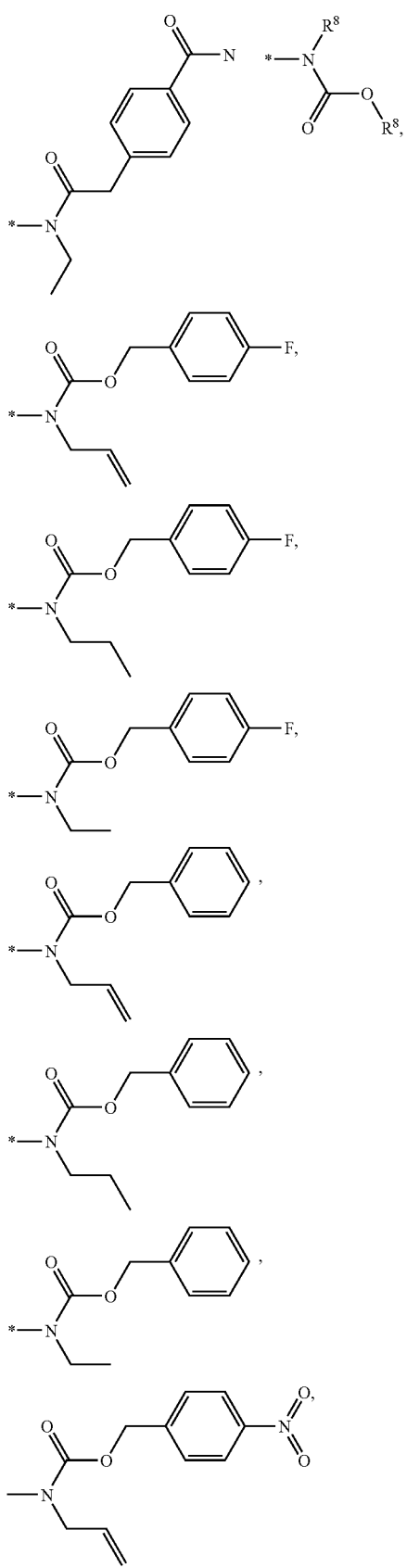
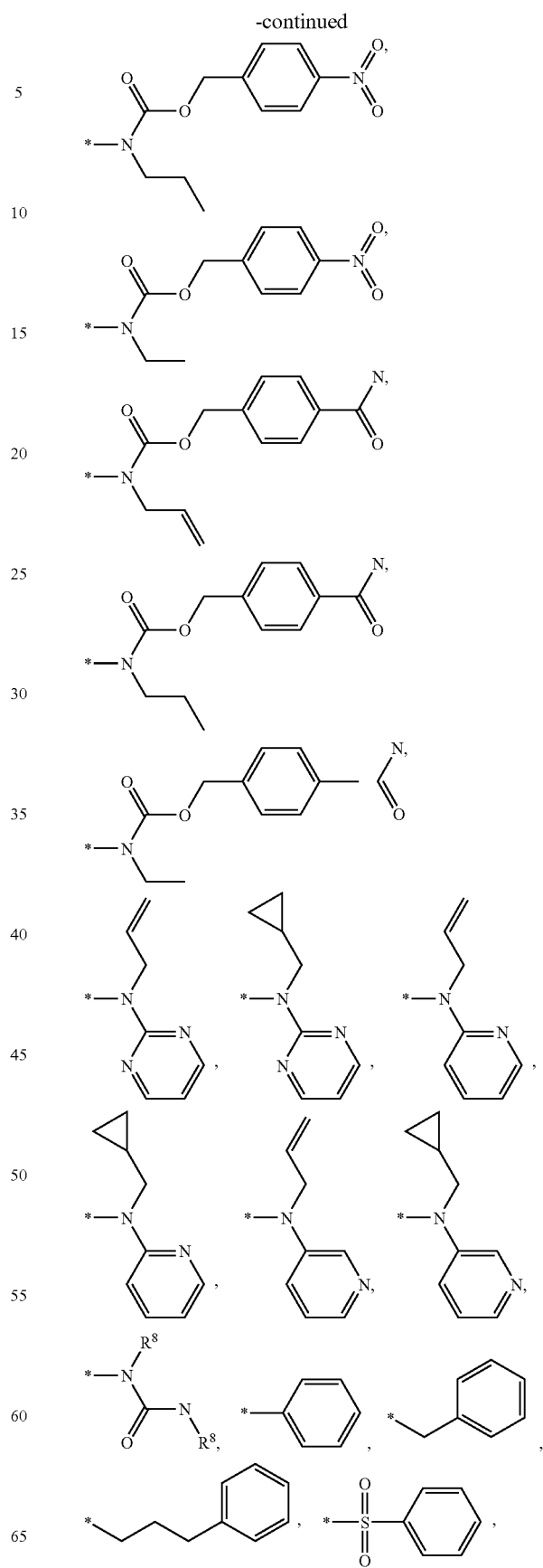

-continued
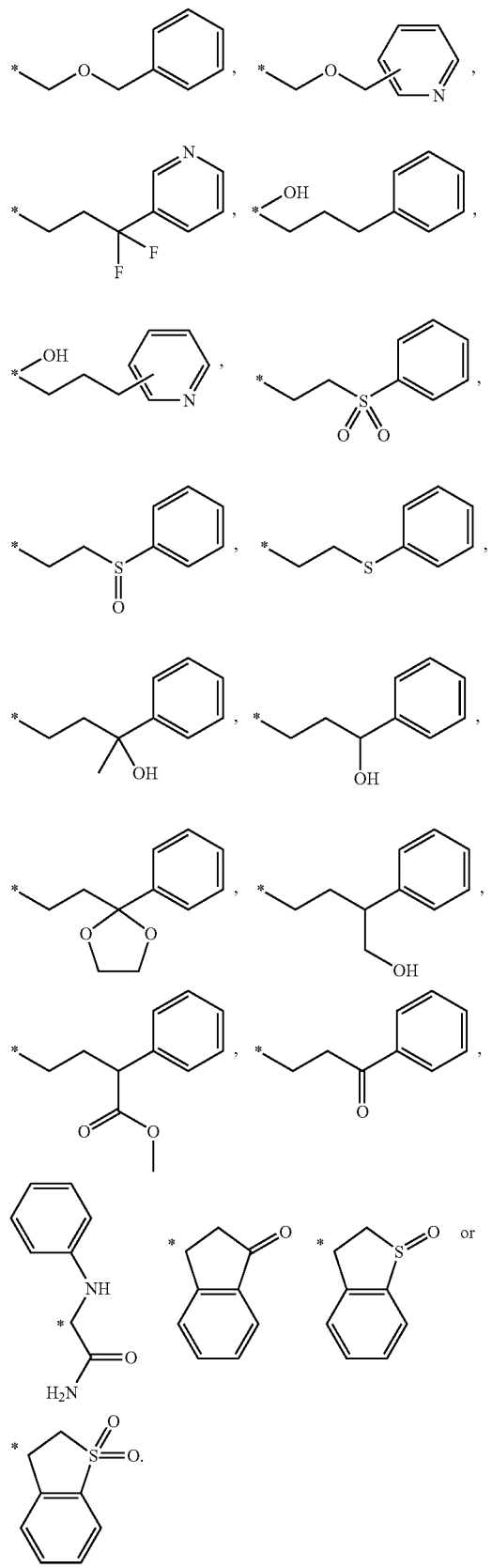
In one embodiment the ring A, with two geminal $R^2$s, is selected from:
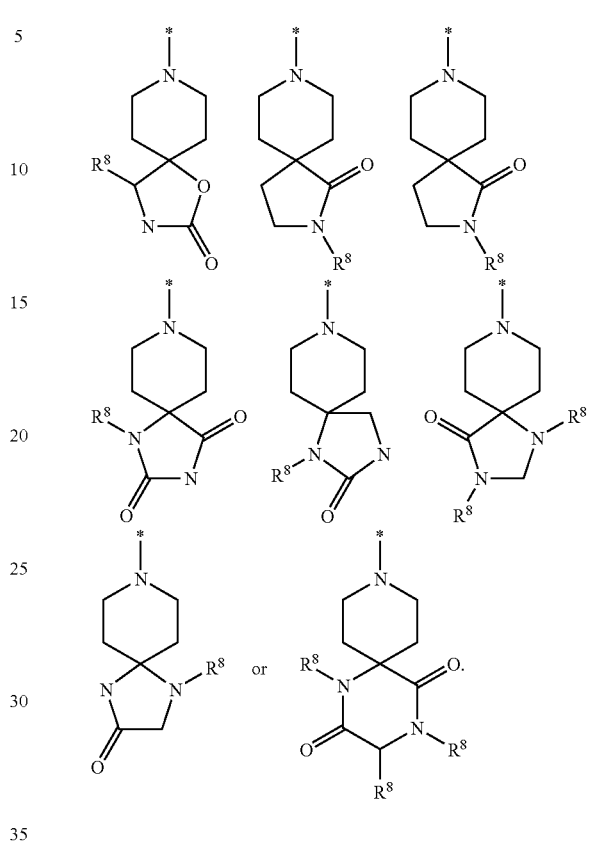
Suitably the A ring is tropane or piperidine, either optionally substituted with one or more $R^2$. Preferably, the A ring in combination with $R^2$ is comprised of one of the following:
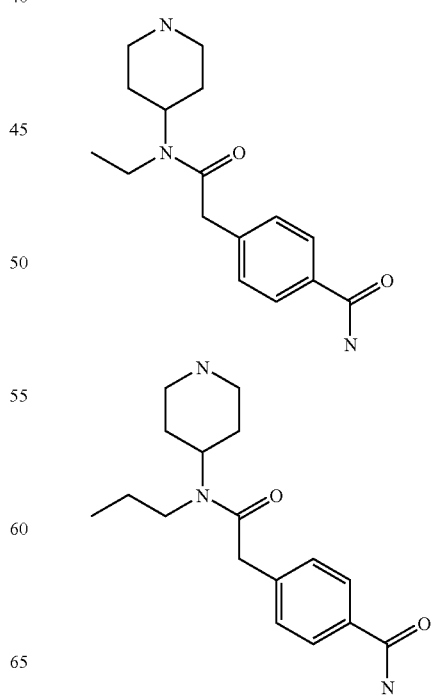

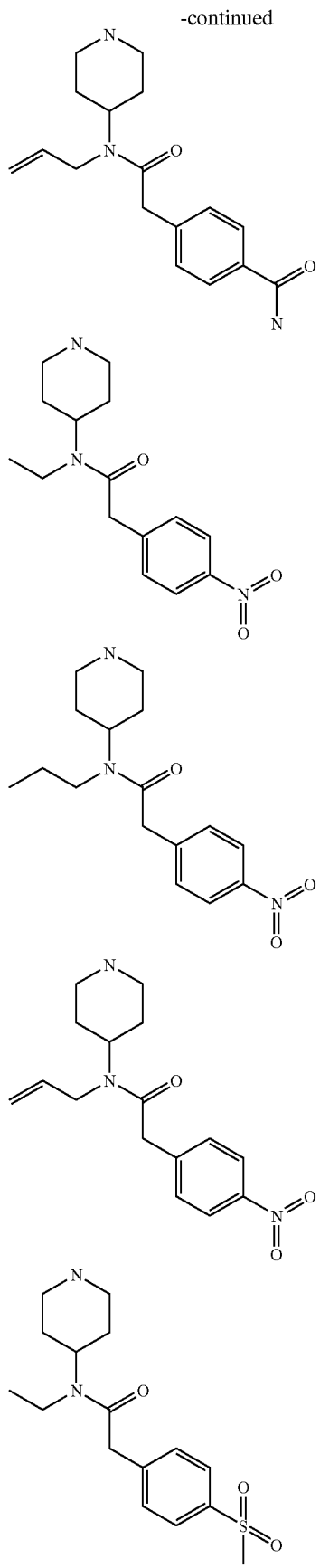
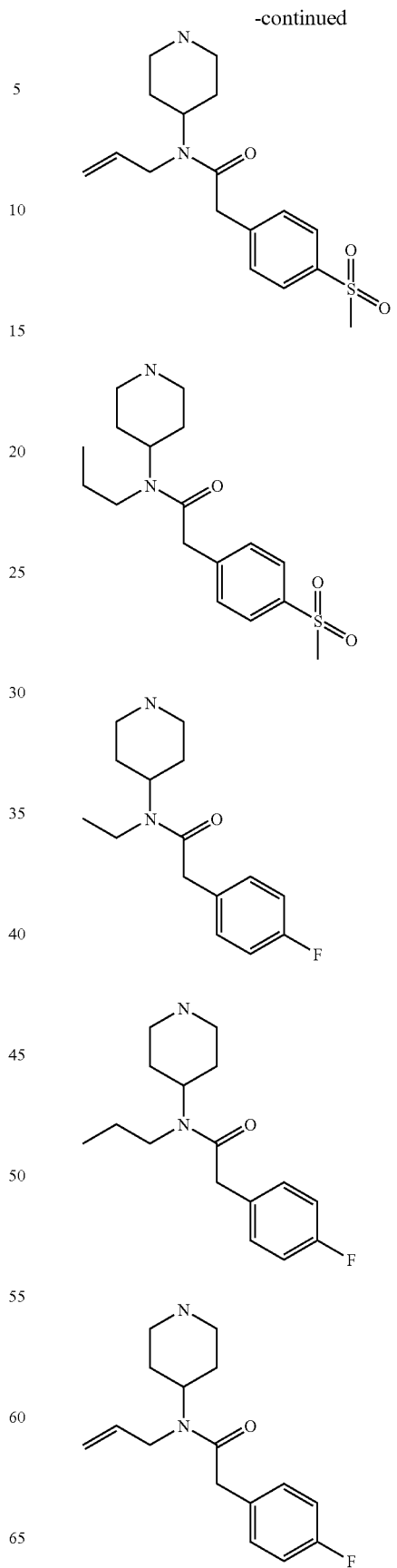

-continued
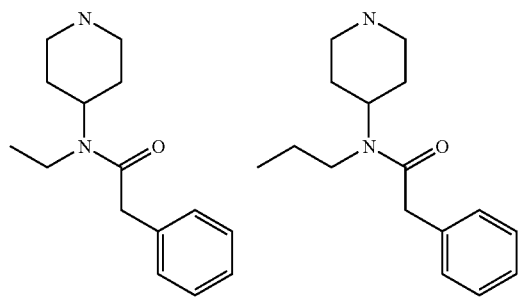
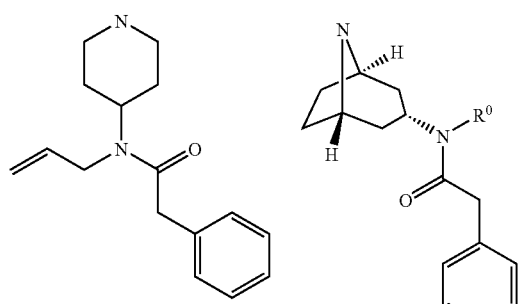
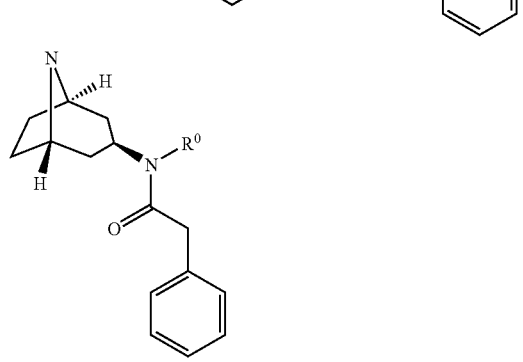
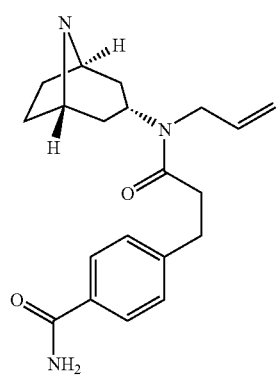
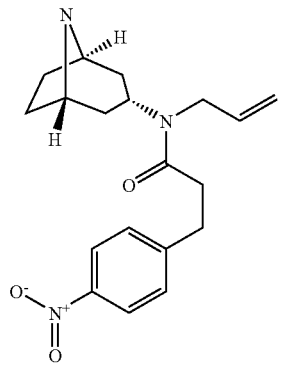
-continued
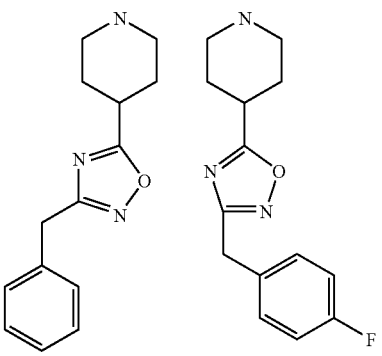
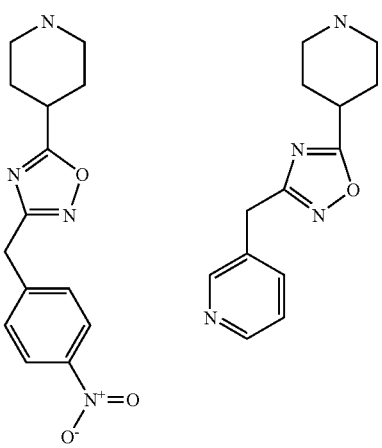
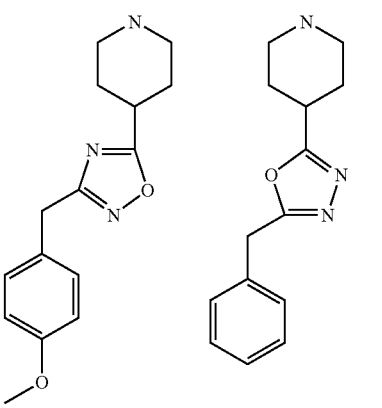
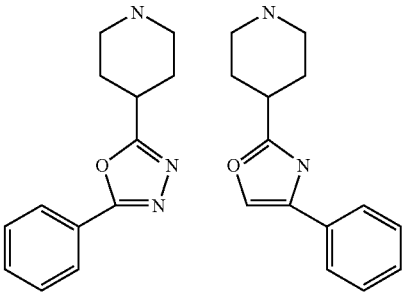

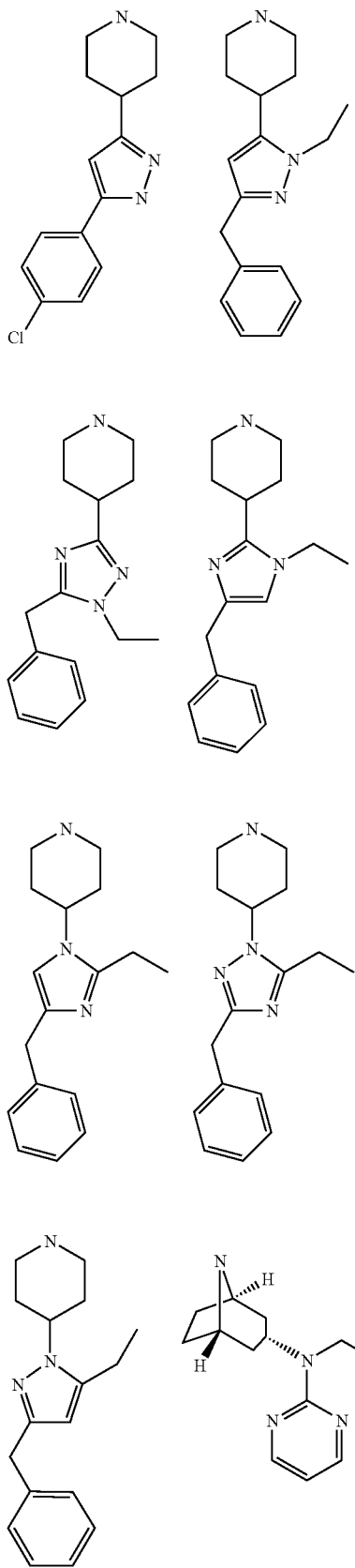
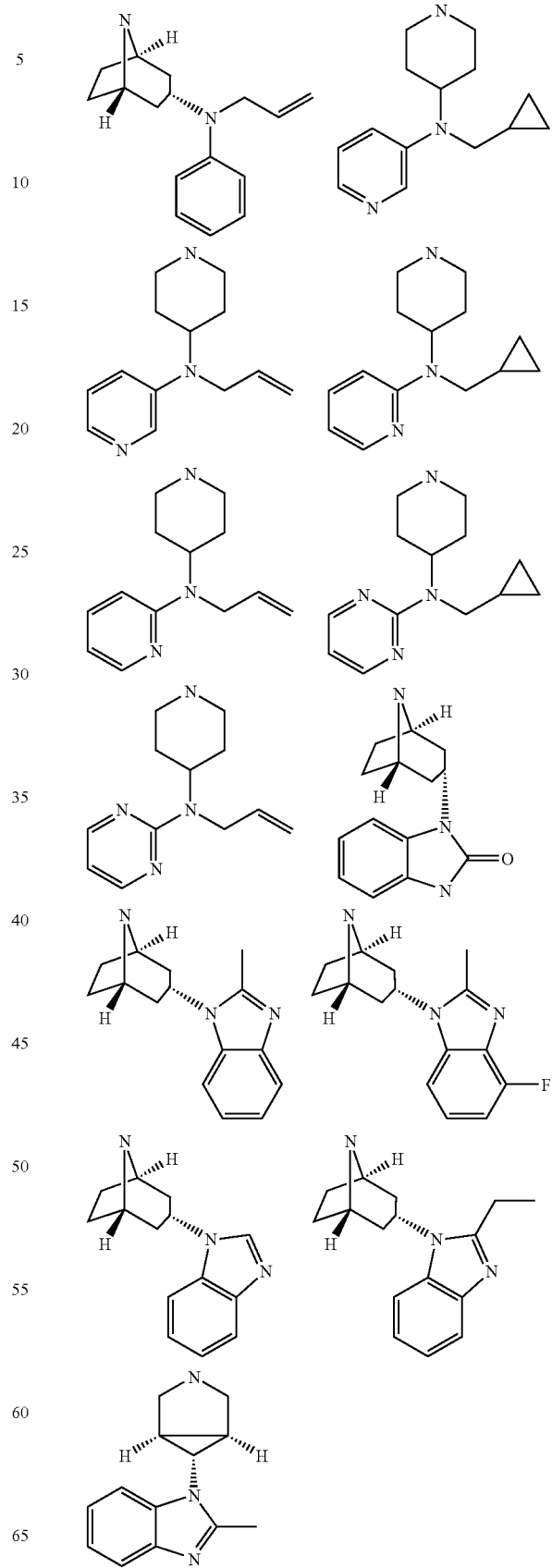

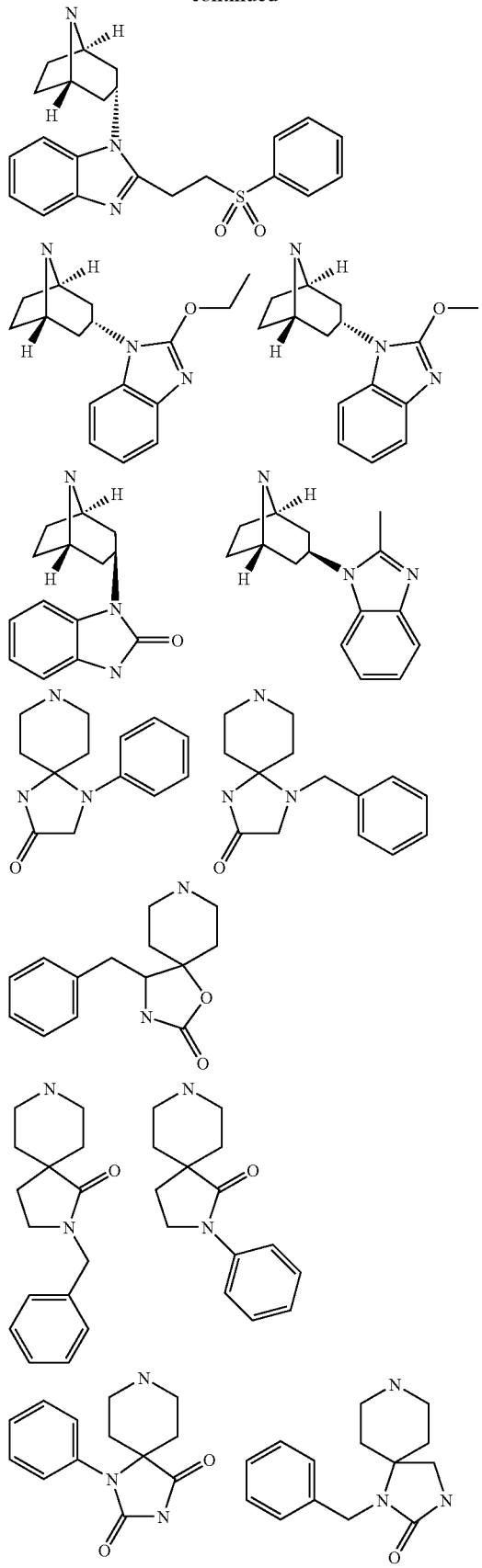
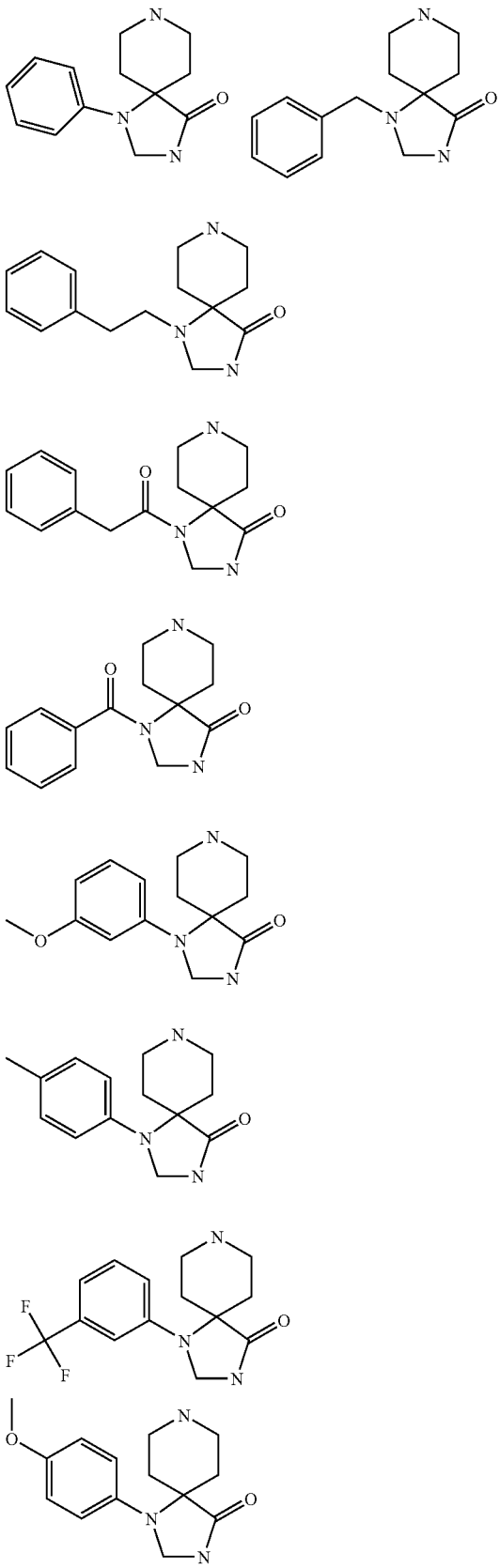

-continued
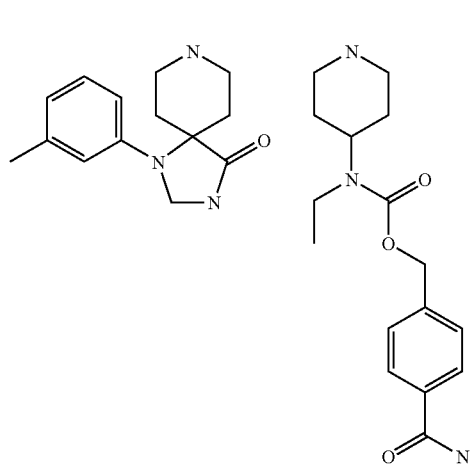
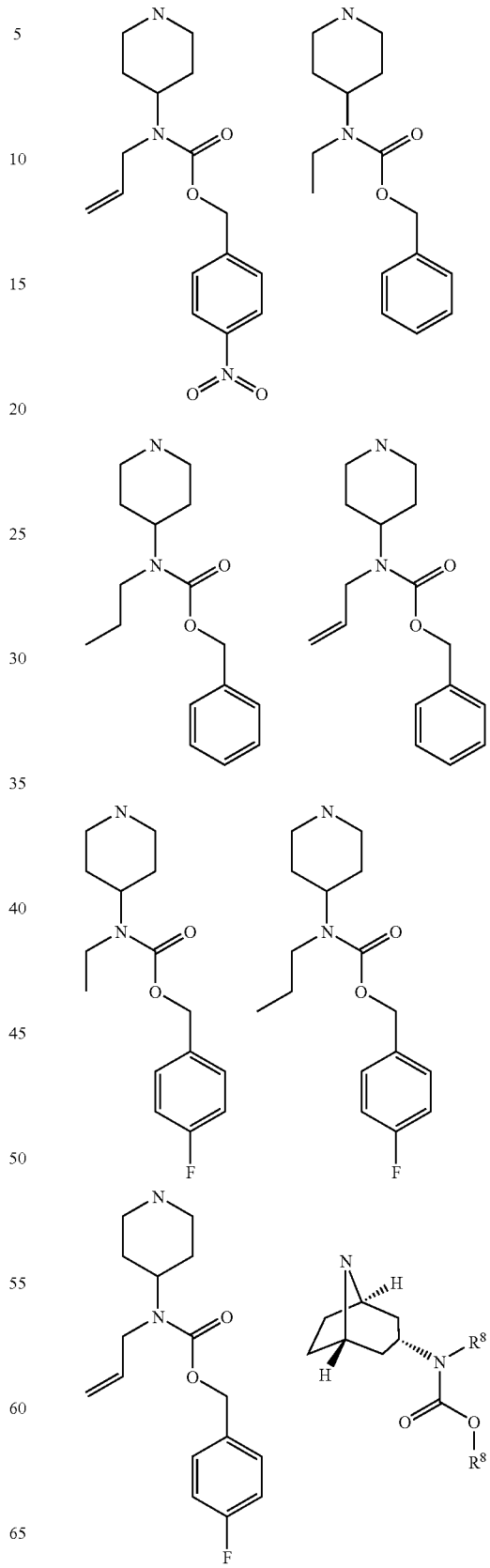

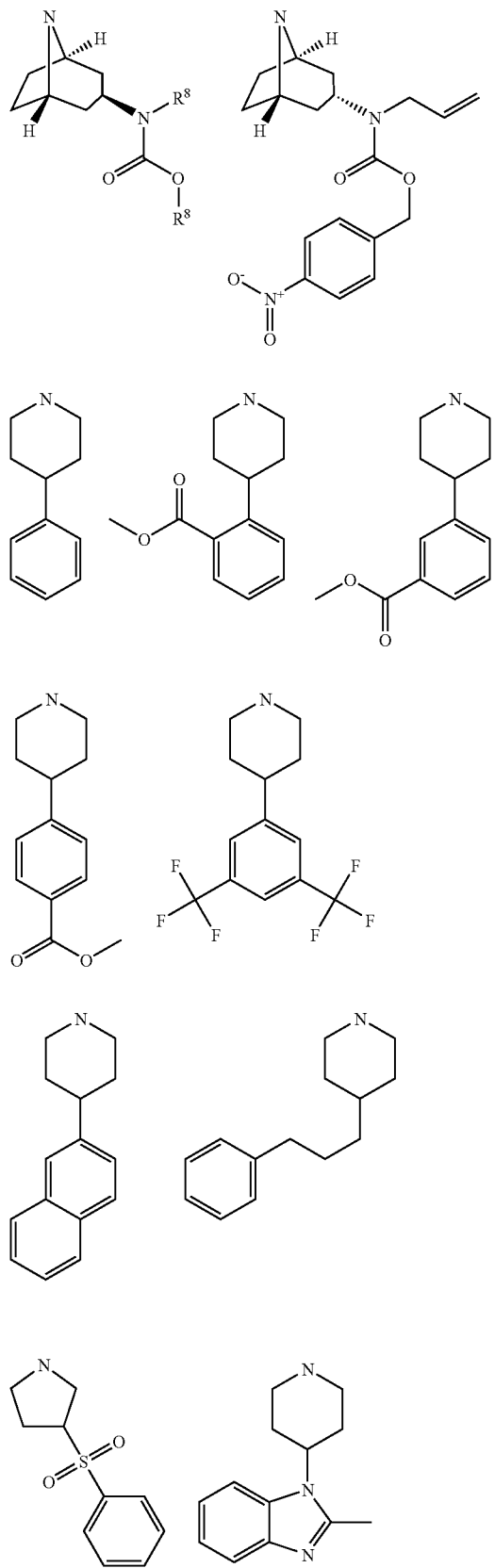
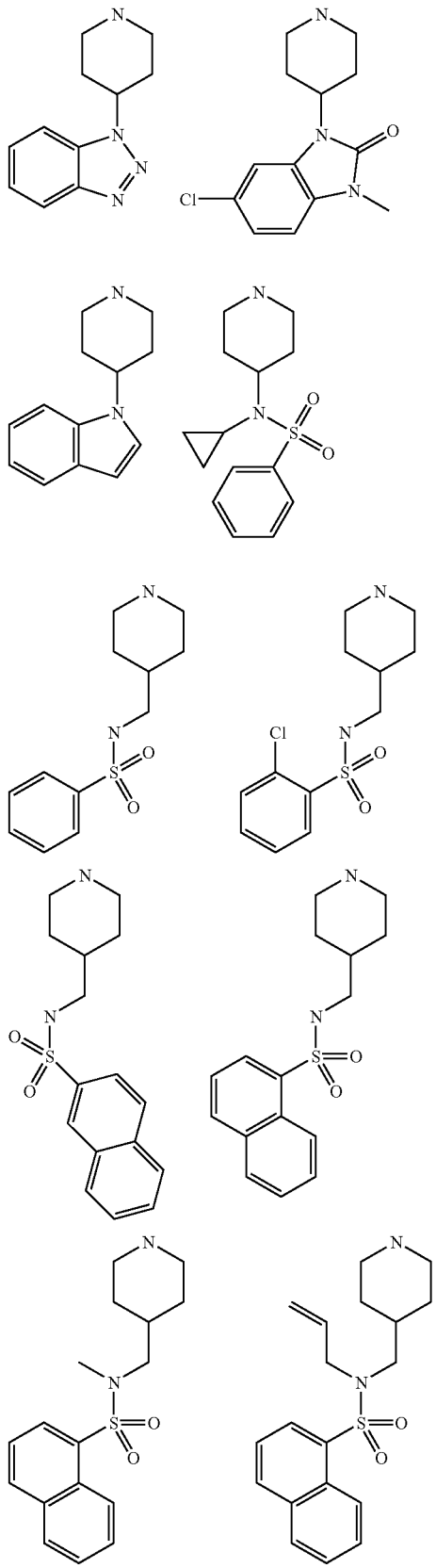

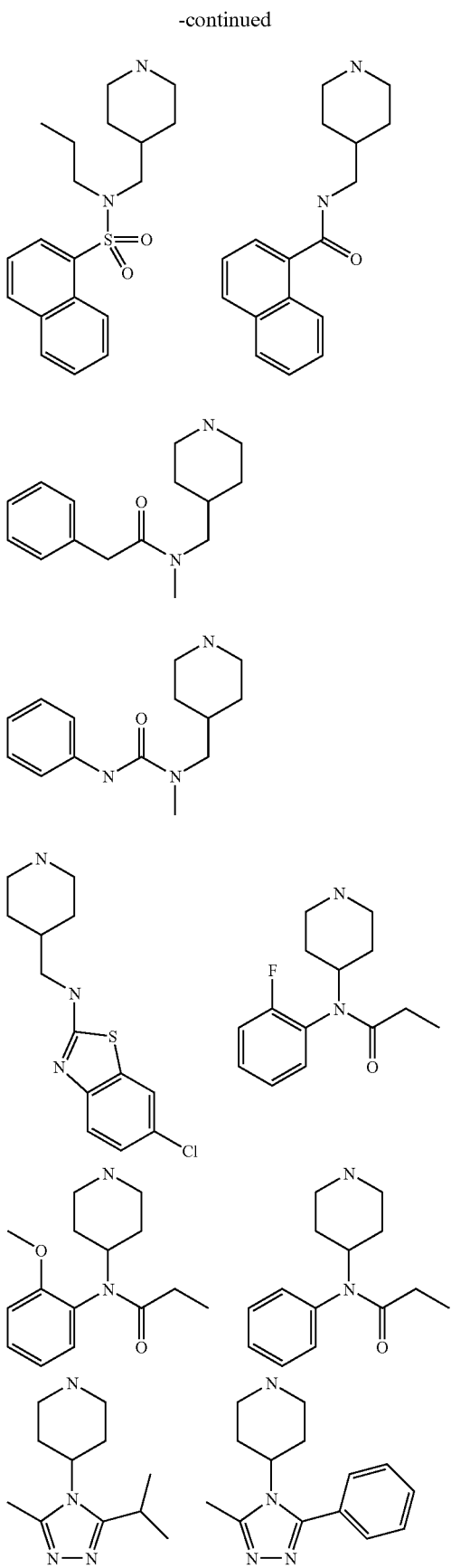

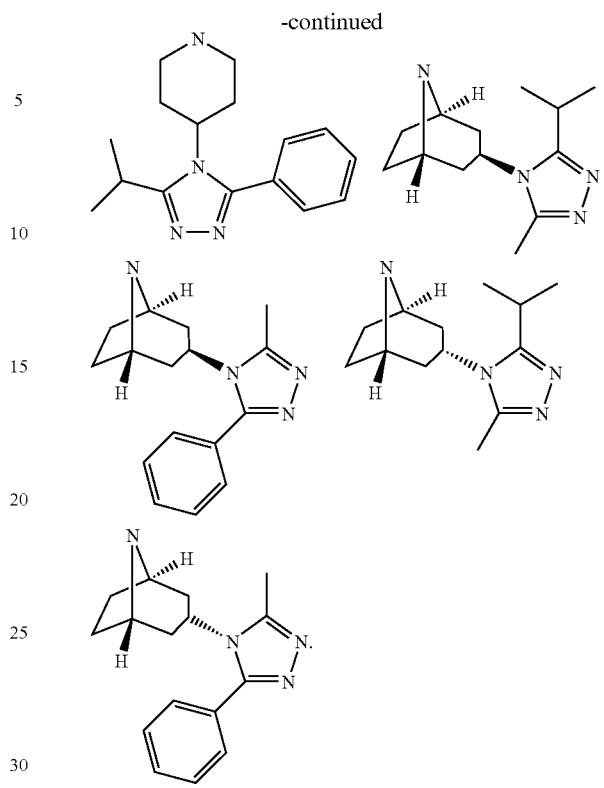

In one embodiment the A ring contains at least one additional nitrogen atom and said A ring optionally is N-substituted. Suitably the A ring is N-substituted with —(CH$_2$)$_a$—(V$_b$—R+).

One aspect of the present invention includes the compound of formula (I):

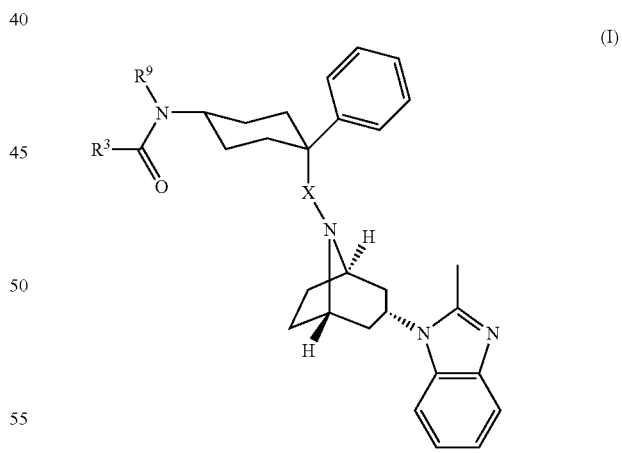

(I)

wherein X is a C$_2$-C$_3$ alkylene chain and R$^3$ and R$^9$ are each as herein defined.

One aspect of the invention provides a method of treatment (including prevention) of a viral infection in a mammal comprising administering to said mammal an antiviral effective amount of a compound of the present invention. Preferably the viral infection is an HIV infection.

One aspect of the invention provides a method of treatment (including prevention) of a bacterial infection in a mammal comprising administering to said mammal an effective amount of a compound of the present invention. Preferably the bacterium is *Yersinia pestis*.

One aspect of the invention provides a method of treatment (including prevention) of multiple sclerosis, rheumatoid arthritis, autoimmune diabetes, chronic implant rejection, asthma, rheumatoid arthritis, Crohns Disease, inflammatory bowel disease, chronic inflammatory disease, glomerular disease, nephrotoxic serum nephritis, kidney disease, Alzheimer's Disease, autoimmune encephalomyelitis, arterial thrombosis, allergic rhinitis, arteriosclerosis, Sjogren's syndrome (dermatomyositis), systemic lupus erythematosus, graft rejection, cancers with leukocyte infiltration of the skin or organs, infectious disorders including bubonic and pneumonic plague, human papilloma virus infection, prostate cancer, wound healing, amyotrophic lateral sclerosis and immune mediated disorders in a mammal comprising administering to said mammal a pharmaceutically effective amount of a compound of the present invention.

One aspect of the invention includes a compound of the present invention for use in medical therapy.

One aspect of the invention includes the use of a compound of the present invention in the manufacture of a medicament for the treatment including prophylaxis of a viral infection. Preferably the viral infection is a HIV infection.

One aspect of the invention includes the use of a compound of the present invention in the manufacture of a medicament for the treatment including prophylaxis of a bacterial infection. Preferably the bacterium is *Yersinia pestis*.

One aspect of the invention includes the use of a compound of the present invention in the manufacture of a medicament for the treatment including prophylaaxis of multiple sclerosis, rheumatoid arthritis, autoimmune diabetes, chronic implant rejection, asthma, rheumatoid arthritis, Crohns Disease, inflammatory bowel disease, chronic inflammatory disease, glomerular disease, nephrotoxic serum nephritis, kidney disease, Alzheimer's Disease, autoimmune encephalomyelitis, arterial thrombosis, allergic rhinitis, arteriosclerosis, Sjogren's syndrome (dermatomyositis), systemic lupus erythematosus, graft rejection, cancers with leukocyte infiltration of the skin or organs, infectious disorders including bubonic and pneumonic plague, human papilloma virus infection, prostate cancer, wound healing, amyotrophic lateral sclerosis and immune mediated disorders.

One aspect of the invention includes a pharmaceutical composition comprising a pharmaceutically effective amount of a compound of the present invention together with a pharmaceutically acceptable carrier. Preferably the pharmaceutical composition is in the form of a tablet, capsule, or liquid.

One aspect of the invention includes a method of treatment (including prevention) of a viral infection in a mammal comprising administering to said mammal a composition comprising a compound of the present invention and another therapeutic agent. Preferably the composition includes another therapeutic agent selected from the group consisting of (1-alpha, 2-beta, 3-alpha)-9-[2,3-bis(hydroxymethyl)cyclobutyl]guanine [(−)BHCG, SQ-34514, lobucavir], 9-[(2R, 3R,4S)-3,4-bis(hydroxymethyl)-2-oxetanosyl]adenine (oxetanocin-G), acyclic nucleosides, acyclovir, valaciclovir, famciclovir, ganciclovir, penciclovir, acyclic nucleoside phosphonates, (S)-1-(3-hydroxy-2-phosphonyl-methoxypropyl)cytosine (HPMPC), [[[2-(6-amino-9H-purin-9-yl) ethoxy]methyl]phosphinylidene]bis(oxymethylene)-2,2-dimethylpropanoic acid (bis-POM PMEA, adefovir dipivoxil), [[(1R)-2-(6-amino-9H-purin-9-yl)-1-methylethoxy]methyl]phosphonic acid (tenofovir), (R)-[[2-(6-Amino-9H-purin-9-yl)-1-methylethoxy]methyl]phosphonic acid bis-(isopropoxycarbonyloxymethyl)ester (bis-POC-PMPA), ribonucleotide reductase inhibitors, 2-acetylpyridine 5-[(2-chloroanilino)thiocarbonyl) thiocarbonohydrazone and hydroxyurea, nucleoside reverse transcriptase inhibitors, 3'-azido-3'-deoxythymidine (AZT, zidovudine), 2',3'-dideoxycytidine (ddC, zalcitabine), 2',3'-dideoxyadenosine, 2',3'-dideoxyinosine (ddI, didanosine), 2',3'-didehydrothymidine (d4T, stavudine), (−)-beta-D-2,6-diaminopurine dioxolane (DAPD), 3'-azido-2',3'-dideoxythymidine-5'-H-phosphophonate (phosphonovir), 2'-deoxy-5-iodo-uridine (idoxuridine), (−)-cis-1-(2-hydroxymethyl)-1,3-oxathiolane 5-yl)-cytosine (lamivudine), cis-1-(2-(hydroxymethyl)-1,3-oxathiolan-5-yl)-5-fluorocytosine (FTC), 3'-deoxy-3'-fluorothymidine, 5-chloro-2',3'-dideoxy-3'-fluorouridine, (−)-cis-[2-amino-6-(cyclopropylamino)-9H-purin-9-yl]-2-cyclopentene-1-methanol (abacavir), 9-[4 hydroxy-2-(hydroxymethyl)but-1-yQ-guanine (H2G), ABT-606 (2HM-H2G) ribavirin, protease inhibitors, indinavir, ritonavir, nelfinavir, amprenavir, saquinavir, fosamprenavir, (R)-N-tert-butyl-3-[(2S,3S)-2-hydroxy-3N-[(R-2-N-(isoquinolin-5-yloxyacetyl)amino-3-methylthiopropanoyl]amino-phenylbutanoyl]-5,5-dimethyl-1,3-thiazolidinecarboxamide (KNI-272), 4R-(4alpha,5alpha,6beta)]-1,3-bis[(3-aminophenyl)methyl]hexahydro-5,6-dihydroxy-4,7-bis(phenylmethyl)-2H-1,3-diazepin-2-one dimethanesulfonate (mozenavir), 3-[1-[3-[2-(5-trifluoromethylpyridinyl)-sulfonylamino]phenyl]propyl]-4-hydroxy-6alpha-phenethyl-6beta-propyl-5,6-dihydro-2-pyranone (tipranavir), N'-[2(S)-Hydroxy-3(S)-[N-(methoxycarbonyl)-l-tert-leucylamino]4-phenylbutyl-N alpha-(methoxycarbonyl)-N'-[4-(2-pyridyl) benzyl]-L-tert-leucylhydrazide (BMS-232632), 3-(2(S)-Hydroxy-3(S)-(3-hydroxy-2-methylbenzamido)-4-phenylbutanoyl)-5,5-dimethyl-N-(2-methylbenzyl) thiazolidine-4(R)-carboxamide (AG-1776), N-(2(R)-hydroxy-1 (S)-indanyl)-2(R)-phenyl-methyl-4(S)-hydroxy-5-(1-(1-(4-benzo[b]furanylmethyl)-2(S)-N'-(tert-butylcarboxamido)piperazinyl)pentanamide (MK-944A), interferons, α-interferon, renal excretion inhibitors, probenecid, nucleoside transport inhibitors, dipyridamole, pentoxifylline, N-acetylcysteine (NAC), Procysteine, α-trichosanthin, phosphonoformic acid, immunomodulators, interleukin II, thymosin, granulocyte macrophage colony stimulating factors, erythropoetin, soluble $CD_4$ and genetically engineered derivatives thereof, non-nucleoside reverse transcriptase inhibitors (NNRTIs), nevirapine (BI-RG-587), alpha-((2-acetyl-5-methylphenyl)amino)-2,6-dichloro-benzeneacetamide (loviride), 1-[3-(isopropylamino)-2-pyridyl]-4-[5-(methanesulfonamido)-1H-indol-2-ylcarbonyl]piperazine monomethanesulfonate (delavirdine), (10R,11S,12S)-12-hydroxy-6,6,10,11-tetramethyl-4-propyl-11,12-dihydro-2H, 6H, 10H-benzo(1,2-b:3,4-b':5,6-b")tripyran-2-one ((+) calanolide A), (4S)-6-Chloro-4-[1E)-cyclopropylethenyl)-3,4-dihydro-4-(trifluoromethyl)-2(1H)-quinazolinone (DPC-083), (S)-6-chloro-4-(cyclopropylethynyl)-1,4-dihydro-4-(trifluoromethyl)-2H-3,1-benzoxazin-2-one (efavirenz, DMP 266), 1-(ethoxymethyl)-5-(1-methylethyl)-6-(phenylmethyl)-2,4(1H,3H)-pyrimidinedione (MKC-442), and 5 (3,5-dichlorophenyl)thio-4-isopropyl-1-(4-pyridyl)methyl-1H-imidazol-2-ylmethyl carbamate (capravirine), glycoprotein 120 antagonists, PRO-2000, PRO-542, 1,4-bis[3-[(2,4-dichlorophenyl)carbonylamino]-2-oxo-5,8-disodiumsulfanyl]naphthalyl-2,5-dimethoxyphenyl-1,4-dihydrazone (FP-21399), cytokine antagonists, reticulose (Product-R), 1,1'-azobis-formamide (ADA), 1,11-(1,4-phenylenebis(methylene))bis-1,4,8,11-tetraazacyclotetradecane octahydrochloride (AMD-3100), integrase inhibitors, and fusion inhibitors.

One aspect of the invention includes a method of treatment (including prevention) of a viral infection in a mammal comprising administering to said mammal a composition comprising a compound of the present invention and ritonavir.

DETAILED DESCRIPTION OF THE INVENTION

The phrase "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

The term "alkyl", alone or in combination with any other term, refers to a straight-chain or branched-chain saturated aliphatic hydrocarbon radical containing the specified number of carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "cycloalkyl", "carbocylyl", "carbocyclic", or "carbocycle", or "carbocyclo", alone or in combination with any other term, refers to a monocyclic or polycyclic non-aromatic hydrocarbon ring radical having three to twenty carbon atoms, preferably from three to twelve carbon atoms, and more preferably from three to ten carbon atoms. If polycyclic, each ring in a carbocylyl radical is non-aromatic unless otherwise indicated. A carbocylyl radical is either completely saturated or contains one or more units of unsaturation but is not aromatic. The unsaturation, if present, may occur in any point in the ring that may result in any chemically stable configuration. The term "cycloalkyl", "carbocylyl", "carbocyclic", or "carbocycle", or "carbocyclo" also includes hydrocarbon rings that are fused to one or more aromatic rings, such as in tetrahydronaphthyl, where the radical or point of attachment is on the non-aromatic ring.

Unless otherwise indicated, the term "cycloalkyl", "carbocylyl", "carbocyclic", or "carbocycle", or "carbocyclo" also includes each possible positional isomer of a non-aromatic hydrocarbon radical, such as in 1-decahydronaphthyl, 2-decahydronaphthyl, 1-tetrahydronaphthyl and 2-tetrahydronaphthyl. Examples of suitable cycloalkyl groups include, but are not limited to, cyclopropyl, cyclobutyl, cyclopentyl, cyclohexyl, cyclohexenyl, decahydronaphthyl, tetrahydronaphthyl and the like.

The term "alkenyl," alone or in combination with any other term, refers to a straight-chain or branched-chain alkyl group with at least one carbon-carbon double bond. Examples of alkenyl radicals include, but are not limited to, ethenyl, propenyl, isopropenyl, butenyl, isobutenyl, pentenyl, hexenyl, hexadienyl and the like.

The term "alkynyl" refers to hydrocarbon groups of either a straight or branched configuration with one or more carbon-carbon triple bonds which may occur in any stable point along the chain, such as ethynyl, propynyl, butynyl, pentynyl, and the like.

The term "alkoxy" refers to an alkyl ether radical, wherein the term "alkyl" is defined above. Examples of suitable alkyl ether radicals include, but are not limited to, methoxy, ethoxy, n-propoxy, isopropoxy, n-butoxy, isobutoxy, sec-butoxy, tert-butoxy and the like.

The term "aryl", alone or in combination with any other term, refers to an aromatic monocyclic or polycyclic hydrocarbon ring radical containing five to twenty carbon atoms, preferably from six to fourteen carbon atoms, and more preferably from six to ten carbon atoms. Also included within the scope of the term "aryl", as it is used herein, is a group in which an aromatic hydrocarbon ring is fused to one or more non-aromatic carbocyclic or heteroatom-containing rings, such as in an indanyl, phenanthridinyl or tetrahydronaphthyl, where the radical or point of attachment is on the aromatic hydrocarbon ring.

Unless otherwise indicated, the term "aryl" also includes each possible positional isomer of an aromatic hydrocarbon radical, such as in 1-naphthyl, 2-naphthyl, 5-tetrahydronaphthyl, 6-tetrahydronaphthyl, 1-phenanthridinyl, 2-phenanthridinyl, 3-phenanthridinyl, 4-phenanthridinyl, 7-phenanthridinyl, 8-phenanthridinyl, 9-phenanthridinyl and 10-phenanthridinyl. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like.

The term "aralkyl" further refers to groups of —$R_aR_b$, where $R_a$ is an alkylene as defined herein and $R_b$ is an aryl as defined herein.

The term "heterocycle", "heterocyclic", and "heterocyclyl", alone or in combination with any other term, refers to a non-aromatic monocyclic or polycyclic ring radical containing three to twenty carbon atoms, preferably three to seven carbon atoms if monocyclic and eight to eleven carbon atoms if bicyclic, and in which one or more ring carbons, preferably one to four, are each replaced by a heteroatom such as N, O, and S. If polycyclic, each ring in a heterocyclyl radical is non-aromatic unless otherwise indicated. A heterocyclic ring may be fully saturated or may contain one or more units of unsaturation but is not aromatic. The unsaturation, if present, may occur in any point in the ring that may result in any chemically stable configuration. The heterocyclic ring may be attached at a carbon or heteroatom that results in the creation of a stable structure. Preferred heterocycles include 5-7 membered monocyclic heterocyles and 8-10 membered bicyclic heterocycles.

Also included within the scope of the term "heterocycle", "heterocyclic", or "heterocyclyl" is a group in which a non-aromatic heteroatom-containing ring is fused to one or more aromatic rings, such as in an indolinyl, chromanyl, phenanthridinyl or tetrahydroquinolinyl, where the radical or point of attachment is on the non-aromatic heteroatom-containing ring. Unless otherwise indicated, the term "heterocycle", "heterocyclic", or "heterocyclyl" also includes each possible positional isomer of a heterocyclic radical, such as in 1-decahydroquinoline, 2-decahydroquinoline, 3-decahydroquinoline, 4-decahydroquinoline, 5-decahydroquinoline, 6-decahydroquinoline, 7-decahydroquinoline, 7-decahydroquinoline, 8-decahydroquinoline, 4a-decahydroquinoline, 8a-decahydroquinoline, 1-indolinyl, 2-indolinyl, 3-indolinyl, 1-tetrahydroquinoline, 2-tetrahydroquinoline, 3-tetrahydroquinoline and 4-tetrahydroquinoline. The term "heterocyclylalkyl" refers to an alkyl group substituted by a heterocyclyl.

Examples of heterocyclic groups include, but are not limited to, imidazolinyl, 2,3-dihydro-1H-imidazolyl, imidazolidinyl, indazolinolyl, perhydropyridazyl, pyrrolinyl, pyrrolidinyl, 4H-pyrazolyl, piperidinyl, pyranyl, pyrazolinyl, piperazinyl, morpholinyl, thiamorpholinyl, thiazolidinyl, thiamorpholinyl, oxopiperidinyl, oxopyrrolidinyl, azepinyl, tetrahydrofuranyl, oxoazepinyl, tetrahydropyranyl, thiazolyl, dioxolyl, dioxinyl, oxathiolyl, benzodioxolyl, dithiolyl, dithiolanyl, tetrahydrothiophenyl, sulfolanyl, dioxanyl, dioxolanyl, tetahydrofurodihydrofuranyl, dihydropyranyl, tetrahydropyranodihydrofuranyl, tetradyrofurofuranyl, tetrahydropyranofuranyl, diazolonyl, phthalimidinyl, benzoxanyl, benzopyrrolidinyl, benzopiperidinyl, benzoxolanyl, benzothiolanyl and benzothianyl.

The term "heteroaryl", alone or in combination with any other term, refers to an aromatic monocyclic or polycyclic ring radical containing five to twenty carbon atoms, preferably five to ten carbon atoms, in which one or more ring carbons, preferably one to four, are each replaced by a heteroatom such as N, O, and S. Preferred heteroaryl groups include 5-6 membered monocyclic heteroaryls and 8-10 membered bicyclic heteroaryls.

Also included within the scope of the term "heteroaryl" is a group in which a heteroaromatic ring is fused to one or more aromatic or non-aromatic rings where the radical or point of attachment is on the heteroaromatic ring. Examples include, but are not limited to, pyrido[3,4-d]pyrimidinyl, 7,8-dihydro-pyrido[3,4-d]pyrimidine and 5,6,7,8-tetrahydro-pyrido[3,4-d]pyrimidine. Unless otherwise indicated, the term "heteroaryl" also includes each possible positional isomer of a heteroaryl radical, such as in 2-pyrido[3,4-d]pyrimidinyl and 4-pyrido[3,4-d]pyrimidinyl.

Examples of heteroaryl groups include, but are not limited to, imidazolyl, quinolyl, isoquinolyl, indolyl, indazolyl, pyridazyl, pyridyl, pyrrolyl, pyrazolyl, pyrazinyl, quinoxalyl, pyrimidinyl, pyridazinyl, furyl, thienyl, triazolyl, thiazolyl, carbazolyl, carbolinyl, tetrazolyl, benzofuranyl, oxazolyl, benzoxazolyl, isoxozolyl, isothiazolyl, thiadiazolyl, furazanyl, oxadiazolyl, benzimidazolyl, benzothienyl, quinolinyl, benzotriazolyl, benzothiazolyl, isoquinolinyl, isoindolyl, acridinyl and benzoisoxazolyl.

The term "heteroaralkyl" further refers to groups of —R$^a$R$^b$, where R$^a$ is an alkylene as defined herein and R$^b$ is a heteroaryl as defined herein.

The term "heteroatom" means nitrogen, oxygen, phosphorus, or sulfur and includes any oxidized forms thereof, including as non-limiting examples oxidized forms of nitrogen such as N(O) {N$^+$—O$^-$}, oxidized forms of sulfur such as S(O) and S(O)$_2$, and the quaternized form of any basic nitrogen.

The term "halogen" refers to fluorine, chlorine, bromine or iodine.

The term "pharmaceutically effective amount" refers to an amount of a compound of the invention that is effective in treating a CCR5-related disease, for example a virus infection, for example an HIV infection, in a patient either as monotherapy or in combination with other agents. The term "treatment" as used herein refers to the alleviation of symptoms of a particular disorder in a patient, or the improvement of an ascertainable measurement associated with a particular disorder, and may include the suppression of symptom recurrence in an asymptomatic patient such as a patient in whom a viral infection has become latent. The term "prophylaxis" refers to preventing a disease or condition or preventing the occurrence of symptoms of such a disease or condition, in a patient. As used herein, the term "patient" refers to a mammal, including a human.

The term "pharmaceutically acceptable carrier" refers to a carrier that may be administered to a patient, together with a compound of this invention, and which does not destroy the pharmacological activity thereof and is nontoxic when administered in doses sufficient to deliver a therapeutic amount of the therapeutic agent.

The term "pharmaceutically acceptable derivative" means any pharmaceutically acceptable salt, ester, salt of an ester, or other derivative of a compound of this invention which, upon administration to a recipient, is capable of providing (directly or indirectly) a compound of this invention or an inhibitorily active metabolite or residue thereof. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

Pharmaceutically acceptable salts of the compounds according to the invention include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g. sodium), alkaline earth metal (e.g., magnesium), ammonium, NW$_4^+$ (wherein W is C$_{1-4}$ alkyl) and other amine salts. Physiologically acceptable salts of a hydrogen atom or an amino group include salts of organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids. Physiologically acceptable salts of a compound with a hydroxy group include the anion of said compound in combination with a suitable cation such as Na$^+$, NH$_4^+$, and NW$_4^+$ (wherein W is a C$_{1-4}$alkyl group).

Any reference to any of the above compounds also includes a reference to a pharmaceutically acceptable salt thereof.

Salts of the compounds of the present invention may be made by methods known to a person skilled in the art. For example, treatment of a compound of the present invention with an appropriate base or acid in an appropriate solvent will yield the corresponding salt.

Esters of the compounds of the present invention are independently selected from the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted by, for example, halogen, C$_{1-4}$alkyl, or C$_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a C$_{1-20}$ alcohol or reactive derivative thereof, or by a 2,3-di (C$_{6-24}$)acyl glycerol.

In such esters, unless otherwise specified, any alkyl moiety present advantageously contains from 1 to 18 carbon atoms, particularly from 1 to 6 carbon atoms, more particularly from 1 to 4 carbon atoms, Any cycloalkyl moiety present in such esters advantageously contains from 3 to 6 carbon atoms. Any aryl moiety present in such esters advantageously comprises a phenyl group.

The compounds according to the invention contain one or more asymmetric carbon atoms and thus occur as racemates and racemic mixtures, single enantiomers, diastereomeric mixtures and individual diastereoisomers. All such isomeric forms of these compounds are expressly included in the present invention. Each stereogenic carbon may be of the R or S configuration. Although the specific compounds exemplified in this application may be depicted in a particular stereochemical configuration, compounds having either the opposite stereochemistry at any given chiral center or mixtures thereof are also envisioned.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are also within the scope of this invention.

Certain compounds of this invention may exist in alternative tautomeric forms. All such tautomeric forms of the present compounds are within the scope of the invention. Unless otherwise indicated, the representation of either tautomer is meant to include the other.

The present invention features compounds according to the invention for use in medical therapy, for example for the treatment including prophylaxis of viral infections such as an HIV infections and associated conditions. Reference herein to treatment extends to prophylaxis as well as the treatment of established infections, symptoms, and associated clinical conditions such as AIDS related complex (ARC), Kaposi's sarcoma, and AIDS dementia.

The present invention features use of the compounds of the present invention in the manufacture of a medicament for the treatment including prophylaxis of a CCR5-related disease or condition, for example, a viral infection, for example, an HIV infection.

According to another aspect, the present invention provides a method for the treatment (including prevention) of the symptoms or effects of a viral infection in an infected animal, for example, a mammal including a human, which comprises treating said animal with a pharmaceutically effective amount of a compound according to the invention. According to one aspect of the invention, the viral infection is a retroviral infection, in particular an HIV infection. A further aspect of the invention includes a method for the treatment, including prevention, of the symptoms or effects of an HBV infection.

The compounds according to the invention may also be used in adjuvant therapy in the treatment of HIV infections or HIV-associated symptoms or effects, for example Kaposi's sarcoma.

The compounds of the present invention may also be used in the treatment, including prevention, of other CCR5-related diseases and conditions, including multiple sclerosis, rheumatoid arthritis, autoimmune diabetes, chronic implant rejection, asthma, rheumatoid arthritis, Crohns Disease, inflammatory bowel disease, chronic inflammatory disease, glomerular disease, nephrotoxic serum nephritis, kidney disease, Alzheimer's Disease, autoimmune encephalomyelitis, arterial thrombosis, allergic rhinitis, arteriosclerosis, Sjogren's syndrome (dermatomyositis), systemic lupus erythematosus, graft rejection, cancers with leukocyte infiltration of the skin or organs, human papilloma virus infection, prostate cancer, wound healing, amyotrophic lateral sclerosis, immune mediated disorders.

The present invention further provides a method for the treatment of a clinical condition in an animal, for example, a mammal including a human which clinical condition includes those which have been discussed hereinbefore, which comprises treating said animal with a pharmaceutically effective amount of a compound according to the invention. The present invention also includes a method for the treatment, including prophylaxis, of any of the aforementioned diseases or conditions.

In yet a further aspect, the present invention provides the use of a compound according to the invention in the manufacture of a medicament for the treatment, including prophylaxis, of any of the above mentioned viral infections or conditions.

The above compounds according to the invention and their pharmaceutically acceptable derivatives may be employed in combination with other therapeutic agents for the treatment of the above infections or conditions. Combination therapies according to the present invention comprise the administration of a compound of the present invention or a pharmaceutically acceptable derivative thereof and another pharmaceutically active agent. The active ingredient(s) and pharmaceutically active agents may be administered simultaneously in either the same or different pharmaceutical compositions or sequentially in any order. The amounts of the active ingredient(s) and pharmaceutically active agent(s) and the relative timings of administration will be selected in order to achieve the desired combined therapeutic effect.

Examples of such therapeutic agents include agents that are effective for the treatment of viral infections or associated conditions. Among these agents are (1-alpha, 2-beta, 3-alpha)-9-[2,3-bis(hydroxymethyl)cyclobutyl]guanine [(−)BHCG, SQ-34514, lobucavir], 9-[(2R,3R,4S)-3,4-bis (hydroxymethyl)-2-oxetanosyl]adenine (oxetanocin-G), acyclic nucleosides, for example acyclovir, valaciclovir, famciclovir, ganciclovir, and penciclovir, acyclic nucleoside phosphonates, for example (S)-1-(3-hydroxy-2-phosphonylmethoxypropyl)cytosine (HPMPC), [[[2-(6-amino-9H-purin-9-yl)ethoxy]methyl]phosphinylidene]bis(oxymethylene)-2,2-dimethylpropanoic acid (bis-POM PMEA, adefovir dipivoxil), [[(1R)-2-(6-amino-9H-purin-9-yl)-1-methylethoxy]methyl]phosphonic acid (tenofovir), and (R)[[2-(6-Amino-9H-purin-9-yl)-1-methylethoxy]methyl]phosphonic acid bis-(isopropoxycarbonyloxymethyl)ester (bis-POC-PMPA), ribonucleotide reductase inhibitors, for example 2-acetylpyridine 5-[(2-chloroanilino)thiocarbonyl] thiocarbonohydrazone and hydroxyurea, nucleoside reverse transcriptase inhibitors, for example 3'-azido-3'-deoxythymidine (AZT, zidovudine), 2',3'-dideoxycytidine (ddC, zalcitabine), 2',3'-dideoxyadenosine, 2',3'-dideoxyinosine (ddI, didanosine), 2',3'-didehydrothymidine (d4T, stavudine), (−)-beta-D-2,6-diaminopurine dioxolane (DAPD), 3'-azido-2',3'-dideoxythymidine-5'-H-phosphophonate (phosphonovir), 2'-deoxy-5-iodo-uridine (idoxuridine), (−)-cis-1-(2-hydroxymethyl)-1,3-oxathiolane 5-yl)-cytosine (lamivudine), cis-1-(2-(hydroxymethyl)-1,3-oxathiolan-5-yl)-5-fluorocytosine (FTC), 3'-deoxy-3'-fluorothymidine, 5-chloro-2',3'-dideoxy-3'-fluorouridine, (−)cis-4-[2-amino-4-(cyclopropylamino)-9H-purin-9-yl]-2-cyclopentene-1-methanol (abacavir), 9-[4-hydroxy-2-(hydroxymethyl)but-1-yl]-guanine (H2G), ABT406 (2HM-H2G) and ribavirin, protease inhibitors, for example indinavir, ritonavir, nelfinavir, amprenavir, saquinavir, fosamprenavir, (R)-N-tert-butyl-3-[(2S,3S)-2-hydroxy-3-N-[(R-2-N-(isoquinolin-5-yloxyacetyl)amino-3-methylthiopropanoyl]amino-4-phenylbutanoyl]-5,5-dimethyl-1,3-thiazolidine-4-carboxamide (KNI-272), 4R-(4alpha,5alpha,6beta)]-1,3-bis[(3-aminophenyl)methyl]hexahydro-5,6-dihydroxy-4,7-bis(phenylmethyl)-2H-1,3-diazepin-2-one dimethanesulfonate (mozenavir), 3-[1-[3-[2-(5-trifluoromethylpyridinyl)-sulfonylamino]phenyl]propyl]4-hydroxy-6alpha-phenethyl-6beta-propyl-5,6-dihydro-2-pyranone (tipranavir), N'-[2(S)-Hydroxy-3(S)-[N-(methoxycarbonyl)-1-tert-leucylamino]-4-phenylbutyl-N$^{alpha}$-(methoxycarbonyl)-N'-[4-(2-pyridyl)benzyl]-L-tert-leucylhydrazide (BMS-232632), 3-(2(S)-Hydroxy-3(S)-(3-hydroxy-2-methylbenzamido)-4-phenylbutanoyl)-5,5-dimethyl-N-(2-methylbenzyl)thiazolidine-4(R)-carboxamide (AG-1776), N-(2(R)-hydroxy-1 (S)-indanyl)-2 (R)-phenyl-methyl-4(S)-hydroxy-5-(1-(1-(4-benzo[b]

furanylmethyl)-2(S)-N'-(tert-butylcarboxamido)piperazinyl) pentanamide (MK-944A), interferons such as α-interferon, renal excretion inhibitors such as probenecid, nucleoside transport inhibitors such as dipyridamole; pentoxifylline, N-acetylcysteine (NAC), Procysteine, α-trichosanthin, phosphonoformic acid, as well as immunomodulators such as interleukin II or thymosin, granulocyte macrophage colony stimulating factors, erythropoetin, soluble $CD_4$ and genetically engineered derivatives thereof, non-nucleoside reverse transcriptase inhibitors (NNRTIs), for example nevirapine (BI-RG-587), alpha-((2-acetyl-5-methylphenyl)amino)-2,6-dichloro-benzeneacetamide (loviride), 1-[3-(isopropylamino)-2-pyridyl]4-[5-(methanesulfonamido)-1H-indol-2-ylcarbonyl]piperazine monomethanesulfonate (delavirdine), (10R,11S,12S)-12-Hydroxy-6,6,10,11-tetramethyl-4-propyl-11,12-dihydro-2H, 6H, 10H-benzo(1,2-b:3,4-b':5,6-b") tripyran-2-one ((+) calanolide A), (4S)-6-Chloro-[1E)-cyclopropylethenyl)-3,4-dihydro-4-(trifluoromethyl)-2(1H)-quinazolinone (DPC-083), (S)-6-chloro-4-(cyclopropylethynyl)-1,4-dihydro-4-(trifluoromethyl)-2H-3, 1-benzoxazin-2-one (efavirenz, DMP 266), 1-(ethoxymethyl)-5-(1-methylethyl)-6-(phenylmethyl)-2,4 (1H,3H)-pyrimidinedione (MKC-442), and 5-(3,5-dichlorophenyl)thio-4-isopropyl-1-(4-pyridyl)methyl-1H-imidazol-2-ylmethyl carbamate (capravirine), glycoprotein 120 antagonists, for example PRO-2000, PRO-542 and 1,4-bis[3-[(2,4-dichlorophenyl)carbonylamino]-2-oxo-5,8-disodium-sulfanyl]naphthalyl-2,5-dimethoxyphenyl-1,4-dihydrazone (FP-21399), cytokine antagonists, for example reticulose (Product-R), 1,1'-azobis-formamide (ADA), 1,11-(1,4-phenylenebis(methylene))bis-1,4,8,11-tetraazacyclotetradecane octahydrochloride (AMD-3100), integrase inhibitors, or fusion inhibitors, for example T-20 and T-1249.

The present invention further includes the use of a compound according to the invention in the manufacture of a medicament for simultaneous or sequential administration with at least another therapeutic agent, such as those defined hereinbefore.

Compounds of the present invention may be administered with an agent known to inhibit or reduce the metabolism of compounds, for example ritonavir. Accordingly, the present invention features a method for the treatment, including prophylaxis, of a disease as hereinbefore described by administration of a compound of the present invention in combination with a metabolic inhibitor. Such combination may be administered simultaneously or sequentially.

In general a suitable dose for each of the above-mentioned conditions will be in the range of 0.01 to 250 mg per kilogram body weight of the recipient (e.g. a human) per day, suitably in the range of 0.1 to 100 mg per kilogram body weight per day and most suitably in the range 0.5 to 30 mg per kilogram body weight per day and particularly in the range 1.0 to 20 mg per kilogram body weight per day. Unless otherwise indicated, all weights of active ingredient are calculated as the parent compound of formula (I); for salts or esters thereof, the weights would be increased proportionally. The desired dose may be presented as one, two, three, four, five, six or more sub-doses administered at appropriate intervals throughout the day. In some cases the desired dose may be given on alternative days. These sub-doses may be administered in unit dosage forms, for example, containing 10 to 1000 mg or 50 to 500 mg, suitably 20 to 500 mg, and most suitably 50 to 400 mg of active ingredient per unit dosage form.

While it is possible for the active ingredient to be administered alone it is preferable to present it as a pharmaceutical composition. The compositions of the present invention comprise at least one active ingredient, as defined above, together with one or more acceptable carriers thereof and optionally other therapeutic agents. Each carrier must be acceptable in the sense of being compatible with the other ingredients of the composition and not injurious to the patient.

Pharmaceutical compositions include those suitable for oral, rectal, nasal, topical (including transdermal, buccal and sublingual), vaginal or parenteral (including subcutaneous, intramuscular, intravenous, intradermal, and intravitreal) administration. The compositions may conveniently be presented in unit dosage form and may be prepared by any methods well known in the art of pharmacy. Such methods represent a further feature of the present invention and include the step of bringing into association the active ingredients with the carrier, which constitutes one or more accessory ingredients. In general, the compositions are prepared by uniformly and intimately bringing into association the active ingredients with liquid carriers or finely divided solid carriers or both, and then if necessary shaping the product.

The present invention further includes a pharmaceutical composition as hereinbefore defined wherein a compound of the present invention or a pharmaceutically acceptable derivative thereof and another therapeutic agent are presented separately from one another as a kit of parts.

Compositions suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved and/or dispersed in an adhesive or 3) dispersed in a polymer. A suitable concentration of the active compound is about 1% to 25%, suitably about 3% to 15%. As one particular possibility, the active compound may be delivered from the patch by electrotransport or iontophoresis as generally described in *Pharmaceutical Research* 3 (6), 318 (1986).

Pharmaceutical compositions of the present invention suitable for oral administration may be presented as discrete units such as capsules, caplets, cachets or tablets each containing a predetermined amount of the active ingredients; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredients in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding a mixture of the powdered compound moistened with an inert liquid diluent in a suitable machine. The tablets may optionally be coated or scored and may be formulated so as to provide slow or controlled release of the active ingredients therein using, for example, hydroxypropylmethyl cellulose in varying proportions to provide the desired release profile. Tablets may optionally be provided with an enteric coating, to provide release in parts of the gut other than the stomach.

Pharmaceutical compositions suitable for topical administration in the mouth include lozenges comprising the active ingredients in a flavored base, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions suitable for vaginal administration may be presented as pessaries, tampons, creams, gels, pastes, foams or spray Pharmaceutical compositions containing in addition to the active ingredient such carriers as are known in the art to be appropriate.

Pharmaceutical compositions for rectal administration may be presented as a suppository with a suitable carrier comprising, for example, cocoa butter or a salicylate or other materials commonly used in the art. The suppositories may be conveniently formed by admixture of the active combination with the softened or melted carrier(s) followed by chilling and shaping in molds.

Pharmaceutical compositions suitable for parenteral administration include aqueous and nonaqueous isotonic sterile injection solutions which may contain anti-oxidants, buffers, bacteriostats and solutes which render the pharmaceutical composition isotonic with the blood of the intended recipient; and aqueous and non-aqueous sterile suspensions which may include suspending agents and thickening agents; and liposomes or other microparticulate systems which are designed to target the compound to blood components or one or more organs. The pharmaceutical compositions may be presented in unit-dose or multi-dose sealed containers, for example, ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

Unit dosage pharmaceutical compositions include those containing a daily dose or daily subdose of the active ingredients, as hereinbefore recited, or an appropriate fraction thereof.

It should be understood that in addition to the ingredients particularly mentioned above the pharmaceutical compositions of this invention may include other agents conventional in the art having regard to the type of pharmaceutical composition in question, for example, those suitable for oral administration may include such further agents as sweeteners, thickeners and flavoring agents.

EXAMPLES

The following examples are intended for illustration only and are not intended to limit the scope of the invention in any way.

Low resolution, open-access LC-MS data were acquired in either ESI pos/neg or APCI pos/neg mode with scanning from 100-1100 amu § 0.5 sec/scan. LC conditions: flowrate 0.8 mL/min. 85% $H_2O$ (0.1% formic acid) to 100% MeOH (0.075% formic acid) in 6 minutes. Phenomenex Max-RP column, 2.0×50 mm.

High Resolution Mass Spectra were acquired using Micromass LCT mass spectrometer (time-of-flight) with flow injection (FIA-MS) at 0.3 mL/min with 100% MeOH (0.1% formic acid), run time of 2 minutes, in ESI+ mode, scanning from 100-1100 amu @ 0.5 sec/scan. Reserpine was used as the lock mass (m/z 609.2812) and to adjust mass scale.

As will be appreciated by those skilled in the art, the following schemes may be followed in preparing the compounds of the present invention. Any variability depicted within the scheme(s) illustrated herein should be limited to the particular scheme and not necessarily extended throughout the rest of the present specification. Further, the compounds according to the invention contain one or more asymmetric carbon atoms and thus occur as racemates and racemic mixtures, single enantiomers, diastereomeric mixtures, and individual diastereoisomers. All such isomeric forms of these compounds are expressly included in the present invention. Although the scheme(s) may depict a particular stereochemical configuration, compounds having either the opposite stereochemistry at any given chiral center or mixtures thereof are also envisioned and prepared in a similar manner.

General Scheme

Synthesis of Cis and Trans Cyclohexylamine Derivatives with Two Carbon Linker scheme 1:

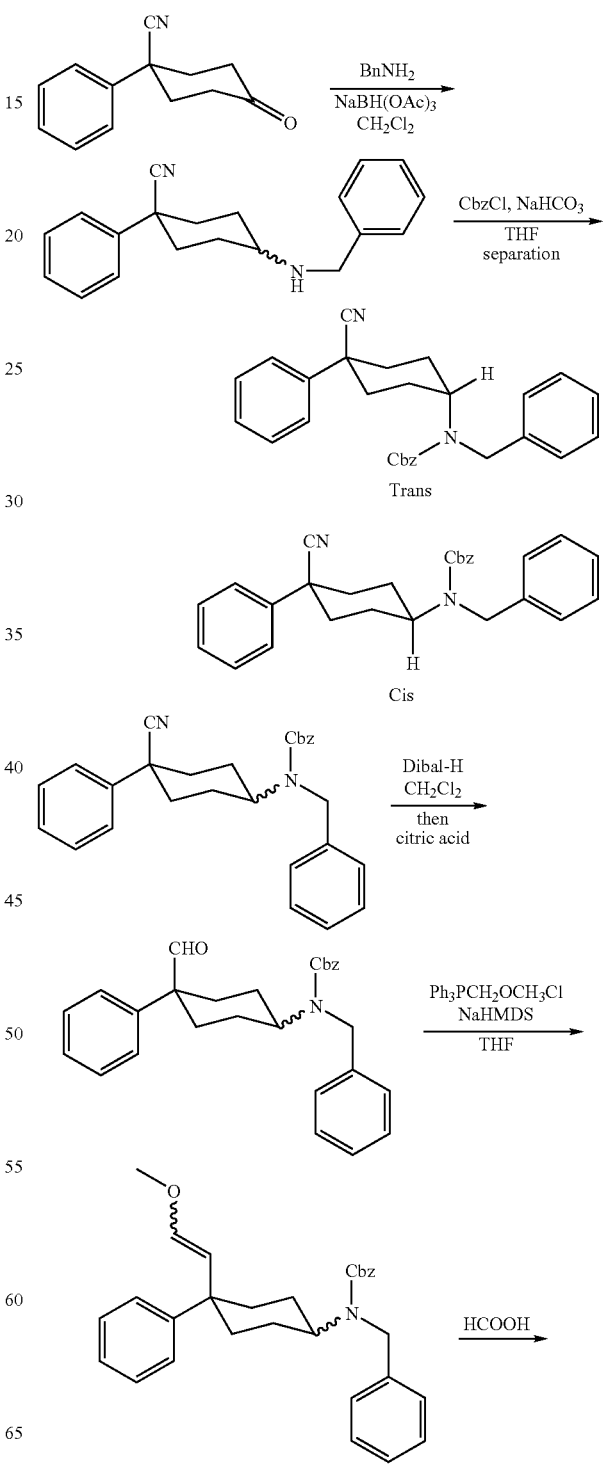

-continued
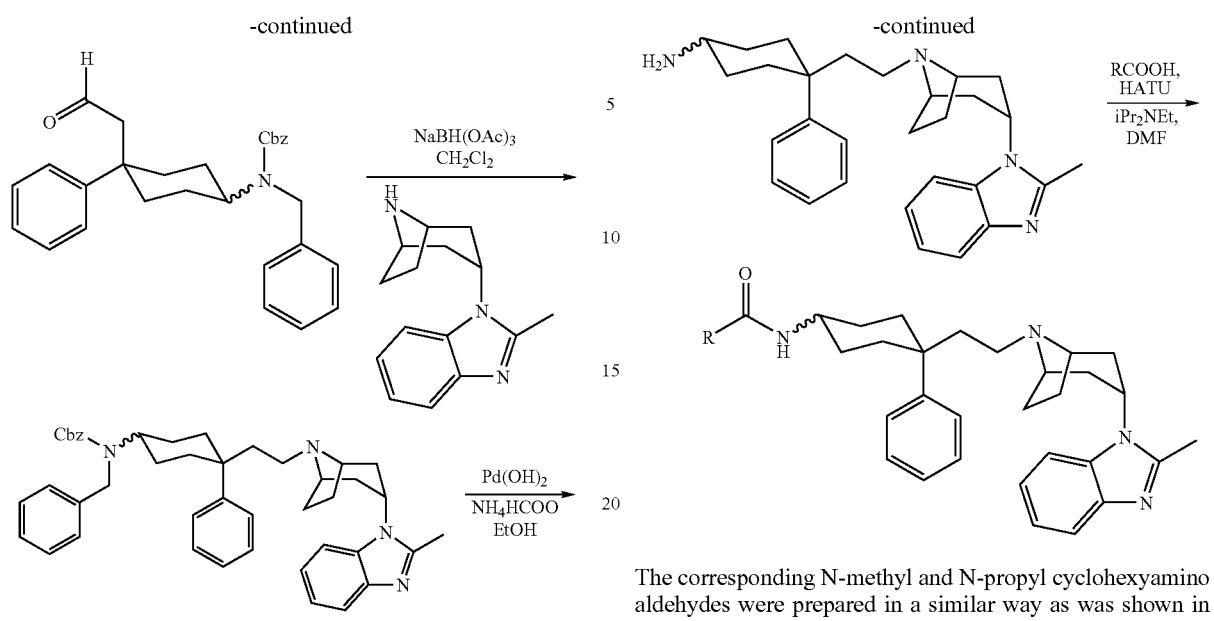
The corresponding N-methyl and N-propyl cyclohexyamino aldehydes were prepared in a similar way as was shown in scheme 1 and were used to couple with amines by reductive amination.
scheme 2
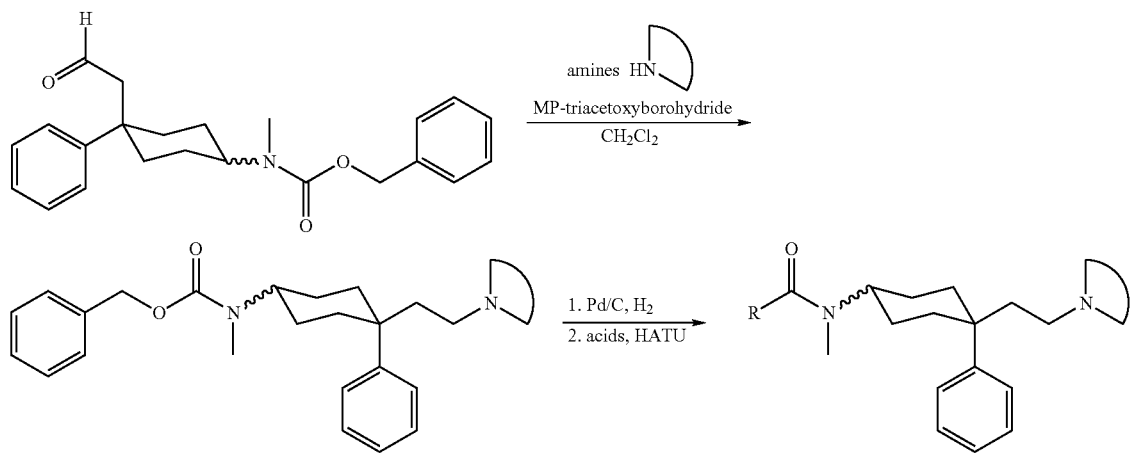
Cyclohexylamine with Three Carbon Linker
scheme 3:
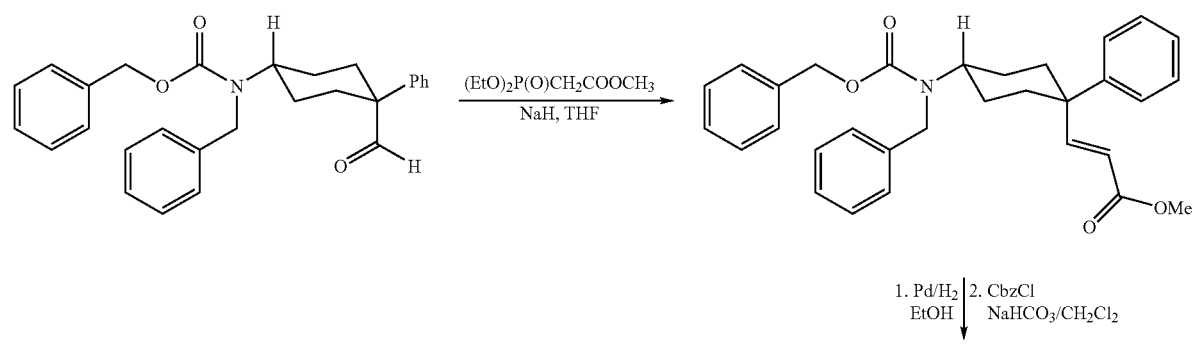

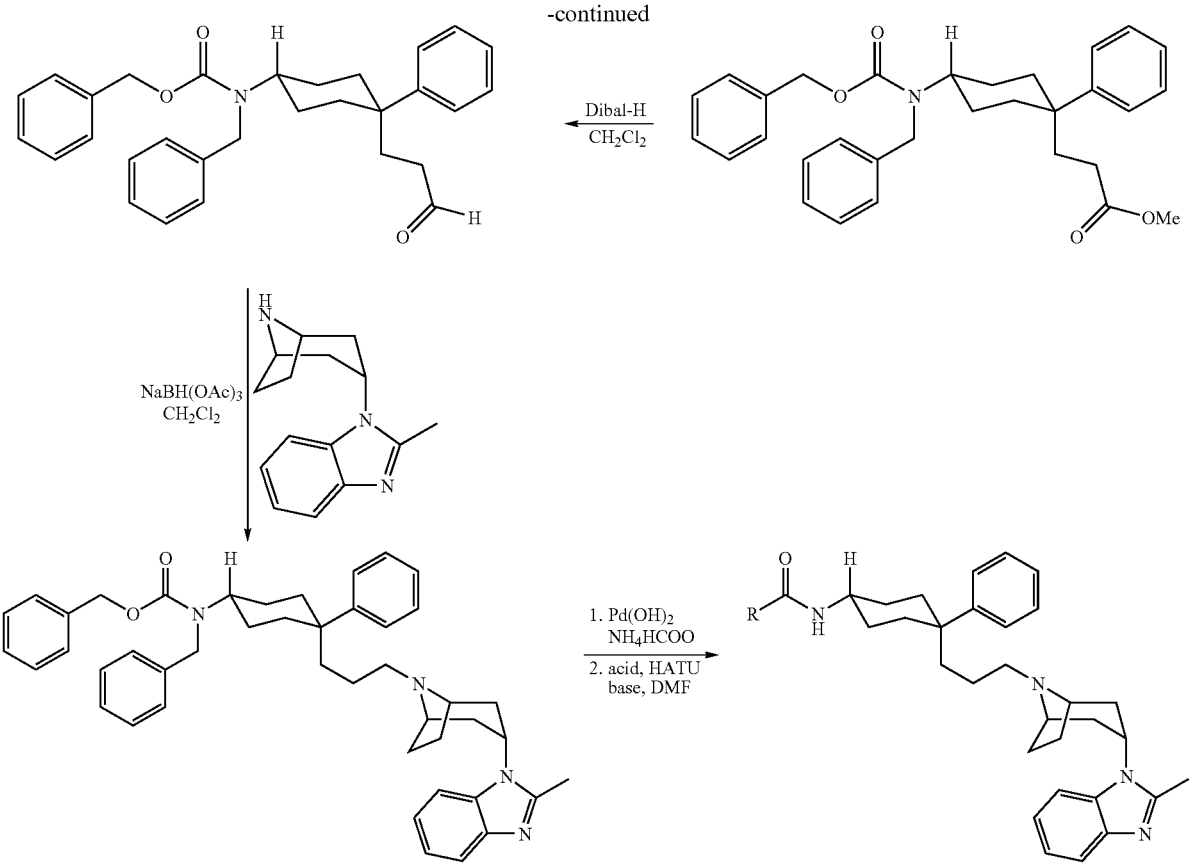

As noted above, and as will be appreciated by those skilled in the art, the above schemes may be followed in the preparation of the corresponding trans analogs as well.

Preparation 1 trans & cis-Benzyl Benzyl(4-cyano-4-phenylcyclohexyl)carbamates

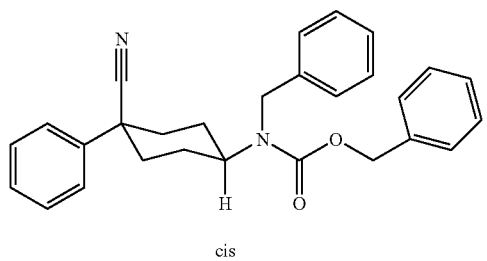

cis

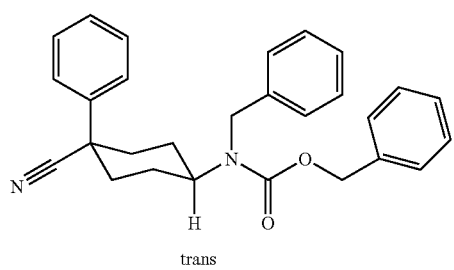

trans

Sodium triacetoxyborohydride (100.5 g. 474 mmol) was added portionwise to a stirred mixture of 4-phenyl-4-cyano-cyclohexnone (63 g, 316 mmol) and benzylamine (34 g, 316 mmol) in dichloromethane (400 mL) over 5 hours. The reaction was stirred overnight before carefully quenched with saturated sodium bicarbonate solution. Phases were separated and the aqueous phase was extracted with dichloromethane (2×100 mL). The combined extracts were washed with brine and dried over sodium sulfate. Evaporation of solvents afforded 1-phenyl-4-[(phenylmethyl)amino]cyclohexanecarbonitrile as a light yellow solid (90 g, 98%).

At 0° C., to a stirred solution of 1-phenyl-4[(phenylmethyl)amino]cyclohexane-carbonitrile (29 g, 100 mmol) in a mixed THF/NaHCO$_3$ (120 mL/140 mL) was added CbzCl (20.5 g, 120 mmol) dropwise. After being stirred on an ice-water bath for further 2.5 hours, the reaction mixture was diluted with ethyl acetate (500 mL), washed with saturated sodium bicarbonate solution, brine and dried over sodium sulfate. The solvents were evaporated. The crude mixtures was purified by flash chromatography to afford two isomers: cis isomer (1st fraction), 25.5 g (white solid); H$^1$NMR (400 MHz, CDCl3) δ 7.46-7.44 (m, 2H), 7.40-7.33 (m, 3H), 7.32-7.20 (m, 10H), 5.24-5.17 (m, 2H), 4.56 (s, 2H), 4.31 (br, +3.96 (br), 1H, rotational isomer), 2.19-2.17 (m, 2H), 2.05-1.65 (m, 6H). HRMS m/z (M+H)$^+$ calcd 425.2229, obsd 425.2202. trans isomer (2$^{nd}$ fraction): 12.6 g, H$^1$NMR (400 MHz, CDCl3) δ 7.42-7.26 (m, 8H), 7.21-7.19 (m, 5H), 7.03 (s, 1H), 5.13 (s, 2H), 4.27 (s, 2H), 4.10 (m, 1H), 2.67 (d, J=13 Hz, 2H), 2.14 (t, J=13.5 Hz, 2H), 1.67-1.49 (m, 4H). HRMS m/z (M+H)$^+$ calcd 425.2229, obsd 425.2204.

Preparation 2 cis-Benzyl Benzyl(4-formyl-4-phenylcyclohexyl)carbamate

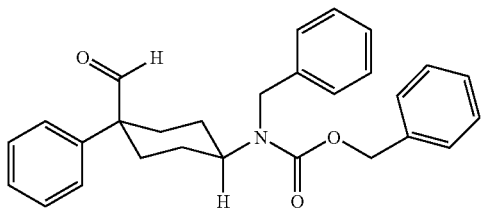

At −78° C., to a stirred solution of cis-benzyl benzyl(4-cyano-4-phenylcyclohexyl)carbamate (18.5 g, 43.4 mmol) in dichloromethane (200 mL) was slowly added Dibal-H (67 mL, 1.0 M in hexane) over 30 minutes. After a 5-hour stirring, the reaction mixture was carefully quenched with methanol and then brought up to the room temperature. ~400 mL of saturated citric add solution was added. The mixture was then allowed to stir overnight. Layers were separated and the aqueous layer was extracted with dichloromethane (2×100 mL). The combined organic extracts were dried over sodium sulfate. After evaporation of solvents, the crude aldehyde was purified by flash column chromatography (hexane/EtOAc, 6:1) to afford a white solid (12.8 g, 69%). H$^1$NMR (400 MHz, CDCl3) δ 9.31 (s, 1H), 7.44-7.17 (m, 15H), 5.22-5.13 (m, 2H), 4.42 (br, 2H), 4.15 (br, +3.87 (br), 1H, rotational isomer), 2.56 (d, J=11.3 Hz, 2H), 1.78-1.26 (m, 6H). HRMS m/z (M+H)$^+$ calcd 428.2226, obsd 428.2245.

Preparation 3 trans-Benzyl Benzyl(4-formyl-4-phenylcyclohexyl)carbamate

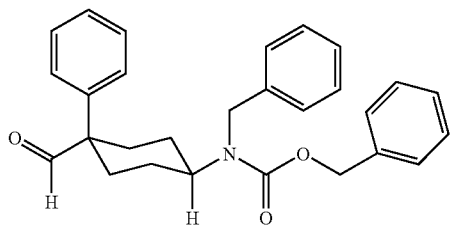

trans-Benzyl benzyl(4-formyl-4-phenylcyclohexyl)carbamate (7.1 g, 73%) was obtained as a white solid from trans-benzyl benzyl(4-cyano-4-phenylcyclohexyl) carbamate (9.6 g, 22.6 mmol) and Dibal-H (34 mL, 1.0 M in hexane), following the procedure outlined in the Preparation 2. H$^1$NMR (400 MHz, CDCl3) δ 9.32 (s, 1H), 7.46-7.03 (m, 15H), 5.13 (br, 2H), 4.27-3.91 (m, 3H), 2.51-2.47 (m, 2H), 1.69-1.54 (m, 6H). HRMS m/z (M+H)$^+$ calcd 428.2226, obsd 428.2245.

Preparation 4 cis-Benzyl Benzyl(4-{2-[3-2-methyl-1H-benzimidazol-1-yl)-8-azabicyclo[3.2.1]oct-8-yl]ethyl}-4-phenylcyclohexyl)carbamate

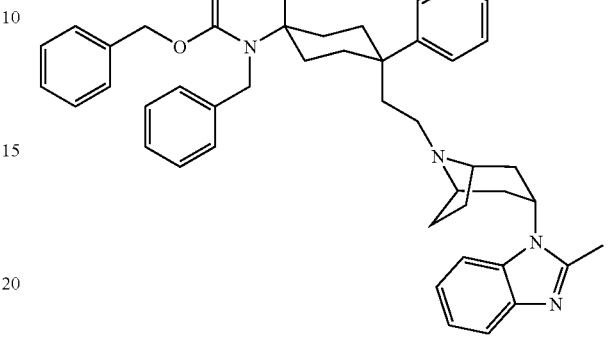

Step 1:
At −78° C., to a stirred suspension of methoxymethyltriphenyl phosphonium chloride (13.7 g, 40 mmol) in THF (60 mL) was added KHMDS (60 mL, 0.5 M in toluene) by a syringe. The mixture was stirred for 3 hours before being cannuled into a precooled (0° C.) stirred solution of cis-benzyl benzyl(4-formyl-4-phenylcyclohexyl)carbamate (8.5 g, 20 mmol) in THF (60 mL). The reaction was allowed to stir for 6 hours at 0° C. before being quenched with saturated ammonium chloride. The resultant mixture was concentrated down to ~half of the original volume to remove THF and the crude product was extracted with dichloromethane. The combined extracts were washed with saturated sodium bicarbonate solution, brine and dried over sodium sulfate. Evaporation of solvents and flash chromatography provided a mixture of Z/E isomers (oil, 4.3 g, 67%) H$^1$NMR looked messy due to the Z/E mixture as well as floppy cyclohexyl ring. HRMS m/z (M+H)$^+$ calcd 456.2539, obsd 452.2538.

Step 2:
A mixture of Z/E isomers (4.3 g, 9.5 mmol) prepared from step 1 was vigorously stirred in 10 mL of 90% formic acid for 6 hours before it was slowly poured into a stirred sodium bicarbonate solution. The aqueous solution was extracted with dichloromethane. The combined extracts were washed with saturated sodium bicarbonate solution, brine and dried over sodium sulfate. Evaporation of solvents afforded a white solid, which was directly used for the next step without purification.

Step 3:
To a precooled (0° C.) stirred solution of the aldahyde (~9.5 mmol) prepared from step 2 and 1-(8-azabicyclo[3.2.1]oct-3-yl)-2-methyl-1H-benzimidazole dihydrochloride (3.5 g, 10 mmol) was added sodium triacetoxyborohydride (3.2 g, 15 mmol). The reaction mixture was allowed to stir for 4 hours before being quenched with saturated sodium bicarbonate solution. Layers were separated and the aqueous layer was extracted with dichlormethane (2×50 mL). The combined extracts were washed with saturated sodium bicarbonate solution, brine and dried over sodium sulfate. Evaporation of solvents and flash chromatography afforded cis-benzyl benzyl(4-{2-[3-(2-methyl-1H-benzimidazol-1-yl)-8-azabicyclo[3.2.1]oct-8-yl]ethyl}4-phenylcyclohexyl)carbamate as a white foam (5.33 g, 84% over two steps). H¹NMR (400 MHz, CDCl3) δ 7.67 (d, J=7.5 Hz, 1H), 7.31-7.13 (m, 18H), 5.15 (br, 2H), 4.57 (br, 3H), 3.89 (br, 1H), 3.18 (br, 2H), 2.55 (s, 3H), 2.37-2.29 (m, 2H), 2.13-2.05 (m, 2H), 1.96-1.80 (m, 9H), 1.72-1.55 (m, 7H). HRMS m/z (M+H)⁺ calcd 667.3990, obsd 667.4012.

Preparation 5 trans-Benzyl Benzyl(4-{2-[3-(2-methyl-1H-benzimidazol-1-yl)-8-azabicyclo[3.2.1]oct-8-yl]ethyl}-4-phenylcyclohexyl)carbamate

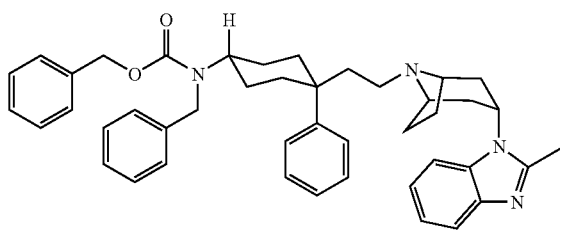

trans-Benzyl benzyl(4-{2-[3-(2-methyl-1H-benzimidazol-1-yl)-8-azabicyclo[3.2.1]oct-8-yl]ethyl}4-phenylcyclohexyl)carbamate (787 mg, 52% over the three steps) was obtained as a white solid from trans-benzyl benzyl(4-formyl-4-phenylcyclohexyl) carbamate (0.89 g, 2.1 mmol) and 1-(8-azabicyclo[3.2.1]oct-3-yl)-2-methyl-1H-benzimidazole (340 mg, 1.4 mmol), following the procedures outlined in Prearation 4. H¹NMR (400 MHz, CDCl3) δ 7.67 (d, J=7.3 Hz, 1H), 7.36-7.12 (m, 16H), 7.00 (br, 2H), 5.10 (br, 2H), 4.63 (m, 1H), 4.30-4.15 (m, 3H), 3.24 (br, 2H), 2.56 (s, 3H), 2.44-2.33 (m, 4H), 1.92-1.86 (6H), 1.63-1.42 (m, 10H). HRMS m/z (M+H)⁺ calcd 667.3990, obsd 667.4009.

Preparation 6 cis-4-{2-[3-(2-Methyl-1H-benzimidazol-1-yl)-8-azabicyclo[3.2.1]oct-8-yl]ethyl}-4-phenylcyclohexanamine

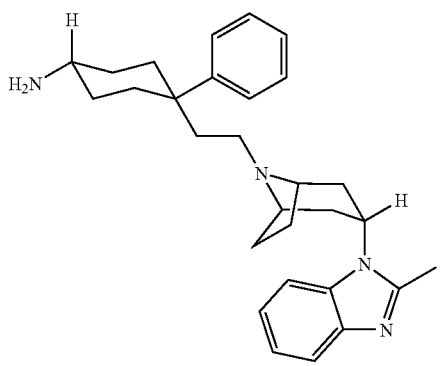

cis-Benzyl benzyl(4-{2-[3-(2-methyl-1H-benzimidazol-1-yl)-8-azabicyclo[3.2.1]oct-8-yl]ethyl}-4-phenylcyclohexyl)carbamate (4.67 g, 7 mmol) in ethanol (80 mL) was heated to reflux for 2 hours in the presence of large excess ammonium formate (8.8 g, 140 mmol) and catalytic amount of Pd(OH)₂ (0.46 g). After filtration, the filtrate was concentrated and the residue was partitioned between CH₂Cl₂/water (200 mL/100 mL). The aqueous phase was extracted with dichloromethane (3×50 mL). The combined extracts were washed with saturated sodium bicarbonate solution, brine and dried over sodium sulfate. Evaporation of solvents gave cis-4-{2-[3-(2-methyl-1H-benzimidazol-1-yl)-8-azabicyclo [3.2.1]oct-8-yl]ethyl}-4-phenylcyclohexanamine (2.0 g, foam, 63%), which was directly used for acylations.

The corresponding trans-4-(2-[3-(2-methyl-1H-benzimidazol-1-yl)-8-azabicyclo[3.2.1]oct-8-yl]ethyl}-4-phenylcyclohexanamine was prepared in the same method.

Preparation 7 cis 3-(Aminosulfonyl)-4-chloro-N-4-{2-[3-(2-methyl-1H-benzimidazol-1-yl)-8-azabicyclo[3.2.1]oct-8-yl]ethyl}-4-phenylcyclohexyl)benzamide GW877017X (u19394-101-8)

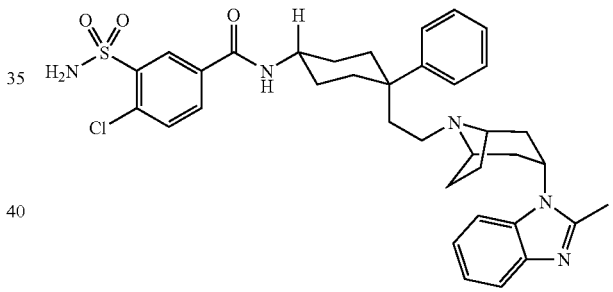

To a stirred mixture of cis-4-{2-[3-(2-methyl-1H-benzimidazol-1-yl)-8-azabicyclo[3.2.1]oct-8-yl]ethyl}-4-phenylcyclohexanamine (44 mg, 0.1 mmol) and 3-(aminosulfonyl)-4-chlorobenzoic acid (24 mg, 0.1 mmol) in DMF (3 mL) was added N,N-diisopropyl ethylamine (13 mg, 0.1 mmol) and HATU (38 mg, 0.1 mmol). The resulting mixture was allowed to stir for 2 hours before diluted with ethyl acetate, washed with sodium bicarbonate solution, brine and dried over sodium sulfate. Evaporation of solvents and purification by flash chromatography afforded cis-3-(aminosutfonyl)-4-chloro-N-(4-{2-[3-(2-methyl-1H-benzimidazol-1-yl)-8-azabicyclo[3.2.1]

oct-8-yl]ethyl)-4-phenylcyclohexyl)benzamide as foam (40 mg, 61%). H¹NMR (400 MHz, CDCl3) δ 8.38 (s, 1H), 7.57-7.52 (m, 2H), 7.32-7.13 (m, 9H), 4.60 (br, 1H), 4.00 (br, 1H), 3.32 (br, 2H), 2.48 (s, 3H), 2.30 (br, 3H), 2.04-1.80 (m, 19H), 1.54 (br, 3H). HRMS m/z (M+H)⁺ calcd 660.2775, obsd 660.2762.

Preparation 8 cis N-(4-{2-[3-(2-methyl-1H-benzimidazol-1-yl)-8-azabicyclo[3.2.1]oct-8-yl]ethyl}-4-phenylcyclohexyl)-1H-pyrazole-4-carboxamide GW 877015X (u19394-102-2)

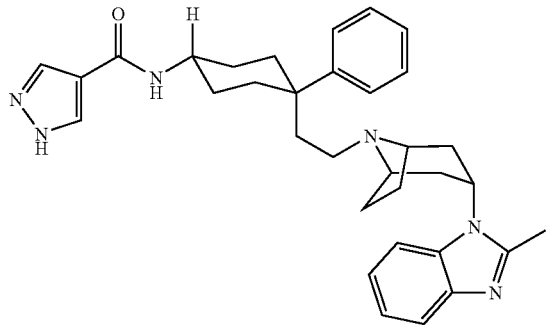

cis N-(4-{2-[3-(2-methyl-1H-benzimidazol-1-yl)-8-azabicyclo[3.2.1]oct-8-yl]ethyl}-4-phenylcyclohexyl)-1H-pyrazole-4-carboxamide (28 mg, 52%) was obtained as foam from cis-4-{2-[3-(2-methyl-1H-benzimidazol-1-yl)-8-azabicyclo[3.2.1]oct-8-yl]ethyl}-4-phenylcyclohexanamine (44 mg, 0.1 mmol) and 1H-pyrazole-4-carboxylic acid (11.2 mg, 0.1 mmol) and HATU (38 mg, 0.1 mmol), following the procedures outlined in Preparation 7. $H^1$NMR (400 MHz, CDCl3) δ 8.09 (br, 1H), 7.53 (d, J=6.4 Hz, 1H0, 7.42-7.40 (m, 3H), 7.35-7.31 (m, 2H), 7.21-7.15 (m, 3H), 4.86 (s, 2H), 4.81-4.76 (m, 1H), 3.88 (br, 1H), 3.34-3.30 (m, 3H), 2.55 (s, 3H0, 2.48-2.40 (m, 2H), 2.19-2.16 (m, 2H), 2.07-2.05 (m, 2H), 1.99-1.86 (m, 8H0, 1.83-1.67 (m, 6H). HRMS m/z (M+H)$^+$ calcd 537.3344, obsd 537.3354.

Preparation 9 cis-4-(aminosulfonyl)-N-(4-{2-[3-(2-methyl-1H-benzimidazol-1-yl)-8-azabicyclo[3.2.1]oct-8-yl]ethyl}-4-phenylcyclohexyl)benzamide GSK319128A (u19911-67-1)

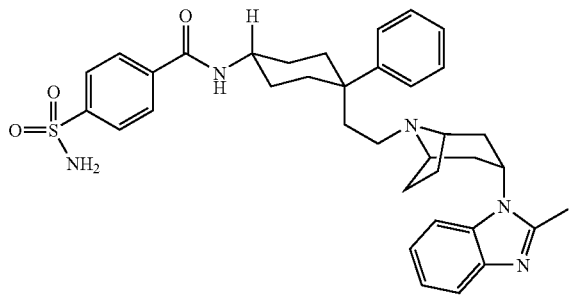

cis-4-(Aminosulfonyl)-N-(4-{2-[3-(2-methyl-1H-benzimidazol-1-yl)-8-azabicyclo[3.2.1]oct-8-yl]ethyl}-4-phenylcyclohexyl)benzamide (21 mg, 65%) was obtained as white solid from cis-4-{2-[3-(2-methyl-1H-benzimidazol-1-yl)-8-azabicyclo[3.2.1]oct-8-yl]ethyl}-4-phenylcyclohexanamine (22 mg, 0.05 mmol), 4-aminosulfonylbenzoic acid (10 mg, 0.05 mmol) and HATU (19 mg, 0.05 mmol), following the procedures outlined in Preparation 7. $H^1$NMR (400 MHz, CD$_2$Cl$_2$) δ 7.92 (br, 4H), 7.52 (s, 1H), 7.33 (br, 5H), 7.15 (br, 3H), 4.82 (br, 1H), 4.72-4.39 (m, 4H), 3.92 (br, 1H), 3.33 (br, 2H), 2.50 (s, 3H), 2.39 (br, 2H), 2.08 (br, 2H), 1.97-1.91 (m, 9H), 1.76 (br, 4H), 1.63 (br, 2H). HRMS m/z (M+H)$^+$ calcd 626.3165, obsd 626.3165.

Preparation 10 cis-4-(aminosulfonyl)-2-fluoro-N-(4-{2-[3-(2-methyl-1H-benzimidazol-1-yl)-8-azabicyclo[3.2.1]oct-8-yl]ethyl}-4-phenylcyclohexyl)benzamide GSK319129A (u19911-67-2)

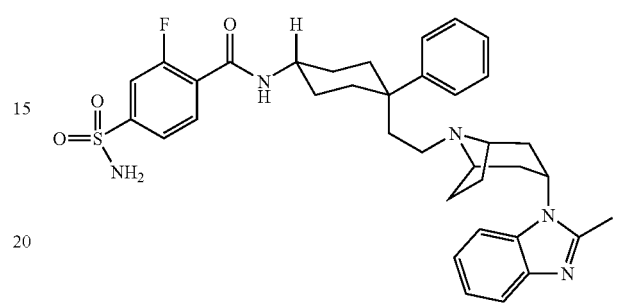

cis-4-(Aminosulfonyl)-2-fluoro-N-(4-{2-[3-(2-methyl-1H-benzimidazol-1-yl)-8-azabicyclo[3.2.1]oct-8-yl]ethyl}-4-phenylcyclohexyl)benzamide (18 mg, 56%) was obtained as white solid from cis-4-{2-[3-(2-methyl-1H-benzimidazol-1-yl)-8-azabicyclo[3.2.1]oct-8-yl]ethyl}-4-phenylcyclohexanamine (22 mg, 0.05 mmol), 2-fluoro-(4-aminosulfonyl)benzoic acid (12 mg, 0.05 mmol) and HATU (19 mg, 0.05 mmol), following the procedures outlined in Preparation 7. $H^1$NMR (400 MHz, CD$_2$Cl$_2$) δ 7.83 (t, J=7.2 Hz, 1H), 7.73-7.63 (m, 2H), 7.51-7.48 (m, 1H), 7.34-7.23 (m, 5H), 7.18-7.12 (m, 3H), 4.73-4.67 (m, 1H), 4.52 (br, 2H), 3.92 (br, 1H), 3.28 (br, 2H), 2.48 (s, 3H), 2.41-2.33 (m, 2H), 2.10-2.05 (m, 2H), 1.96-1.72 (m, 14H), 1.69-1.63 (m, 2H). HRMS m/z (M+H)$^+$ calcd 644.3077, obsd 644.3084.

Preparation 11 cis-4-(aminosulfonyl)-2-chloro-N-(4-[{2-[3-(2-methyl-1H-benzimidazol-1-yl)-8-azabicyclo[3.2.1]oct-8-yl]ethyl}-4-phenylcyclohexyl)benzamide GSK319130A (u19911-67-3)

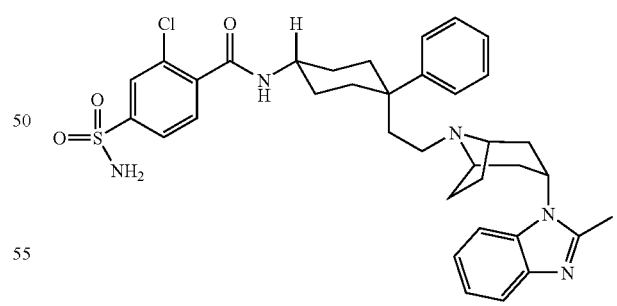

cis-4-(Aminosulfonyl)-2-chloro-N-(4-{2-[3-(2-methyl-1H-benzimidazol-1-yl)-8-azabicyclo[3.2.1]oct-8-yl]ethyl}4-phenylcyclohexyl)benzamide (15 mg, 45%) was obtained as white solid from cis-4-{2-[3-(2-methyl-1H-benzimidazol-1-yl)-8-azabicyclo[3.2.1]oct-8-yl]ethyl}A4-phenylcyclohexanamine (22 mg, 0.05 mmol), 2-chloro-(4-aminosulfonyl)benzoic acid (12 mg, 0.05 mmol) and HATU (19 mg, 0.05 mmol), following the procedures outlined in Preparation 7. $H^1$NMR (400 MHz, CD$_2$Cl$_2$) δ 7.82 (d, J=8.1 Hz, 1H), 7.58-7.53 (m, 2H), 7.36-7.31 (m, 6H), 7.21-7.14 (m, 3H), 4.71-4.66 (m, 1H), 3.97 (br, 2H), 3.30 (br, 2H), 2.50 (s, 3H), 2.42-2.34 (m, 2H), 2.06-2.03 (m, 2H), 1.99-1.71 (m, 14H), 1.62-1.59 (m 2H). HRMS m/z (M+H)+ calcd 660.2791, obsd 660.2775.

Preparation 12 cis-2-chloro-4-fluoro-5-[(methylamino)sulfonyl]-N-(4-(2-[3-(2-methyl-1H-benzimidazol-1-yl)-8-azabi-cyclo[3.2.1]oct-8-yl]ethyl}-4-phenylcyclohexyl) benzamide GSK319131A (u19911-67-4)

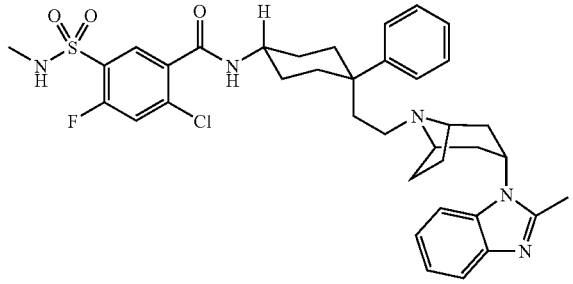

cis-2-Chloro-4-fluoro-S-[(methylamino)sulfonyl]-N-(4-{2-[3-(2-methyl-1H-benzimidazol-1-yl)-8-azabicyclo [3.2.1]oct-8-yl]ethyl}-4-phenylcyclohexyl)benzamide (28 mg, 80%) was obtained as white solid from cis-4-{2-[3-(2-methyl-1H-benzimidazol-1-yl)-8-azabicyclo[3.2.1]oct-8-yl] ethyl}-4-phenylcyclohexanamine (22 mg, 0.05 mmol), 2-chloro-4-fluoro-5-[(methylamino)sulfonyl]benzoic acid (14 mg, 0.05 mmol) and HATU (19 mg, 0.05 mmol), following the procedures outlined in Preparation 7. H¹NMR (400 MHz, CD₂Cl₂) δ 7.98 (d, J=7.5 Hz, 1H), 7.58-7.56 (m, 1H), 7.38-7.33 (m, 6H), 7.24-7.15 (m, 3H), 4.73-4.68 (m, 1H), 3.99-3.94 (m, 1H), 3.60 (br, 2H), 3.33 (br, 2H), 2.66 (s, 3H), 2.53 (s, 3H), 2.44-2.36 (m, 2H), 2.08-2.05 (m, 2H), 1.99-1.73 (m. 14H), 1.66-1.64 (m, 2H). HRMS m/z (M+H)+ calcd 692.2839, obsd 692.2837.

Preparation 13 cis-4-chloro-2-fluoro-5-{[(4-{2-[3-(2-methyl-1H-benzimidazol-1-yl)-8-azabicyclo[3.2.1]oct-8-yl] ethyl}-4-phenylcyclohexyl)amino] carbonyl}benzenesulfonic acid GSK319165A (u19911-67-5)

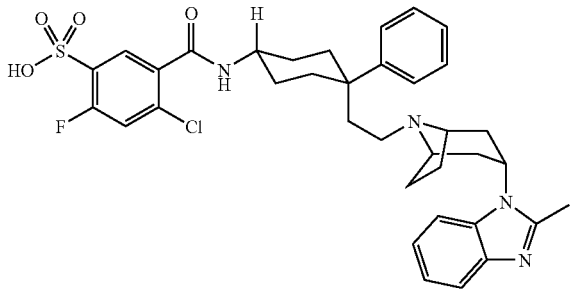

cis-4-Chloro-2-fluoro-5-{[(4-{2-[3-(2-methyl-1H-benzimidazol-1-yl)-8-azabicyclo[3.2.1]oct-8-yl]ethyl}-4-phenylcyclohexyl)amino]carbonyl}benzenesulfonic acid (10 mg, 27%) was obtained as white solid from cis-4-(2-[3-(2-methyl-1H-benzimidazol-1-yl)-8-azabicyclo[3.2.1]oct-8-yl]ethyl)-4-phenylcyclohexanamine (22 mg, 0.05 mmol), 2-chloro-4-fluoro-5-sulfobenzoic acid (13 mg, 0.05 mmol) and HATU (19 mg, 0.05 mmol), following the procedures outlined in Preparation 7. H¹NMR (400 MHz, CD₃OD) δ 7.90 (d, J=7.3 Hz, 1H), 7.53-7.51 (m, 1H), 7.43-7.33 (m, 6H), 7.20-7.15 (m, 3H), 4.81-4.74 (m, 1H), 3.91 (br, 1H), 3.39 (br, 2H), 2.55 (s, 3H), 2.47-2.38 (m, 2H), 2.14-2.12 (m, 2H), 1.97-1.70 (m, 16H). HRMS m/z (M+H)+ calcd 679.2532, obsd 679.2521.

Preparation 14 cis-3-(aminosulfonyl)-4-fluoro-N-(4-{2-[3-(2-methyl-1H-benzimidazol-1-yl)-8-azabicyclo[3.2.1]oct-8-yl]ethyl}-4-phenylcyclohexyl)benzamide GSK319166A (u19911-67-6)

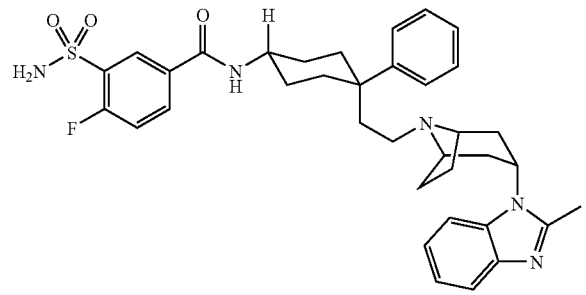

cis-3-(Aminosulfonyl)-4-fluoro-N-(4-{2-[3-(2-methyl-1H-benzimidazol-1-yl)-8-azabicyclo[3.2.1]oct-8-yl]ethyl)-4-phenylcyclohexyl)benzamide (20 mg, 62%) was obtained as white solid from cis-4-{2-[3-(2-methyl-1H-benzimidazol-1-yl)-8-azabicyclo[3.2.1]oct-8-yl]ethyl}-4-phenylcyclohexanamine (22 mg, 0.05 mmol), 4 fluoro-(3-aminosulfonyl) benzoic acid (12 mg, 0.05 mmol) and HATU (19 mg, 0.05 mmol), following the procedures outlined in Preparation 7. H¹NMR (400 MHz, CDCl₃) δ 8.23-8.21 (m, 1H), 8.11-8.08 (m, 1H), 7.58 (d, J=8.6 Hz, 1H), 7.35-7.30 (m, 4H), 7.24-7.20 (m, 4H), 7.19-7.10 (m, 2H), 6.80 (d, J=7.3 Hz, 1H), 4.63 (br, 1H), 3.99 (br, 1H), 3.25 (br, 2H), 2.49 (s, 3H), 2.37-2.29 (m, 2H), 2.09-2.03 (m, 2H), 1.98-1.72 (m, 15H), 1.57-1.55 (m, 12H). HRMS m/z (M+H)+ calcd 644.3091, obsd 644.3071.

Preparation 15 cis-4-chloro-5-[(cyclopropylamino)sulfonyl-2-fluoro-N-(4-(2-[3-(2-methyl-1H-benzimidazol-1-yl)-8-azabicyclo[3.2.1]oct-8-yl]ethyl}-4-phenylcyclohexyl) benzamide GSK319469A (u19911-67-8)

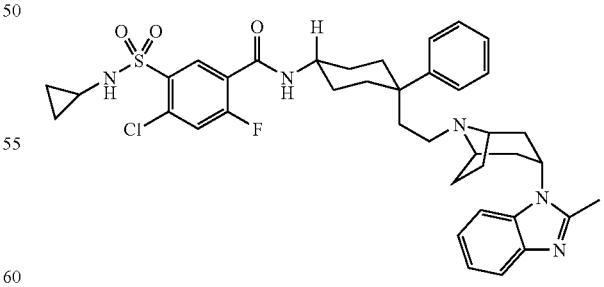

cis-4-Chloro-5-[(cyclopropylamino)sulfonyl]-2-fluoro-N-(4-{2-[3-(2-methyl-1H-benzimidazol-1-yl)-8-azabicyclo [3.2.1]oct-8-yl]ethyl}-4-phenylcyclohexyl) benzamide (24 mg, 67%) was obtained as white solid from cis-4-{2-[3-(2-methyl-1H-benzimidazol-1-yl)-8-azabicyclo[3.2.1]oct-8-yl] ethyl}-4-phenylcyclohexanamine (22 mg, 0.05 mmol), 4-chloro-5-[(cyclopropylamino)sulfonyl]-2-fluorobenzoic acid (15 mg, 0.05 mmol) and HATU (19 mg, 0.05 mmol), following the procedures outlined in Preparation 7. H¹NMR (400 MHz, CDCl₃) δ 8.16 (d, J=7.5 Hz, 1H), 7.64 (d, J=7.2 Hz, 1H), 7.38-7.30 (m, 5H), 7.28-7.26 (m, 1H), 7.24-7.12 (m, 3H), 6.34 (d, J=7.7 Hz, 1H), 4.64-4.59 (m, 1H), 4.04 (br, 1H), 3.26 (br, 2H), 2.55 (s, 3H), 2.40-2.28 (m, 4H), 2.10 (br, 3H), 1.91-1.73 (m, 13H), 1.60-1.59 (m, 2H), 0.68-0.64 (m, 4H). HRMS m/z (M+H)⁺ calcd 718.2979, obsd 718.2994.

Preparation 16 cis-methyl 3-{[(4-{2-[3-(2-methyl-1H-benzimidazol-1-yl]-8-azabicyclo[3.2.1]oct-8-yl]ethyl}-4-phenylcyclohexyl)amino]carbonyl}benzoate GSK319470A (u19911-67-9)

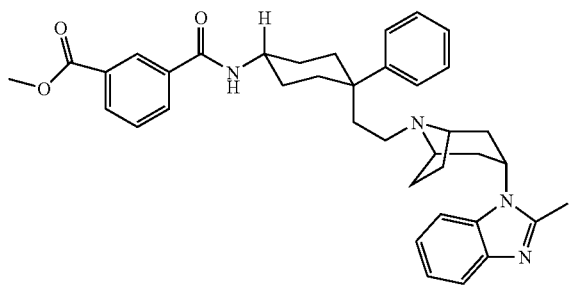

cis-Methyl 3-{[(4-{2-[3-(2-methyl-1H-benzimidazol-1-yl)-8-azabicyclo[3.2.1]oct-8-yl]ethyl}-4-phenylcyclohexyl)amino]carbonyl}benzoate (21 mg, 70%) was obtained as white solid from cis-4-{2-[3-(2-methyl-1H-benzimidazol-1-yl)-8-azabicyclo[3.2.1]oct-8-yl]ethyl}-4-phenylcyclohexanamine (22 mg, 0.05 mmol), 3-(methoxycarbonyl)benzoic acid (9 mg, 0.05 mmol) and HATU (19 mg, 0.05 mmol), following the procedures outlined in Preparation 7. H¹NMR (400 MHz, CDCl₃) δ 8.36 (s, 1H), 8.16 (d, J=7.7 Hz, 1H), 8.08 (d, J=7.8 Hz, 1H), 7.66 (d, J=7.3 Hz, 1H), 7.54 (t, J=7.7 Hz, 1H), 7.35-7.31 (m, 4H), 7.29-7.26 (m, 1H), 7.24-7.12 (m, 3H), 6.31 (d, J=7.3 Hz, 1H), 4.65 (br, 1H), 4.09-4.04 (m, 1H), 3.94 (s, 3H), 3.28 (br, 2H), 2.57 (s, 3H), 2.42-2.34 (m, 2H), 2.08-2.05 (m, 3H), 1.93-1.73 (m, 12H), 1.62-1.60 (m, 2H). HRMS m/z (M+H)⁺ calcd 605.3488, obsd 605.3492.

Preparation 17 cis-2,6-difluoro-N-(4-{2-[3-(2-methyl-1H-benzimidazol-1-yl)-8-azabicyclo[3.2.1 oct-8-yl]ethyl}-4-phenylcyclohexyl)-3-[(methylsulfonyl)amino]benzamide GSK332376A (u19911-71-1)

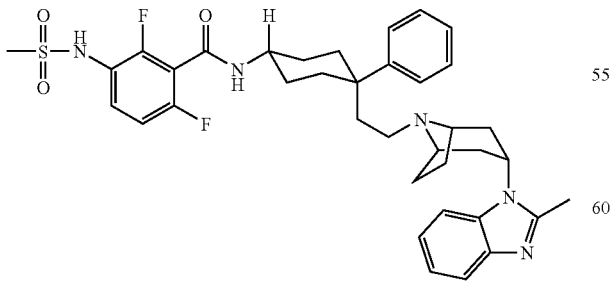

cis-2,6-Difluoro-N-(4-{2-[3-(2-methyl-1H-benzimidazol-1-yl)-8-azabicyclo[3.2.1]oct-8-yl]ethyl}-4-phenylcyclohexyl)-3-[(methylsulfonyl)amino]benzamide (14 mg, 36%) was obtained as white solid from cis-4-{2-[3-(2-methyl-1H-benzimidazol-1-yl)-8-azabicyclo[3.2.1]oct-8-yl]ethyl}-4-phenylcyclohexanamine (22 mg, 0.05 mmol), 2,6-difluoro-3-[(methylsulfonyl)amino]benzoic acid (13 mg, 0.05 mmol) and HATU (19 mg, 0.05 mmol), following the procedures outlined in Preparation 7. H¹NMR (400 MHz, CDCl₃) δ 7.62 (d, J=7.5 Hz, 1H), 7.54-7.49 (m, 1H), 7.35-7.30 (m, 4H), 7.23-7.11 (m, 4H), 6.90 (t, J=8.4 Hz, 1H), 6.76 (d, J=7.5 Hz, 1H), 4.67 (br, 1H), 4.04 (br, 1H), 3.29 (br, 2H), 2.93 (s, 3H), 2.48 (s, 3H), 2.38-2.30 (m, 2H), 2.03-1.82 (m, 14H), 1.76-1.68 (m, 2H), 1.61-1.59 (m, 2H), HRMS m/z (M+H)⁺ calcd 676.3141, obsd 676.3133.

Preparation 18 cis-4-chloro-2-fluoro-N-(4-{2-[3-(2-methyl-1H-benzimidazol-1-yl)-8-azabicyclo[3.2.1]oct-8-yl]ethyl}-4-phenylcyclohexyl)-5-[(methylsulfonyl)amino]benzamide GSK332377A (u19911-71-2)

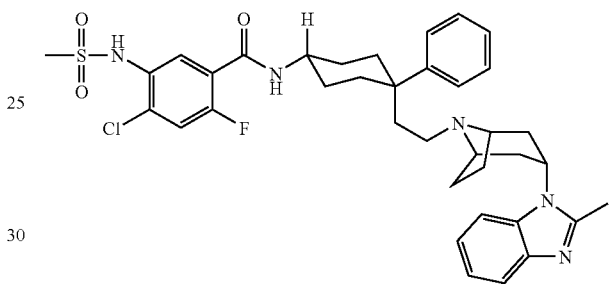

cis-4-Chloro-2-fluoro-N-(4-{2-[3-(2-methyl-1H-benzimidazol-1-yl)-8-azabicyclo[3.2.1]oct-8-yl]ethyl}-4-phenylcyclohexyl)-5-[(methylsulfonyl)amino]benzamide (20 mg, 57%) was obtained as white solid from cis-4-{2-[3-(2-methyl-1H-benzimidazol-1-yl)-8-azabicyclo[3.2.1]oct-8-yl]ethyl}-4-phenylcyclohexanamine (22 mg, 0.05 mmol), 2-chloro-4-fluoro-5-[(methylsulfonyl)amino]benzoic acid (14 mg, 0.05 mmol) and HATU (19 mg, 0.05 mmol), following the procedures outlined in Preparation 7. H¹NMR (400 MHz, CDCl₃) δ 8.25 (d, J=7.3 Hz, 1H), 7.65 (d, J=7.3 Hz, 1H), 7.37-7.27 (m, 6H), 7.23-7.12 (m, 3H), 6.66 (t, J=8.9 Hz, 1H), 4.70-4.65 (m, 1H), 4.02 (br, 1H), 3.30 (br, 2H), 3.08 (s, 3H), 2.57 (s, 3H), 2.44-2.37 (m, 2H), 1.98-1.88 (m, 15H), 1.73-1.61 (m, 4H), HRMS m/z (M+H)⁺ calcd 692.2828, obsd 692.2837.

Using a similar procedure, compounds of the formula

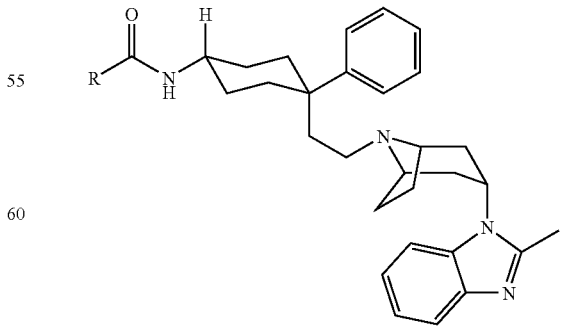

were prepared, wherein R are as defined in the table:

| R | H¹NMR(400 MHz, CDCl3) | HRMS m/z (M + H)⁺ |
|---|---|---|
| 4,6-dimethylpyrimidin-5-yl | δ 8.90(s, 1H), 7.63(d, J=7.7Hz, 1H), 7.38-7.32(m, 4H), 7.24-7.21(m, 2H), 7.18-7.10(m, 2H), 6.98(d, J=8.1Hz, 1H), 4.51(br, 1H), 4.13-4.08(m, 1H), 3.14(br, 2H), 2.54(s, 6H), 2.45(s, 3H), 2.23-2.15(m, 2H), 2.07-1.98(m, 4H), 1.92-1.88(m, 8H), 1.86-1.77(m, 4H), 1.52(d, J=7.9Hz, 2H). | calcd: 577.3655 obsd: 577.3635 |
| 3-sulfamoyl-2,4-dimethylphenyl | δ 7.70(d, J=8.1Hz, 1H), 7.60(d, J=7.5Hz, 1H), 7.37-7.31(m, 3H), 7.24-7.20(m, 2H), 7.16-7.09(m, 2H), 6.94-6.87(m, 2H), 5.59(br, 1H), 4.58-4.48(m, 1H), 4.14-4.05(m, 1H), 3.20(br, 2H), 2.53(s, 3H), 2.44(s, 3H), 2.32(s, 3H), 2.28-2.23(m, 3H), 2.06-2.04(m, 5H), 1.97-1.75(m, 2H), 1.53(d, J=7.9Hz,2H). | calcd: 654.3468 obsd: 654.3478 |
| 2,4-dimethylpyridin-3-yl | δ 8.34(d, J=5.2Hz, 1H), 7.65(d, J=7.5Hz, 1H), 7.38-7.33(m, 4H), 7.28-7.21(m, 2H), 7.19-7.11(m, 2H), 6.96(d, J=4.9Hz, 1H), 5.94(d, J=6.9Hz, 1H), 4.60-4.56(m, 1H), 4.12-4.11(m, 1H), 3.22(br, 2H), 2.57(s, 3H), 2.53(s, 3H), 2.34(s, 3H), 2.32-2.28(m, 2H), 2.04-2.02(m, 4H), 1.88-1.83(m, 10H), 1.75-1.70(m, 2H),1.58-1.56(m, 2H). | calcd: 576.3702 obsd: 576.3687 |
| 2-fluoropyridin-3-yl | δ 8.57(t, J=8.1Hz, 1H), 8.31(d, J=4.2Hz, 1H), 7.65(d, J=7.5Hz, 1H), 7.37-7.29(m, 6H), 7.23-7.11(m, 3H), 6.96-6.91(m, 1H), 4.65-6.40(m, 1H), 4.08-4.06(m, 1H), 3.25(br, 2H), 2.56(s, 3H), 2.41-2.33(m, 2H), 1.99-1.86(m, 14H), 1.75-1.73(m, 2H), 1.60-1.58(m, 2H). | calcd: 566.3295 obsd: 566.3279 |
| HO-C(CH3)2- | δ 7.65(d, J=7.2Hz, 1H), 7.35-7.29(m, 5H), 7.22-7.13(m, 3H), 7.00(d, J=8.0Hz, 1H), 4.65-4.59(m, 1H), 3.80-3.77(m, 1H), 3.23-3.22(br, 2H), 2.57(s, 3H), 2.39-2.31(m, 2H), 2.00-1.81(m, 15H), 1.65-1.54(m, 4H), 1.48(s, 6H). | calcd: 529.3543 obsd: 529.3531 |
| HO-C(CF3)2- | δ 7.65(d, J=7.7Hz, 1H), 7.37-7.30(m, 5H), 7.25-7.15(m, 3H), 6.80(br, 1H), 4.67(br, 1H), 3.95-3.93(m, 1H), 3.49(br, 2H), 2.59(s, 3H), 2.43(br, 2H), 1.94-1.88(m, 13H), 1.70-1.65(m, 6H). | calcd: 637.2977 obsd: 637.3000 |
| HOCH2-C(CH3)2- | δ 7.56(d, J=7.7Hz, 1H), 7.35-7.27(m, 5H), 7.21-7.13(m, 3H), 6.61(d, J=6.6Hz, 1H), 4.64-4.59(m, 1H), 3.83-3.81(m, 1H), 3.59(s, 2H), 3.22(br, 2H), 2.56(s, 3H), 2.37-2.29(m, 2H), 1.94-1.80(m, 14H), 1.63-1.55(m, 4H), 1.19(s, 6H). | calcd: 543.3699 obsd: 543.3687 |

Using a similar procedure, compounds of the formula

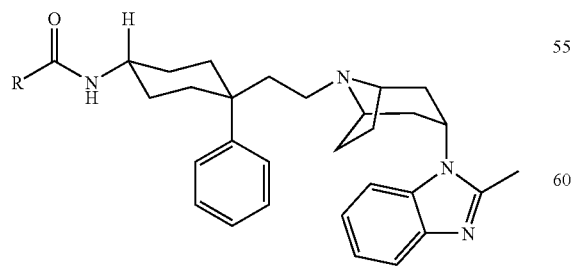

were prepared, wherein R are as defined in the table:

| R | H¹NMR (400 MHz, CD3OD) | HRMS m/z (M + H)+ |
|---|---|---|
| ![sulfonamide with Cl] | δ 8.35(br, 1H), 7.86-7.84(m, 1H), 7.56(br, 2H), 7.38(br, 5H), 7.18(br, 2H), 5.35(br, 1H), 4.73(br, 1H), 4.58(br, 4H), 3.99(br, 1H), 3.30(m, 2H), 2.52(s, 3H), 2.42-2.40(m, 3H), 1.96-1.85(m, 8H), 1.73-1.65(m, 5H), 1.39-1.36(m, 2H). | calcd: 660.2775 obsd: 660.2798 |
| ![sulfonamide with di-Cl] | δ 8.02(d, J=8.7Hz, 1H), 7.52(d, J=8.6Hz, 2H), 7.43-7.34(m, 5H), 7.18-7.15(m, 3H), 4.79-4.74(m, 1H), 4.00-3.97(m, 1H), 3.30(br, 3H), 2.54(s, 3H), 2.46-2.38(m, 2H), 2.06-2.20(m, 2H), 1.96-1.79(m, 7H), 1.71-1.65(m, 7H), 1.43-1.37(m, 2H) | calcd: 694.2385 obsd: 694.2413 |
| ![sulfonamide with dimethyl] | δ 7.84(d, J=8.2Hz, 1H), 7.52(d, J=6.8Hz, 1H), 7.43-7.34(m, 5H), 7.20-7.15(m, 4H), 4.81-4.72(m, 1H), 4.01-3.98(m, 1H), 3.30(br, 2H), 2.54(s, 6H), 2.46-2.38(m, 2H), 2.28(s, 3H), 2.06-1.90(m, 9H), 1.78-1.66(m, 6H), 1.42-1.28(m, 2H). | calcd: 654.3478 obsd: 654.3493 |

Preparation 19 cis-Benzyl methyl(4-{2-[3-(2-methyl-1H-benzimidazol-1-yl)-8-azabicyclo[3.2.1]oct-8-yl]ethyl}-4-phenylcyclohexyl)carbamate GSK259211A (u19911-14-39)

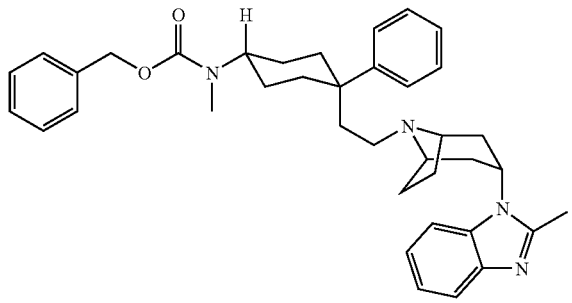

To a stirred solution of cis-benzyl methyl[4-(2-oxoethyl)-4-phenylcyclohexyl]carbamate (18.6 mg, 0.05 mmol) and 1-(8-azabicyclo[3.2.1]oct-3-yl)-2-methyl-1H-benzimidazole (14 mg, 0.05 mmol) in 2 mL of dichloromethane was added MP-triacetoxyborohydride resin (50 mg, 0.1 mmol). After the reaction was shaken overnight, the polymer beads were filtered out. Evaporation of the solvents afforded cis-benzyl methyl(4-{2-[3-(2-methyl-1H-benzimidazol-1-yl)-8-azabicyclo[3.2.1]oct-8-yl]ethyl}-4-phenylcyclohexyl)carbamate as foam (14 mg, 48%). The purity was >95% by LC-MS. H¹NMR (400 MHz, CDCl3) δ 7.70 (d, J=7.5 Hz, 1H), 7.35-7.29 (m, 9H), 7.24-7.14 (m, 4H), 5.14 (s, 2H), 4.98 (br, 2H), 4.02 (br, 1H), 3.53 (br, 2H), 2.93-2.88 (m, 3H), 2.59 (s, 3H), 2.18-2.00 (m, 9H), 1.97-1.82 (m, 4H), 1.71-1.69 (m, 6H). LCMS m/z (M+H)+ calcd 591.4, obsd 591.4.

Using a similar procedure, the following compounds were prepared:

| structure | LCMS m/z (M + H)+ | |
|---|---|---|
| | calcd | obsd |
| 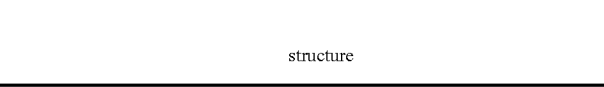 | 611.4 | 611.4 |

-continued
| structure | LCMS m/z (M + H)+ | |
|---|---|---|
| | calcd | obsd |
| 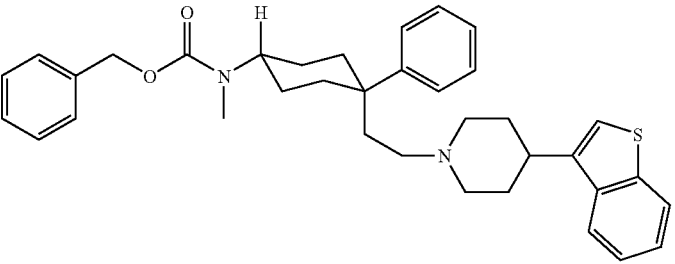 | 568.3 | 568.3 |
| 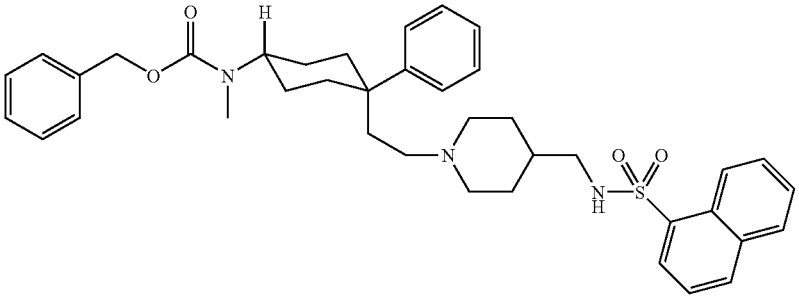 | 654.3 | 654.3 |
| 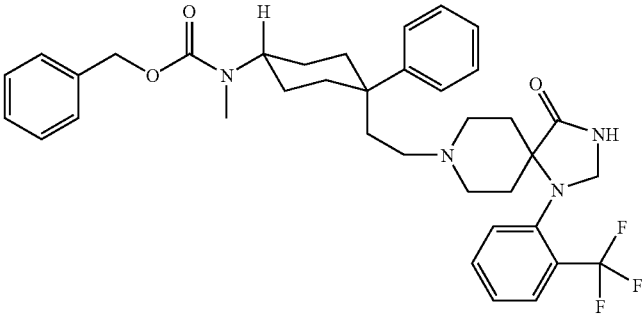 | 649.3 | 649.2 |
| 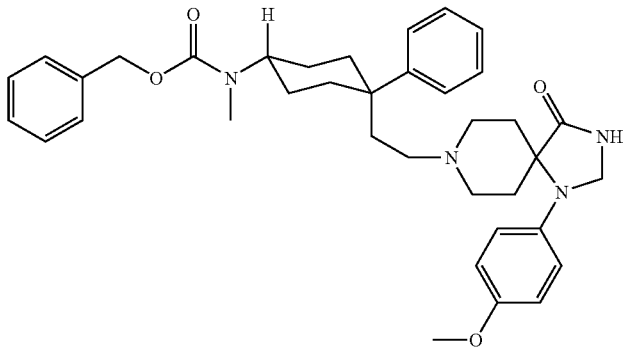 | 611.4 | 611.3 |

-continued
| structure | LCMS m/z (M + H)+ | |
|---|---|---|
| | calcd | obsd |
| 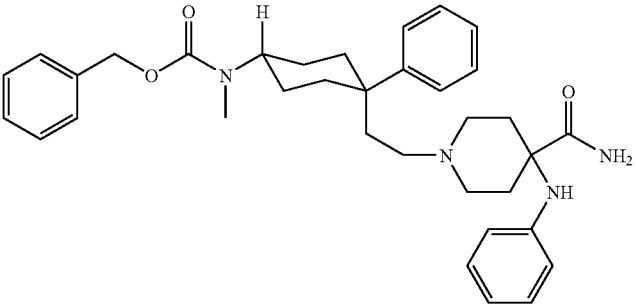 | 569.3 | 569.4 |
| 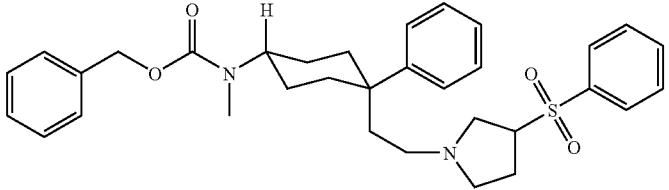 | 561.3 | 561.2 |
| 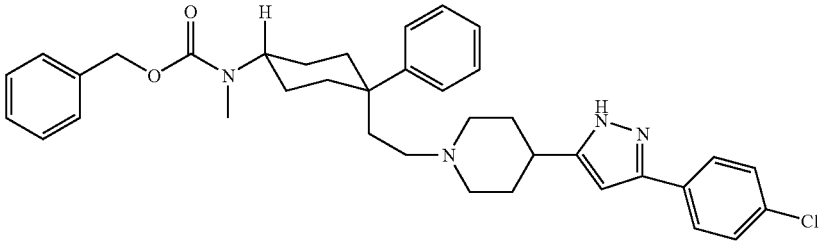 | 611.3 | 611.4 |
| 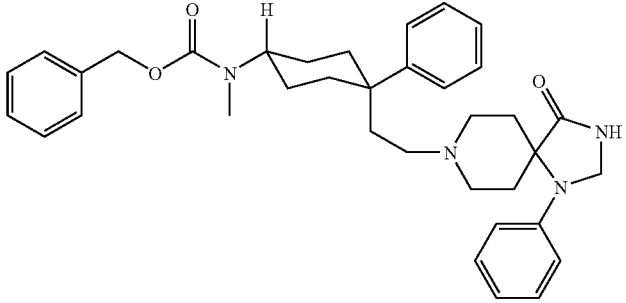 | 581.3 | 581.4 |
| 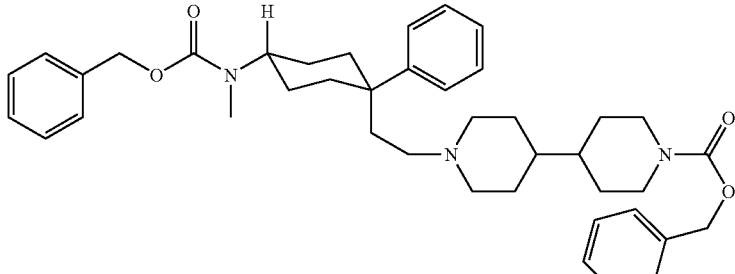 | 652.4 | 652.3 |

-continued

| structure | LCMS m/z (M + H)+ | |
|---|---|---|
| | calcd | obsd |
| 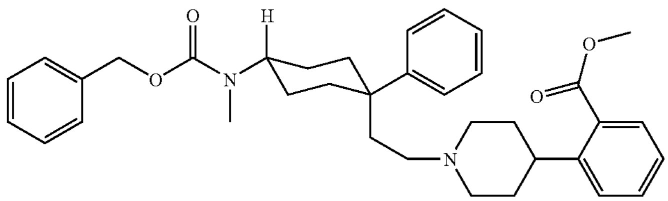 | 569.3 | 569.3 |
| 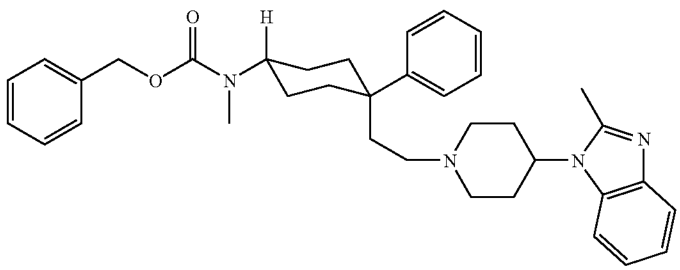 | 565.3 | 565.5 |
| 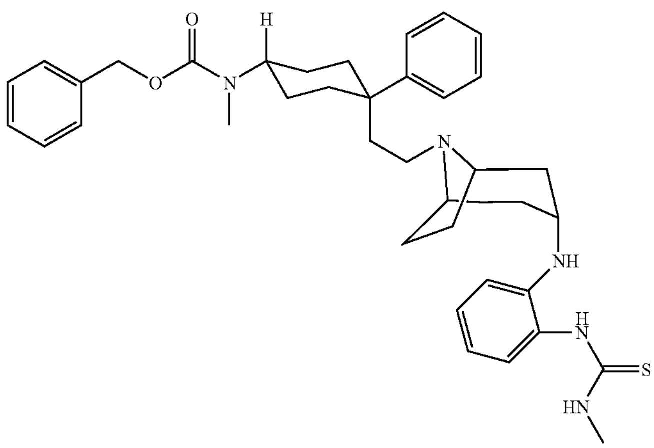 | 640.4 | 640.5 |
| 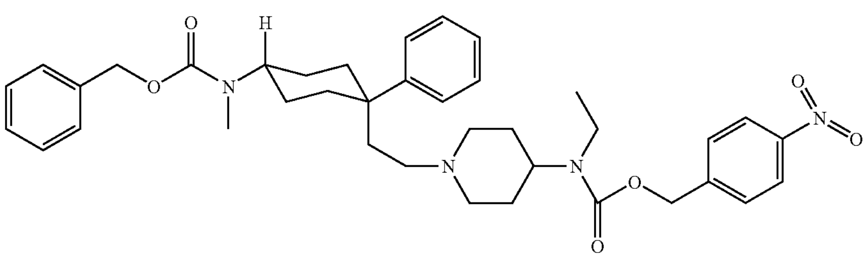 | 641.4 | 641.3 |
| 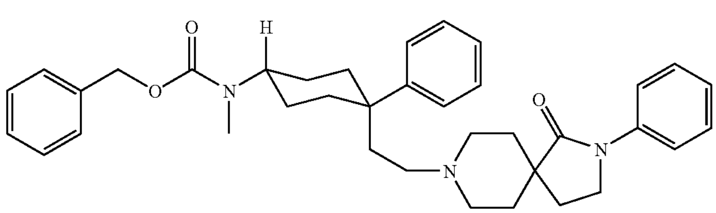 | 580.4 | 580.5 |

-continued
| structure | LCMS m/z (M + H)+ | |
|---|---|---|
| | calcd | obsd |
| 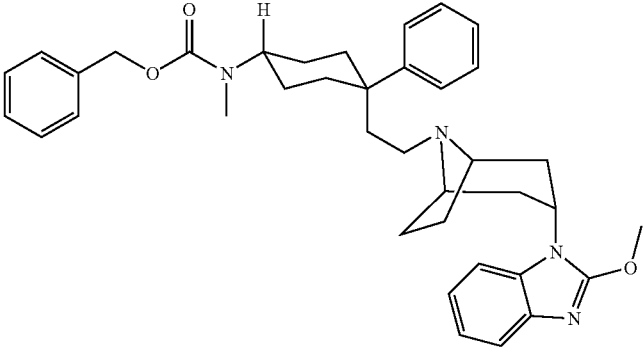 | 607.4 | 607.4 |
| 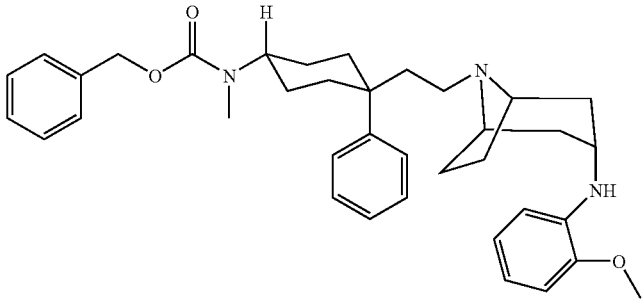 | 582.4 | 582.4 |
| 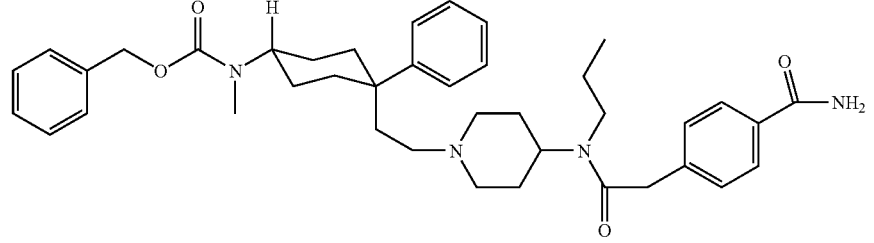 | 653.4 | 653.5 |
| 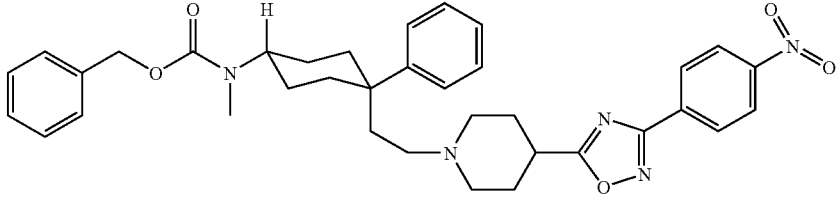 | 638.3 | 638.3 |
| 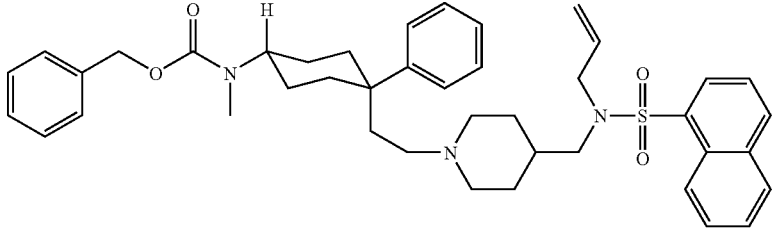 | 694.4 | 694.3 |

-continued

| structure | LCMS m/z (M + H)+ | |
|---|---|---|
| | calcd | obsd |
| 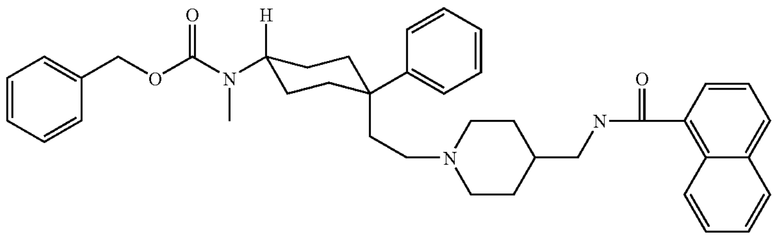 | 618.4 | 618.4 |
| 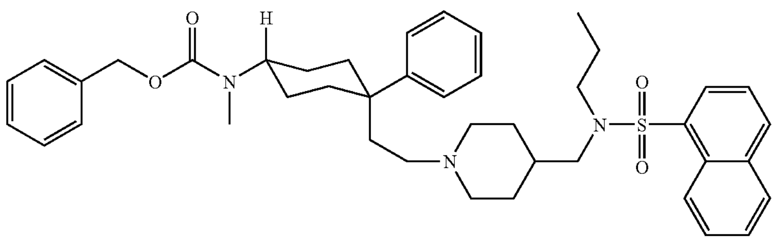 | 696.4 | 696.2 |
| 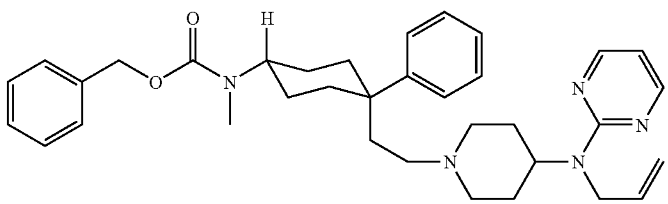 | 568.4 | 568.5 |
| 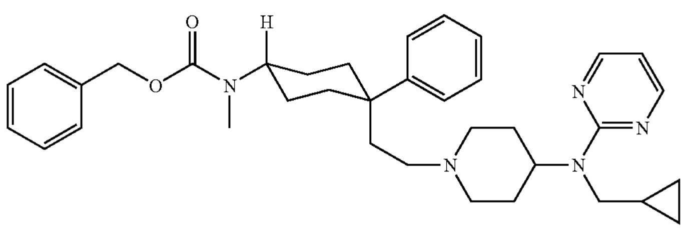 | 582.4 | 582.4 |
| | 567.4 | 576.5 |
| | 567.4 | 567.4 |

-continued
| structure | LCMS m/z (M + H)+ | |
|---|---|---|
| | calcd | obsd |
| 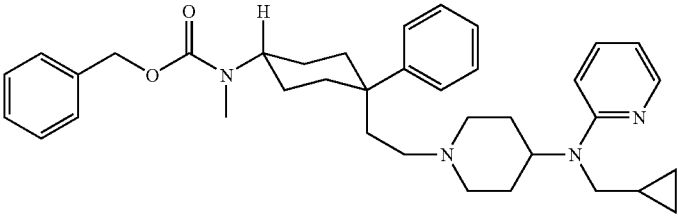 | 581.4 | 581.5 |
| 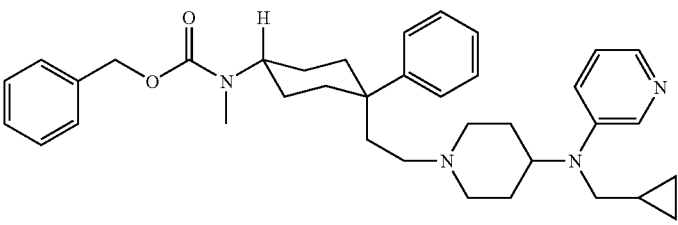 | 581.4 | 581.5 |
| 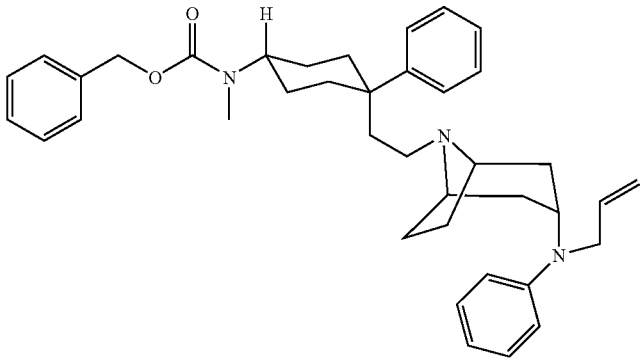 | 592.4 | 592.3 |
| 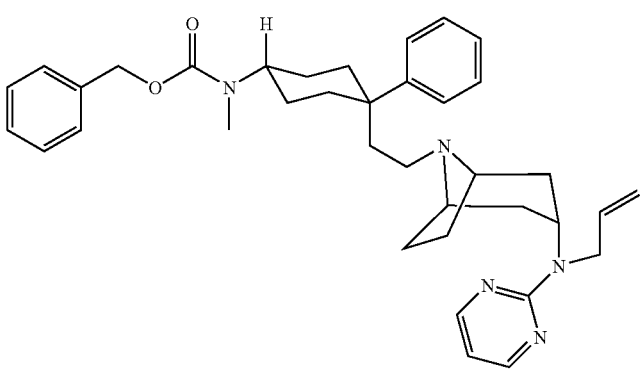 | 594.4 | 594.5 |

-continued
| structure | LCMS m/z (M + H)+ | |
|---|---|---|
| | calcd | obsd |
| 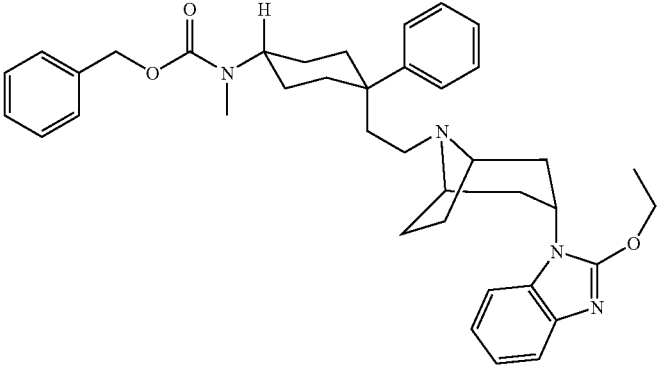 | 582.4 | 582.4 |
| 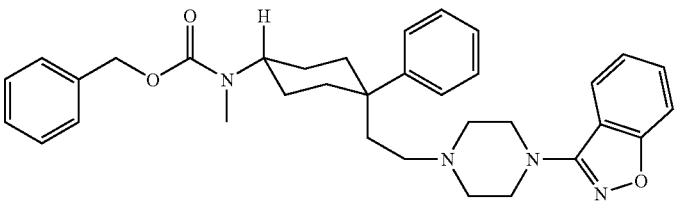 | 553.3 | 553.1 |
| 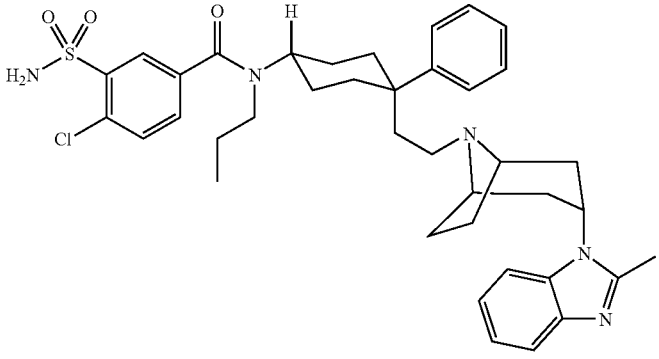 | 702.3 | 702.0 |
| 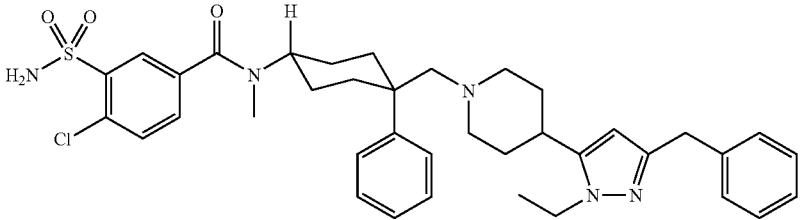 | 688.3 | 688.3 |
| 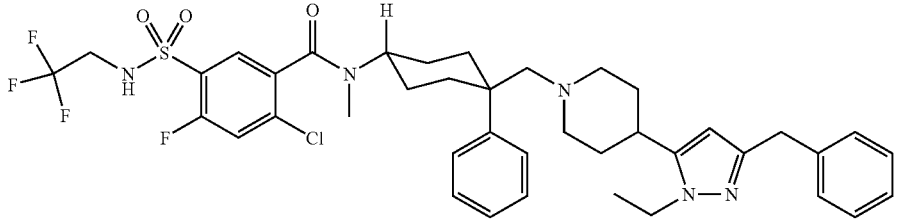 | 788.3 | 788.3 |

-continued

| structure | LCMS m/z (M + H)+ | |
|---|---|---|
| | calcd | obsd |
| 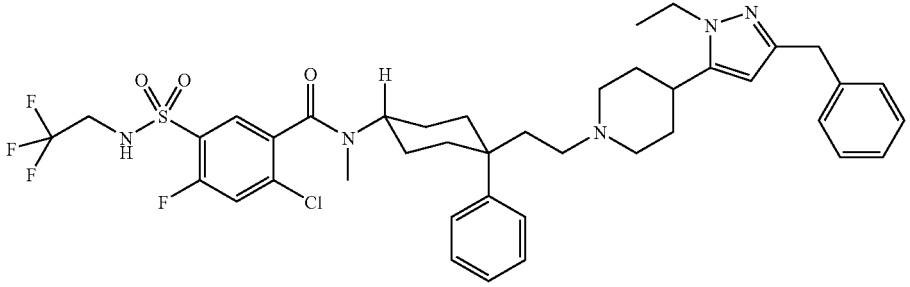 | 802.3 | 802.3 |

Preparation 20 cis-Methyl (2E)-3-(4-{benzyl[(benzyloxy)carbonyl]amino}-1-phenylcyclohexyl)prop-2-enoate

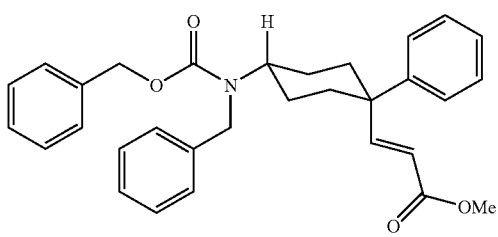

At 0° C., to a stirred solution of methyl diethylphosponacetate (1.83 g, 8.7 mmol) in THF (25 mL) was added NaH (348 mg, 60% oil suspension, 8.7 mmol) portionwise. The elution of hydrogen gas was observed. The mixture was allowed to stir for 10 minutes at room temperature before allowed to add a solution of cis-benzyl benzyl(4-formyl-4-phenylcyclohexyl)carbamate (2.48 g, 5.8 mmol) in THF (25 mL). After a 4-hour stirring, the reaction was quenched with saturated ammonium chloride solution and concentrated down to half of the original volume. The remained mixture was diluted with dichlormethane (100 mL) and layers were separated. The aqueous layer was extracted with dichloromethane (2×30 mL). The combined extracts were washed with saturated sodium bicarbonate solution, brine and dried over sodium sulfate. Evaporation of solvents and flash chromatography (hexane/EtOAc, 4/1) afforded cis-methyl (2E)-3-(4-{benzyl[(benzyloxy)carbonyl]amino}-1-phenylcyclohexyl)prop-2-enoate as an oil (0.86 g, 46%) (recovered the starting material, 0.84 g). H$^1$NMR (400 MHz, CDCl$_3$) δ 7.46-7.18 (m, 15H), 6.92 (d, J=16.3 Hz, 1H), 5.81 (d, J=16.3 Hz, 1H), 5.20-5.14 (m, 2H), 4.45 (br, 2H), 4.24 (br, +3.93 (br, 1H, rotational isomer), 3.75 (s, 3H), 2.24 (d, J=12.6 Hz, 2H), 1.90-1.66 (m, 6H). HRMS m/z (M+H)+ calcd 484.2503, obsd 484.2488.

Preparation 21 cis-Methyl 3-(4-{benzyl[(benzyloxy)carbonyl]amino}-1-phenylcyclohexyl)propanoate

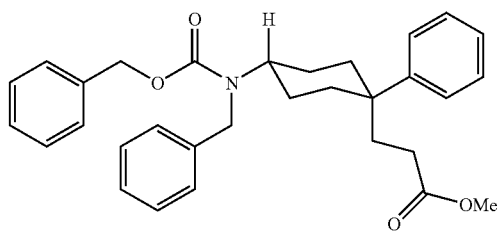

cis-Methyl (2E)-3-(4-{benzyl[(benzyloxy)carbonyl]amino)-1-phenylcyclohexyl)prop-2-enoate (0.86 g, 1.78 mmol) was stirred in a mixed EtOH/THF (15 mL/5 mL) in the presence of catalytic amount of 10% Pd/C under hydrogen atmosphere for 5 hours. The catalyst was removed by filtration and the filtrate was concentrated down to give an oil, which was subjected to Cbz protection as exemplified in Preparation 1. cis Methyl 3-(4-{benzyl[(benzyloxy)carbonyl]amino}1-phenylcyclohexyl)propanoate was obtained as an oil (510 mg, 60%). H$^1$NMR (400 MHz, CDCl3) δ 7.46-7.44 (m, 1H), 7.38-7.22 (m, 12H), 7.20-7.16 (m, 2H), 5.16 (br, 2H), 4.53 (br, 2H), 4.03 (br, 1H), 3.56 (s, 3H), 2.06-1.93 (m, 4H), 1.87-1.81 (m, 4H), 1.68 (br, 4H). HRMS m/z (M+H)+ calcd 486.2641, obsd 486.2644.

Preparation 22 cis-Benzyl Menzyl(4-{3-[3-(2-methyl-H-benzimidazol-1-yl)-8-azabicyclo[3.2.1]oct-8-yl]propyl}-4-phenylcyclohexyl)carbamate

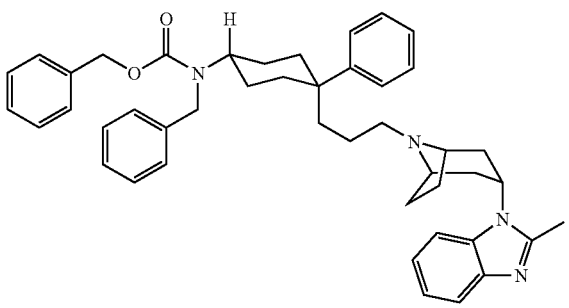

At −78° C., to a stirred solution of cis methyl 3-(4-benzyl[(benzyloxy)carbonyl]amino}-1-phenylcyclohexyl)propanoate (510 mg, 1.05 mmol) in dichloromethane (20 mL) was added Dibal-H (2 mL, 1.0 M in toluene). The reaction was allowed to stir for 5 hours at this temperature before quenched with methanol. After the mixture was brought up to the room temperature, 10 mL of saturated Rochelle's salt solution was added and the mixture was stirred for further two hours. Layers were separated and the aqueous layer was extracted with dichloromethane. The combined extracts were washed with saturated sodium bicarbonate solution, brine and dried over sodium sulfate. Evaporation of solvents afforded an oil (470 mg, quant.), which was used for the next step.

cis-Benzyl benzyl(4-{3-[3-(2-methyl-1H-benzimidazol-1-yl)-8-azabicyclo[3.2.1]oct-8-yl]propyl}-4-phenylcyclohexyl)carbamate (498 mg, 73%) was obtained as foam from the aldehyde (470 mg, 1 mmol, prepared from above) and 1-(8-azabicyclo[3.2.1]oct-3-yl)-2-methyl-1H-benzimidazole dihydrochloride (368 mg, 1.05 mmol), following the procedures outlined in Preparation 5. H$^1$NMR (400 MHz, CDCl3) δ 7.67 (d, J=7.2 Hz, 1H), 7.38-7.16 (m, 14H), 7.25-7.13 (m, 4H), 5.30 (br, 2H), 4.71-4.53 (m, 3H), 3.84 (br, 1H), 3.19 (br, 2H), 2.58 (s, 3H), 2.38-2.30 (m, 2H), 2.06-2.00 (m, 5H), 1.97-1.63 (m, 13H), 1.01 (br, 2H). HRMS m/z (M+H)$^+$ calcd 681.4164, obsd 681.4169.

Preparation 23

4-{3-[3-(2-methyl-1H-benzimidazol-1-yl)_-8-azabicyclo[3.2.1]oct-8-yl]propyl}-4-phenylcyclohexanamine

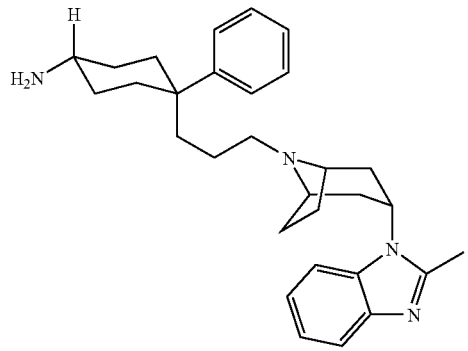

cis-4-{3-[3-(2-Methyl-1H-benzimidazol-1-yl)-8-azabicyclo[3.2.1]oct-8-yl]propyl}-4-phenylcyclohexanamine was obtained as solid (330 mg, quant.) from cis-benzyl benzyl(4-{3-[3-(2-methyl-1H-benzimidazol-1-yl)-8-azabicyclo[3.2.1]oct-8-yl]propyl}-4-phenylcyclohexyl)carbamate (497 mg, 0.73 mmol), following the procedures outlined in Preparation 6. The desired product was used without any purification.

Preparation 24 cis-3-(aminosulfonyl)-4-chloro-N-(4-{3-[3-(2-methyl-1H-benzimidazol-1-yl)-8-azabicyclo[3.2.1]oct-8-yl]propyl}-4-phenylcyclohexyl)benzamide GSK164326A (u19394-109-6)

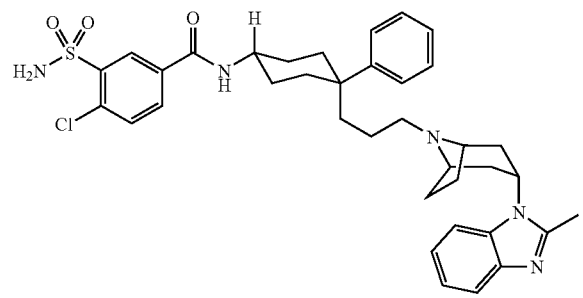

cis-3-(Aminosulfonyl)-4-chloro-N-(4-{3-[3-(2-methyl-1H-benzimidazol-1-yl)-8-azabicyclo[3.2.1]oct-8-yl]propyl}4-phenylcyclohexyl)benzamide (56 mg, 83%) was obtained as a solid from cis 4-{3-[3-(2-methyl-1H-benzimidazol-1-yl)-8-azabicyclo[3.2.1]oct-8-yl]propyl}-4-phenylcyclohexanamine (46 mg, 0.1 mmol), 3-(aminosulfonyl)-4-chlorobenzoic acid (24 mg, 0.1 mmol) and HATU (38 mg, 0.1 mmol), following the procedures outlined in Preparation 7. H$^1$NMR (400 MHz, CDCl3) δ 8.20 (s, 1H), 7.94 (d, J=7.3 Hz, 1H), 7.50 (t, J=9.0 Hz, 2H), 7.48-7.29 (br, 1H), 7.14-7.10 (m, 2H), 6.63 (d, J=6.9 Hz, 1H), 4.70 (m, 1H), 3.93 (br, 1H), 3.27 (br, 2H), 2.53 (s, 3H), 2.40-2.32 (m, 2H), 2.10-2.00 (m, 9H), 1.90-1.79 (m, 6H), 1.74-1.64 (m, 4H), 1.05 (br, 2H). HRMS m/z (M+H)$^+$ calcd 674.2932, obsd 674.2928.

Using a similar procedure, compounds of the formula were prepared, wherein

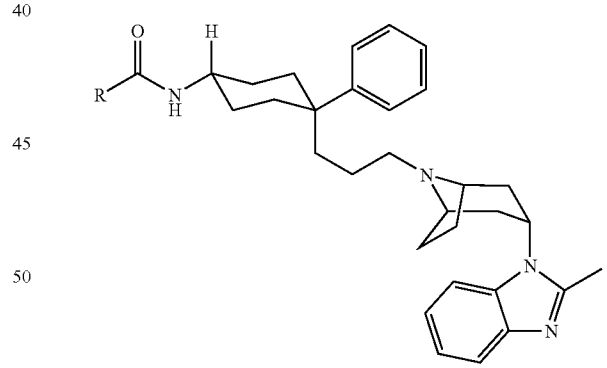

Rs are as defined in the table:

| R | H$^1$NMR (400 MHz, CDCl3) | HRMS m/z (M + H)$^+$ |
|---|---|---|
| ![pyrimidinyl] | δ 8.89(s, 1H), 7.63(d, J=7.6Hz, 1H), 7.36-7.32(m, 4H), 7.29-7.22(m, 1H), 7.18(br, 1H), 7.16-7.11(m, 2H), 6.33(d, J=7.7Hz, 1H), 4.60-4.56(m, 1H), 4.11-4.07(m, 1H), 3.18(br, 3H), 2.53(s, 3H), 2.51(s, 6H), 2.33-2.25(m, 2H), 2.07-2.00(m, 9H), 1.95-1.81(m, 4H), 1.75-1.61(m,6H), 1.08(br, 2H). | calcd: 591.3811 obsd: 591.3829 |

-continued

| R | H¹NMR (400 MHz, CDCl3) | HRMS m/z (M + H)⁺ |
|---|---|---|
| 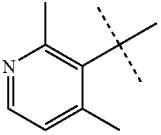 | δ 8.33(d, J=5.2Hz, 1H), 7.65(d, J=7.3Hz, 1H), 7.37-7.22(m, 5H), 7.20-7.12(m, 4H), 6.94(d, J=5.3Hz, 1H), 5.94(d, J=8.0Hz, 1H), 4.63-4.58(m, 1H), 4.10-4.08(m, 1H), 3.20(br, 2H), 2.56(s, 3H), 2.55(s, 3H), 2.32(s, 3H), 2.31-2.28(m, 3H), 2.08-1.84(m, 14H), 1.76-1.60(m, 6H), 1.11-1.08(m, 2H). | calcd: 590.3859 obsd: 590.3856 |
| 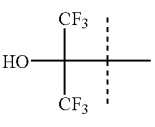 | δ 7.64(d, J=8.5Hz, 1H), 7.36-7.28(m, 5H), 7.22-7.15(m, 3H), 6.98(d, J=7.8Hz, 1H), 4.65(br, 1H), 3.95-3.93(m, 1H), 3.25(br, 2H), 2.57(s, 3H), 2.33(br, 2H), 2.08(br, 4H), 1.92-1.89(m, 8H), 1.77-1.65(m, 6H), 1.08(br, 2H). | calcd: 651.3133 obsd: 651.3118 |
| 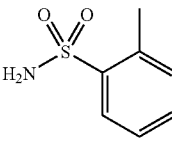 | δ 7.76(d, J=8.1Hz, 1H), 7.61(d, J=7.0Hz, 1H), 7.35-7.32(m, 4H), 7.29-7.26(m, 1H), 7.21-7.11(m, 3H), 7.00(d, J=8.2Hz, 1H), 6.38(d, J=7.4Hz, 1H), 5.67(br, 1H), 4.65-4.58(m, 1H), 4.08(br, 1H), 3.21(br, 2H), 2.53(s, 3H), 2.48(s, 3H), 2.33(s, 3H), 2.31-2.30(m, 3H), 2.06-2.00(m, 8H), 1.93-1.61(m, 10H), 1.07(br, 2H). | calcd: 668.3634 obsd: 668.3625 |

BIOLOGICAL DATA

The following definitions apply:

| $IC_{50}$ | Concentration of compound that displaces 50% of radioligand |
|---|---|
| $pIC_{50}$ | The determined $IC_{50}$ value expressed as $-log10(IC_{50})$ |

CC-Chemokine Receptor-5 Binding by Scintillation Proximity Assay (CCR5 SPA)

Scintillation Proximity Assay for the Human CC-Chemokine Receptor, CCR-5

This protocol describes a high-throughput screen using SPA binding to identify compounds that inhibit binding of $^{125}$I-MIP1α to the human CCR5 chemokine receptor.

CCR5 is a G protein-coupled receptor that binds the natural chemokine ligands, MIP1α, MIP1β and RANTES. CCR5 acts as a co-receptor with CD4 for entry of HIV-1 into human T-cells and monocytes. Chemokines also play a role in acute and chronic inflammatory processes. Chemokines are soluble proteins produced and released by a wide variety of cell types during the initial phase of a host response to a foreign substance entering the body.

Human CCR5 receptors were expressed in Chinese Hamster Ovary (CHO) cells, registration # 12025. Cells were grown in suspension and a 50 to 80 ml CCR5 cell pellet was prepared. Membrane preparation: 1) Weigh pellet; 2) Prepare an ice-cold 50 mM HEPES buffer, containing 0.0025 mg/ml Pefabloc, 0.0001 mg/ml Pepstatin A, 0.0001 mg/ml Leupeptin, 0.0001 mg/ml Aprotinin (protease inhibitor cocktail), pH 7.4; 3) Homogenize pellet in 5 volumes of HEPES buffer; 4) Homogenize again with a glass homogenizer 10 to 20 strokes; 5) Centrifuge homogenate at 18,000 rpm in a F28/36 rotor using a Sorvall RC26 PIUS refrigerated Centrifuge for 30 minutes; 6) Discard supernatant and resuspend pellet in 3 volumes of HEPES buffer; 7) Homogenize and centrifuge again using steps 4-6, 2 more times; 8) Reweigh pellet and homogenize in 3× weight-to-volume of HEPES buffer; 9) Aliquot 0.5 to 1.5 ml of the membrane preparation into small vials and store at −80 degrees Centigrade; 10) Determine the protein concentration of the membrane preparation using the Bio-Rad or BCA method; 11) The membrane homogenate will need to be characterized for the assay conditions a.) Protein concentration; b.) Optimal protein-to-bead ratio in SPA; and c.) Saturation curve to determine Kd and Bmax in SPA The saturation curve binding experiment is performed by adding varying amounts of [$^{125}$I]MIP1α (0-8.5 nM to membranes and beads in concentrations chosen from the optimal protein/bead ratio. The data is analyzed using a non-linear curve-fitting program. The $K_d$ and Bmax are derived from the curve.

Bacitradn 50 mg/ml is dissolved in deionized water, brought to a boil for 5 minutes (to destroy protease activity) and cooled. Prepared 1 ml aliquots and store at −80° C.

Protease inhibitor cocktail is prepared by dissolving 25 mg/ml of Pefabloc, 1 mg/ml of Leupeptin, 1 mg/ml of Aprotinin and 1 mg/ml of Pepstatin A in 100% DMSO. The cocktail can be aliquoted and stored frozen at −20° C. until needed.

Sigmacote: Any reagent bottles and reservoirs that come in contact with the radioligand are treated with Sigmacote to reduce sticking. Rinse containers with undiluted Sigmacote; rinse with deionized water several times, and allow to air dry before using.

Color Quench Assay-[$^{125}$I] SPA PVT color quench kit, Cat. No. RPAQ 4030, Amersham Ltd. A color quench curve is generated for each Packard TopCount and is stored in each counting protocol specific for the assay. This is done to prevent colored compounds from quenching the scintillation counts.

Compounds Preparation:

Compounds for a single concentration determination (One Shots) are delivered in 96 well Packard Optiplates containing 1 μl of compound in 100% DMSO in columns A1-H10 (80 compounds/plate). Column A11 to H11 is used for total binding (Bo) (vehicle-5 μl of the appropriate DMSO concentration) and column A12 to D12 is used for determination of nonspecific binding. No further preparation is required.

Compounds for concentration-response curves (10 points) are delivered in 96-Packard Optiplates containing 1 μl of compound in 100% DMSO in columns A1-H10. A 10-point concentration-response curve is desired for each compound with a starting high concentration of 30 μM (in the assauy final). Column A11 to H11 is used for total binding (Bo) (vehicle-5 μl of the appropriate DMSO concentration) and column A12 to D12 is used for determination of nonspecific binding. No further preparation is required Materials:

1 M HEPES, pH 7.4, Gibco, Cat. No. 15360-080

Bacitracin, Sigma Catalog. Number. B-0125

Bovine Serum Albumin, Sigma, Cat. No. A-7888

$MgCl_2$, J. T. Baker 2444-01

$CaCl_2$, Sigma, Cat. No. C5080

MIP1α, Peprotech, Cat. No. 300-08

Sigmacote, Sigma, Cat. No. SL2

Scintillation Proximity Beads, Wheat Germ Agglutinin, Amersham, Cat No. RPNQ 0001

[$^{125}$I]MIP1α, NEN (#NEX298)

Packard 96 well flat-bottom Optiplate, Cat. No. 6005190

Falcon 96 well round-bottom plate, Cat. No. 3077

TOPSEAL-S, Packard, Cat. No. 6005161

Dimethyl Sulfoxide, EM Science, Cat. No. MX1458-6

Siliconized Pipette tips, Accutip, volume 200-1300 uL, Cat. No. P5048-85

Siliconized Pipette tips, Bio Plas, Inc., volume 1-200 uL, Cat. No. 60828-908

Reagent Reservoir, Elkay, Cat. No. 175-RBAS-000

Assay Buffer Preparation:

50 mM HEPES buffer pH 7.4, 1 mM $CaCl_2$, 5 mM MgCl2 (this can be made ahead as a 100× stock), 1% BSA, 0.5 mg/ml Bacitracin, Protease inhibitor Cocktail (see preparation above) 100 uL/100 ml, DMSO is added to equal a final concentration of 2% per well (includes compound % DMSO) if needed.

Experimental Details:

[$^{125}$I]MIP1α Preparation:

Prepared radioligand dilutions in container treated with Sigmacote

Reconstitute each 50 μCi vial with 0.5 ml of deionized water and store at 4° C.

Specific Activity=2,000 Ci/mmol

Add ~60,000 cpm (0.17 nM) to each assay well in 50 uL

Bo:

Make a 20% DMSO solution and add 5 uls of this to each well in col A11-H11. This gives a final 2% DMSO concentration for the well when added to the 1% in the assay buffer.

NSB:

Make a stock dilution of MIP1α at 100 uM using deionized water; aliquot and freeze. Dilute the MIP-1α stock solution to a concentration of 2 μM in the same 20% DMSO solution used above and add 5 μl to the wells in column A12 to D12 to give a final assay concentration of 100 nM. Prepare this in a Sigmacote-treated container Membrane and SPA Bead Preparation—

The final assay concentration for the membrane is 15 μg per well. SPA beads are prepared by adding 5 ml of assay buffer to a 500 mg vial. The final concentration of SPA beads in the assay is 0.25 mg/well. Membranes and beads are premixed as a 1:1 (membrane:bead) mixture and maintained at mixture at 4° C. with constant stirring. 50 μl of the mixture is added to each assay well. After all reagents have been added to the plates (total assay volume 100 μl), shake plates for 4 hours at room temperature. After 4 hours, place the plates on the TopCount in a count the plates on the TopCount for 30 sec per well using an appropriate program (i.e., one with a quench curve established for the conditions of the assay.

Data Reduction:

Data reduction is performed using the Microsoft Excel Addins Robofit or Robosage.

For single concentration assays (One Shots), the result of each test well is expressed as % inhibition using the following formula: $100*(1-(U1-C2)/(C1-C2))$. Where U1 is the unknown sample in cpm observed in a particular well, C1 is the average of column 12 cpm observed in the absence of any added inhibitor, and C2 is the average of column 11 cpm observed in the presence bf 1 μM of MIP1α.

For concentration-response assays, the result of each test well is expressed as % B/Bo (% total specific binding) using the following formula: $100*(U1-C2)/C1-C2)$. Curves were generated by plotting the % B/Bo versus the concentration and the $IC_{50}$ is derived using the equation $y=Vmax*(1-(x^n/(k^n+x^n)))$.

Controls and Standards:

Each plate contains 12 wells of total binding (column A11-H11). The cpm/well are averaged and are used in data reduction as value C1. Each plate also contains 4 wells of nonspecific binding (wells A12-D12). The counts of these wells are averaged and used in data reduction as value C2.

A standards plate is included in each experiment. This plate contains a 14-point concentration-response curve (in triplicate) for the standard compound MIP1α at a starting concentration of 1 μM. The average historical $pK_i$ obtained with MIP1α is 7.6.

The relevant biological response field for a single concentration (One Shots) is % inhibition. Inhibition values of >40 or >50% were considered positive responses.

The relevant biological response field for a concentration-response experiment is $pK_i$ HOS Assay (Also referred to as HOS-LTR-Luciferase Assay)

Materials

DMEM (GibcoBRL # 10564-011)

Trpsin-EDTA (GibcoBRL #25300-054)

Heat inactivated Fetal Bovine Serum (FBS) (Hyclone # SH30070.03)

96-well, black-walled, clear-bottom, tissue culture-treated plates (Costar # 3904)

96-well, clear-walled, clear-bottom tissue culture-treated plates (Costar # 3598)

Phosphate Buffered Saline (PBS) (GibcoBRL #14190-144)

Dimethyl Sulfoxide (DMSO) (Sigma # D2650)

Luclite Luciferase Reporter assay (Packard #6016911)

HOS-CD4.CCR5-LTR-Luciferase (Bioresource Registration # 21164): Human Osteosarcoma cell line engineered to overexpress human CD4 and human CCR5 (AIDS Repository cat# 3318) stably transfected with HIV-1-LTR-Luciferase reporter.

ADVANCED PREPARATION

Growth and Maintenance of the HOS-CD4.CCR5-LTR-Luciferase Cell Line:

The cells were propagated in DMEM containing 2% FBS. Cells were split by standard trypsinization when confluency reached 80% (roughly every 2 to 3 days).

Titering of Virus Stocks:

HIV-1 virus stocks were titered in the assay system in order to obtain an estimate of the number of infectious particles per unit volume (described as RLU/ml). Virus stocks were diluted into DMEM containing 2% FBS and assayed as described in the "procedure" section below.

Procedure

Black-walled 96-well tissue culture plates were seeded with HOS-CD4.CCR5-LTR-Luciferase @ 0.6 to $1.2 \times 10^3$ cells per well in 50 ul DMEM containing 2% FBS and placed in a humidified incubator @ 37° C., 5% $CO_2$ overnight. The following day, test compounds were titrated 4-fold at 2× the final concentration in DMEM+2% FBS+0.2% DMSO. 50 µl of titrated compound was transferred to the HOS cells and the plates were placed in a humidified incubator at 37° C., 5% $CO_2$ for 1 hr. An additional 60 ul of 2× titrated compound was transferred to a clear-walled 96-well tissue culture plate and 60 ul of HIV (diluted to appropriate m.o.i.) was added to each well and thoroughly mixed. 100 ul of the HIV/compound mixture was transferred to the black-walled plates containing 100 ul of cells/compound. The plates were placed in a humidified incubator at 37° C., 5% $CO_2$ for 72 hr Following the 72 hour incubation, 150 ul of supernatant was removed and 50 ul of reconstituted LUCLITE (kit reagent) was added to each well. Each plate was sealed and read in a Topcount (Packard) luminometer at 1 s/well.

Data Reduction

Relative Light Units (RLU) were expressed as % control (RLU at drug [ ]/RLU no drug)*100=% Control $IC_{50}$ values were determined by any one of the following four nonlinear regression models:

$y = V\max*(1-(x^n/(K^n+x^n)))+Y2$ $y = V\max*(1-(x^n/(K^n+x^n)))$ $y = V\max*(1-(x/(K+x)))+Y2$ $y = V\max*(1-(x/(K+x)))$ Where: K is $IC_{50}$, Y2 is baseline, and N is Hill Coefficient Each of the compounds of the present invention is believed to provide a $pIC_{50}$ value of at least 5 when tested in each of the above-described assays.

Test compounds are employed in free or salt form.

All research complied with the principles of laboratory animal care (NIH publication No. 85-23, revised 1985) and standard pharmaceutical industry policy on animal use.

Although specific embodiments of the present invention have been illustrated and described in detail, the invention is not limited thereto. The above detailed description of pre- ferred embodiments is provided for example only and should not be construed as constituting any limitation of the invention. Modifications will be obvious to those skilled in the art, and all modifications that do not depart from the spirit of the invention are intended to be included within the scope of the appended claims.

What is claimed is:

1. A compound selected from the group consisting of:

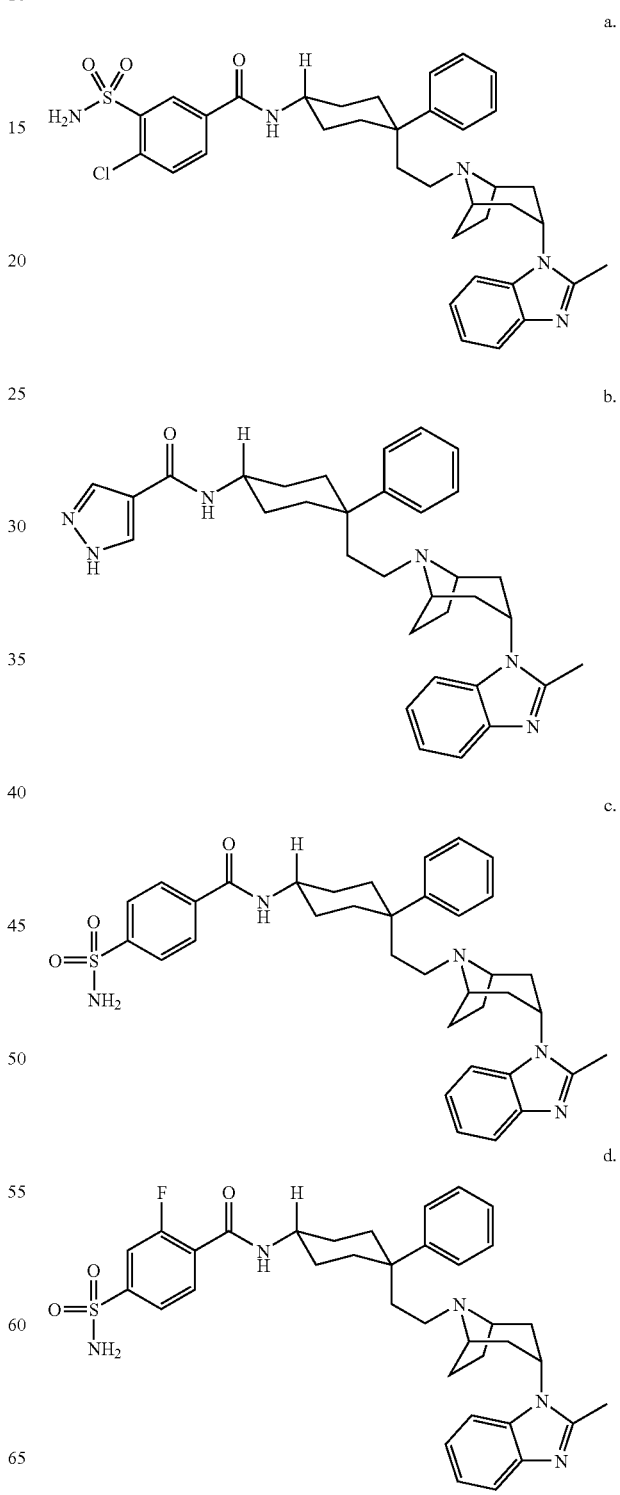

-continued
e.
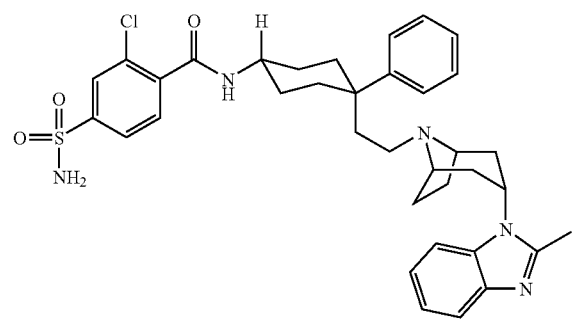
f.
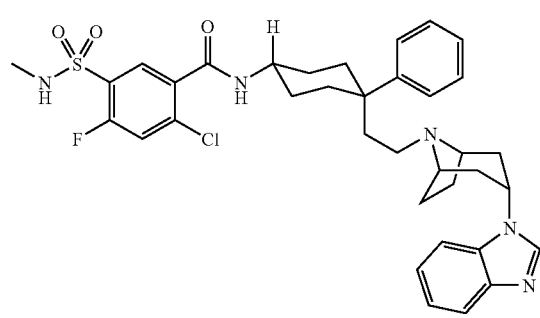
g.
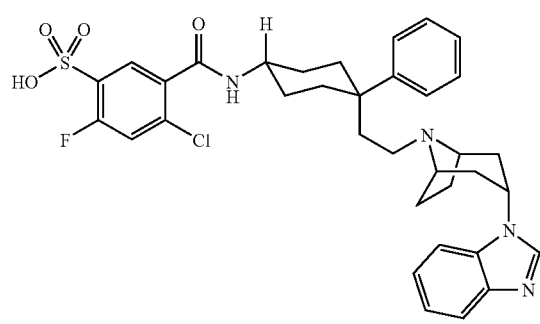
h.
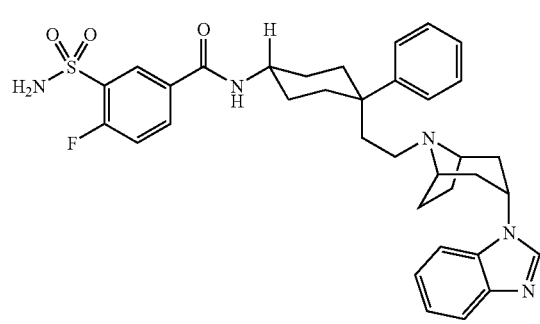
i.
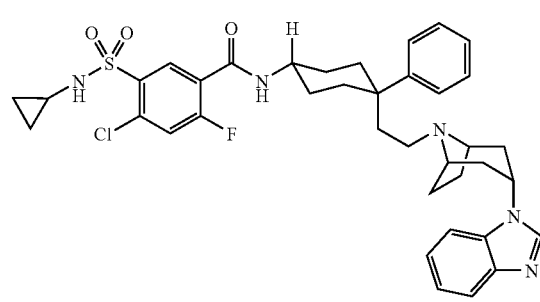
-continued
k.
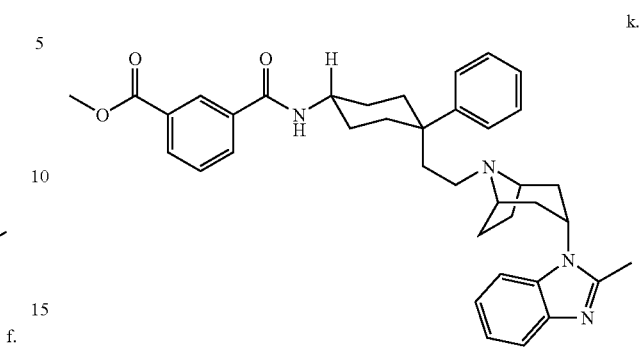
l.
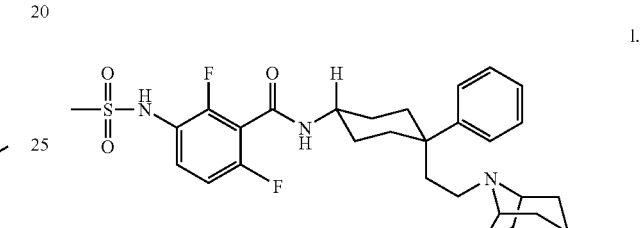
m.
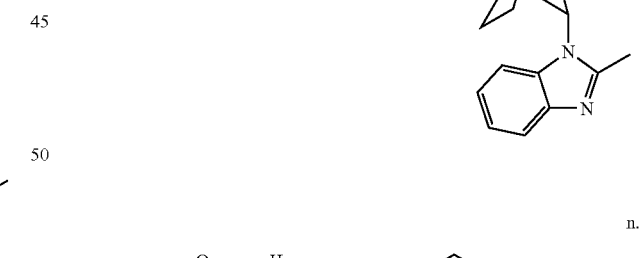
n.
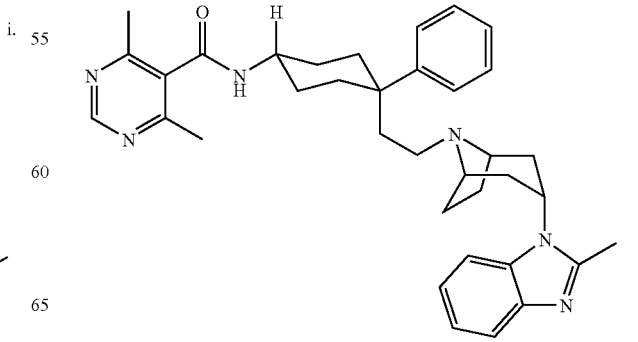

-continued
o.
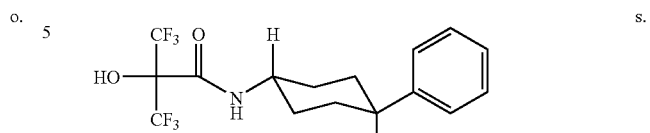
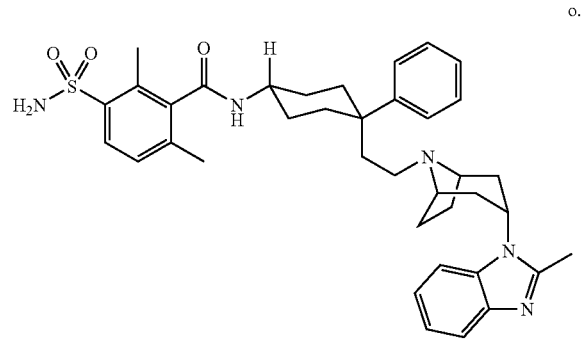
p.
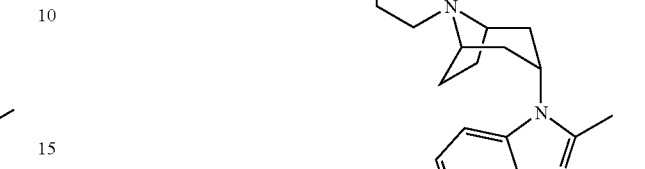
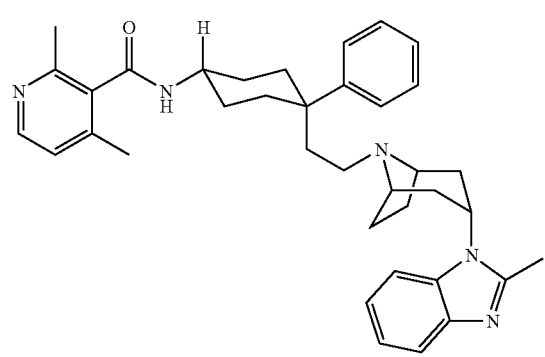
q.
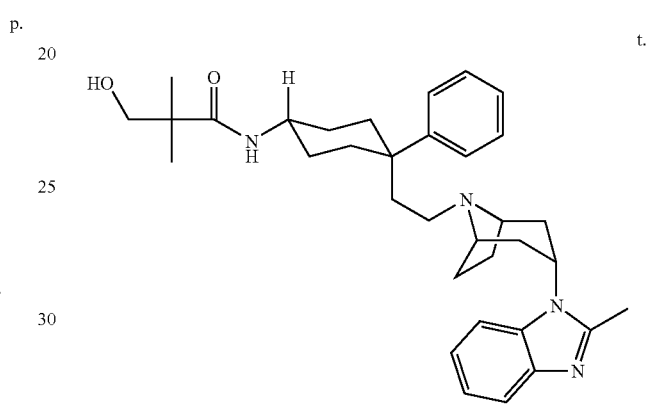
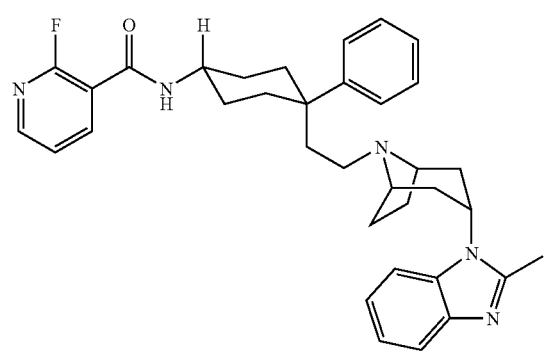
r.
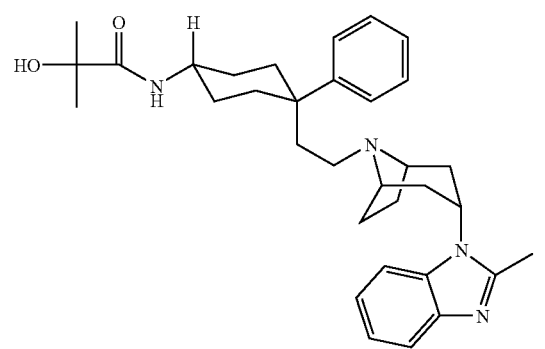
s.
t.
u.
v.
w.
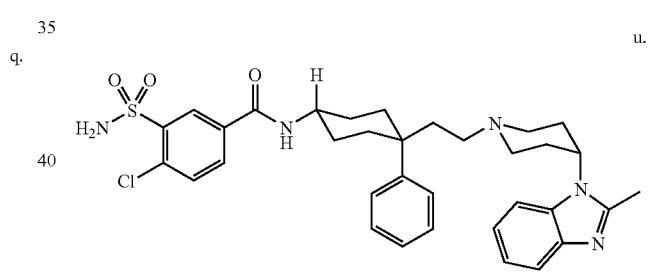
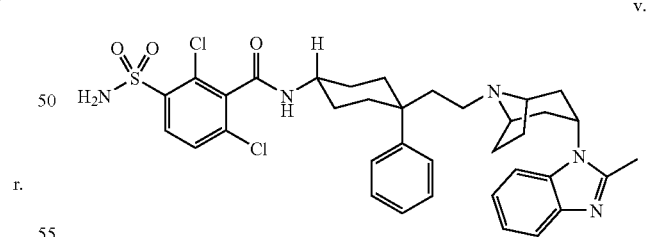
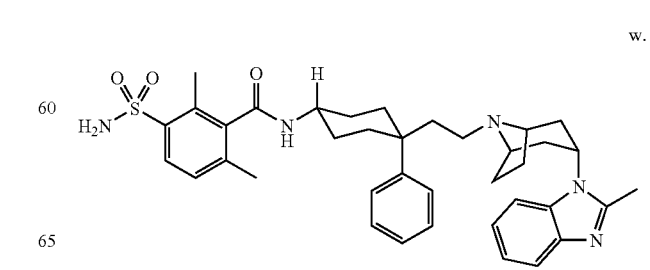

-continued x. 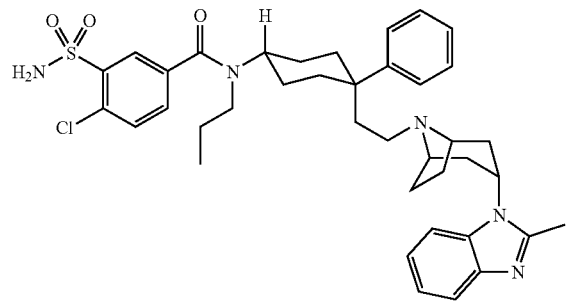

y. 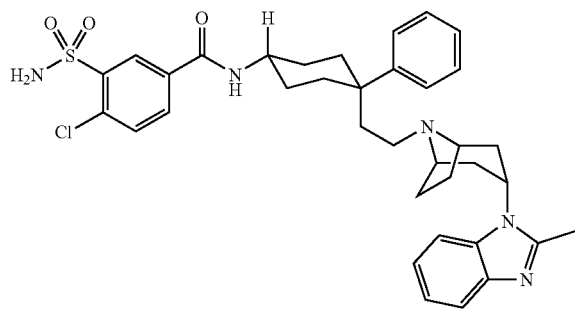

z. 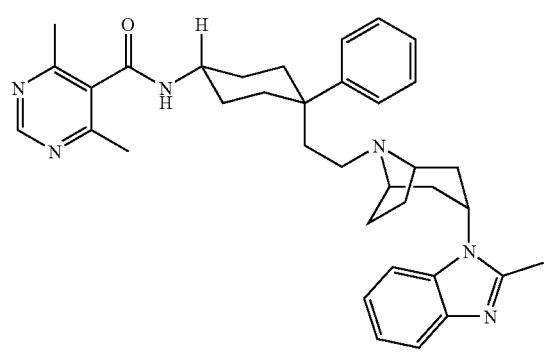

-continued aa. 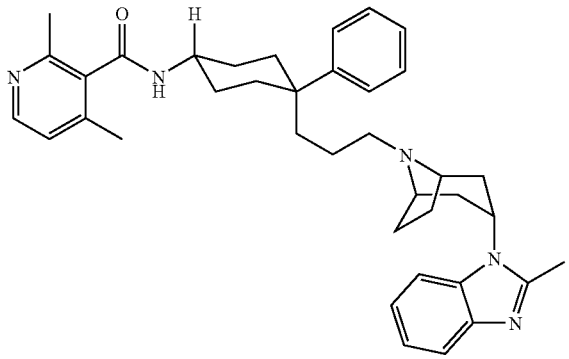

bb. 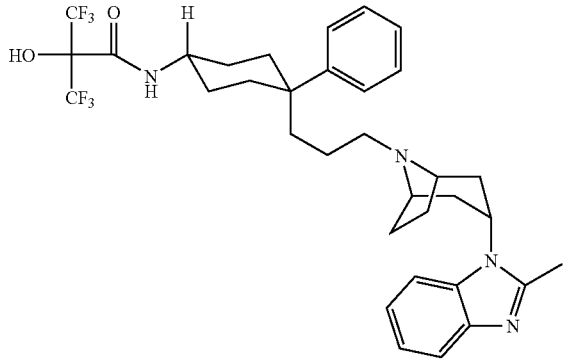

cc. 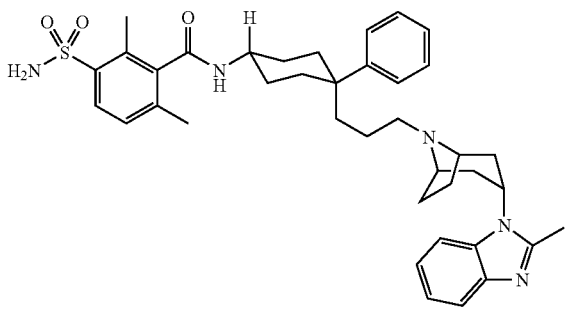

and salts thereof.

2. A pharmaceutical composition comprising a pharmaceutically effective amount of a compound according to claim 1 together with a pharmaceutically acceptable carrier.

3. The pharmaceutical composition according to claim 2 in the form of a tablet or capsule.

4. The pharmaceutical composition according to claim 2 in the form of a liquid.

* * * * *